United States Patent [19]

Plaquevent et al.

[11] Patent Number: 5,670,531
[45] Date of Patent: Sep. 23, 1997

[54] AMINO ACID DERIVATIVES, THE PROCESS FOR THEIR PREPARATION AND THEIR APPLICATIONS TO THERAPY

[75] Inventors: Jean-Christophe Plaquevent, Notre Dame de Bondeville; Denis Danvy, Mont Saint Aignan; Thierry Monteil, Rouen; Hélène Greciet, Val de Reuil; Lucette Duhamel; Pierre Duhamel, both of Mont Saint Aignan; Claude Gros, Paris; Jean-Charles Schwartz, Paris; Jeanne-Marie Lecomte, Paris, all of France

[73] Assignee: Societe Civile Bioprojet, Paris, France

[21] Appl. No.: 462,590

[22] Filed: Jun. 5, 1995

Related U.S. Application Data

[62] Division of Ser. No. 422,652, Apr. 14, 1995, Pat. No. 5,599,951, which is a continuation of Ser. No. 103,156, Aug. 9, 1993, abandoned, which is a continuation of Ser. No. 689,238, filed as PCT/FR90/00659, Sep. 14, 1990, abandoned.

[30] Foreign Application Priority Data

Sep. 15, 1989 [FR] France ..................... 89 12142

[51] Int. Cl.⁶ .................... A61K 31/40; A61K 31/36; C07D 317/54; C07D 405/06
[52] U.S. Cl. .................... 514/397; 549/362; 549/441; 548/454; 548/311.7; 514/466; 514/452; 514/414
[58] Field of Search ..................... 549/441, 362; 546/336, 341, 342; 514/452, 466, 397, 414; 558/254; 548/454, 311.7

[56] References Cited

U.S. PATENT DOCUMENTS 4,401,677  8/1983  Greenberg.

FOREIGN PATENT DOCUMENTS

| 38046 | 10/1981 | European Pat. Off. |
| 38758 | 10/1981 | European Pat. Off. |
| 66956 | 12/1982 | European Pat. Off. |
| 75896 | 4/1983 | European Pat. Off. |
| 82088 | 6/1983 | European Pat. Off. |
| 309766 | 4/1989 | European Pat. Off. |
| 322633 | 7/1989 | European Pat. Off. |

OTHER PUBLICATIONS

Komori et al., Chem. Pharm. Bull., 35(6), 2388 (1987).

*Primary Examiner*—Nicky Chan
*Attorney, Agent, or Firm*—Larson & Taylor

[57] ABSTRACT

Amino acid derivatives having both enkephalinase and ACE inhibiting properties corresponding to the formula:

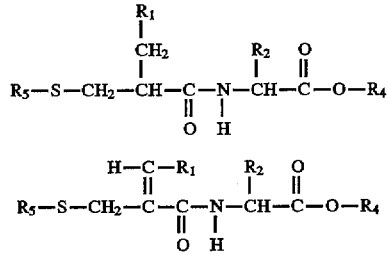

4 Claims, No Drawings

AMINO ACID DERIVATIVES, THE PROCESS FOR THEIR PREPARATION AND THEIR APPLICATIONS TO THERAPY

This is a division of application Ser. No. 08/422,652 filed Apr. 14, 1995, now U.S. Pat. No. 5,599,951, which is a continuation of application Ser. No. 08/103,156 filed Aug. 9, 1993, abandoned which in turn is a continuation of application Ser. No. 07/689,238 filed as PCT/FR90/00659 Sep. 14, 1990, abandoned.

The present invention relates to amino acid derivatives, mixed inhibitors of the enkephalinase enzyme (EC 3.4.24.11) and angiotensin-convertase enzyme (EC 3.4.15.1, ACE).

It also relates to the process for preparing these amino acid derivatives.

It further relates to the application of these amino acid derivatives to the preparation of drugs.

European patent EP-A-0.038.758 (Roques et al.) discloses amino acid derivatives having enkephalinase-inhibiting properties, a peptidase which degrades enkephalins in particular. Enkephalin methionine and leucine are peptides discovered in the brain which are endogenous ligands of the morphine receptor. Moreover, auricular natriuretic factor (ANF) is an endogenous peptide which exerts vasorelaxing, diuretic and natriuretic effects, potentially beneficial in the treatment of cardiovascular and renal diseases. ANF is a substrate for enkephalinase and inhibitors of this peptidase slow down its degradation, increase its plasma levels and induce antihypertensive, diuretic and natriuretic effects (Lecomte et al., Proc. Natl. Ac. Sci., USA, in press).

It is also known, for example in French patent No. 2.628,498 filed in the applicant's name, that certain amino acid derivatives exert an inhibiting effect on the enzyme converting angiotensin I to angiotensin II (ACE), angiotensin II being an active vasomotor substance considered to be the agent responsible for various forms of hypertension. These compounds are thus useful in the treatment of hypertension and cardiac insufficiency.

Amino acid derivatives of the kind described in European patent EP-A-0.038.758 or in French patent No. 2.623.498 are thus known to exert an inhibiting effect on either one or the other of the two enzymes, enkephalinase and ACE, or on both these enzymes at the same time. However, in the latter case, their enkephalinase- and ACE-inhibiting properties are exerted to different degrees. Research up until the present has mainly concentrated on developing amino acid derivatives which have as wide a field of specificity as possible on one or the other of the two enzyme activities described above. Nonetheless, the advantage of having amino acid derivatives at one's disposal which could inhibit enkephalinase and ACE enzymes with the same degree of efficacy is evident. These agents would prevent the formation of angiotensin II and promote the beneficial effects of endogenous ANF at the same time. Furthermore, inactivation of another peptide, bradykinin, seems to depend on both ACE and enkephalinase: the simultaneous inhibition of these two peptidases is likely to promote the known vasorelaxing effects of bradykinin.

The applicant thus found it would be interesting, within the context of extending his previous research, to develop amino acid derivatives likely to inhibit the two enzymes, enkephalinase and ACE, to an equal degree, in particular through the careful selection of certain substituents.

One aim of the invention is thus to provide amino acid derivatives which are mixed inhibitors of enkephalinase and ACE enzymes.

Another aim of the invention is to propose a process for preparing these mixed inhibitors.

Yet another aim of the invention is to provide pharmaceutical compositions which contain these amino acid derivatives as the active principle.

The amino acid derivatives, mixed inhibitors of enkephalinase and ACE enzymes in accordance with the invention, have the following general formulae:

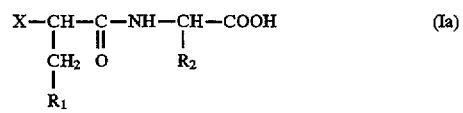  (Ia)

or

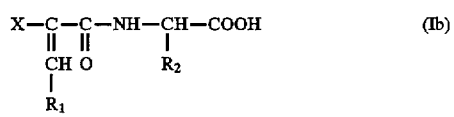  (Ib)

wherein for the formula (Ia) $R_1$ represents a phenyl group mono- or polysubstituted by a halogen atom, particularly fluorine, a biphenyl group or one of the following groups:

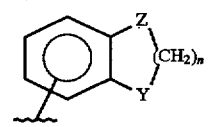

wherein Z, Y and n have the following meanings:

| Z | Y | n |
| --- | --- | --- |
| O | O | 1 |
| O | $CH_2$ | 1 |
| $CH_2$ | $CH_2$ | 1 |
| O | O | 2 |
| $CH_2$ | $CH_2$ | 2 |
| O | $CH_2$ | 2 | or

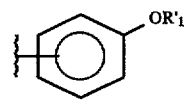

wherein for the formula (Ib) $R_1$ has the meaning defined thereabove and can also be a phenyl group;

wherein $R'_1$ represents a hydrogen, atom, a lower alkyl group, a phenyl group, a lower phenylalkenyl group.

$R_2$ represents a hydrogen atom, a lower alkyl group, a lower hydroxyalkylene group, a phenyl group, a lower phenylalkylene group, a lower hydroxyphenylalkylene group, a lower aminoalkylene group, a lower guanidinoalkylene group, a lower mercaptoalkylene group, a lower alkythio lower alkylene, a lower imidazolylalkylene group, a lower indolylalkylene group, a lower carbamylalkylene group, a lower carboxyalkylene group or one of the following groups:

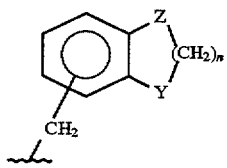

wherein Z, Y and n have the following meanings:

| Z | Y | n |
|---|---|---|
| O | O | 1 |
| O | O | 2 |
| O | CH$_2$ | 1 |
| O | CH$_2$ | 2 |
| CH$_2$ | CH$_2$ | 1 |
| CH$_2$ | CH$_2$ | 2 |

X designates the group responsible for chelating the zinc atom of the enzymes (enkephalinase and ACE) and can be chosen from the group consisting of a mercaptomethyl, hydroxamic acid, an N-carboxyalkyl of formula

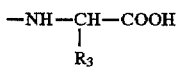

R$_3$ represents a lower alkyl radical, a benzyl lower alkyl radical or a benzyl lower alkoxy radical, phosphorated derivatives of formula

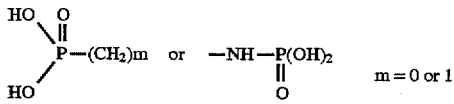

The term "lower alkyl groups" refers to linear or branched chain alkyl groups having 1 to 6 carbon atoms and, preferably, 1 to 4 carbon atoms.

The term "lower alkylene groups" refers to alkylene groups having 1 to 6 carbon atoms and, preferably, 1 to 4 carbon atoms.

The amino acid derivatives in accordance with the invention include in their structure natural amino acids and, more particularly, glycine, alanine, valine, leucine, serine, threonine, cysteine, methionine, aspartic acid, aspargine, glutamic acid, glutamine, lysine, arginine, phenylalanine, tyrosine, tryptophan, histidine, with the exception of proline, as well as non-natural amino acids such as norvaline, norleucine, 3-(3,4-methylenedioxy phenyl) alanine, methionine sulfoxide.

The amino acid derivatives of formula (Ia) or (Ib) in accordance with the invention are new compounds, with the exception of compounds wherein R$_1$ represents a phenyl group mono- or polysubstituted by a halogen atom, already described in European patent EP-A-0.038.758.

The preferred amino acid derivatives in accordance with the invention are derivatives of formula (Ia) or (Ib) wherein the X group which chelates the zinc atom is a mercaptomethyl group.

These amino acid derivatives can also be in the form of a "prodrug" where the mercaptomethyl and carboxyl groups are protected as follows:

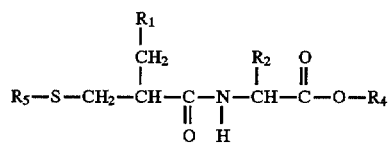

and

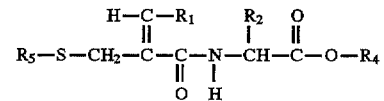

wherein R$_4$ represents, in particular, a linear or branched alkyl group, a phenyl or phenylalkyl group, the latter two groups possibly being mono- or polysubstituted on the phenyl ring, or linear or branched susbtituents including one or more oxygen atoms, and wherein R$_5$ represents a linear or branched aliphatic acyl radical, an aromatic acyl radical possibly mono- or polysubstituted, or a linear or branched acyl radical including one or more oxygen atoms.

The following can be cited as particularly preferred compounds of formula (Ia) or (Ib):

N-(RS)-[1-oxo-2-(mercaptomethyl)-3-(3,4-methylenedioxy phenyl) propyl]glycine and its optically pure forms, N-(RS)-[1-oxo-2-(mercaptomethyl)-3-(3,4-methylenedioxy phenyl) propyl]-(S)-alanine and its optically pure forms, N-(RS)-[1-oxo-2-(mercaptomethyl)-3-(3,4-methylenedioxy phenyl) propyl]-(S)-2-aminobutyric acid, N-(RS)-[1-oxo-2-(mercaptomethyl)-3-(3,4-methylenedioxy phenyl) propyl]-(S)-norvaline, N-(RS)-[1-oxo-2-(mercaptomethyl)-3-(3,4-methylenedioxy phenyl) propyl]-(S)-norleucine, N-(RS)-[1-oxo-2-(mercaptomethyl)-3-(3,4-methylenedioxy phenyl) propyl]-(S)-leucine, N-(RS)-[1-oxo-2-(mercaptomethyl)-3-(3,4-methylenedioxy phenyl) propyl]-(S)-tryptophan, N-(RS)-[1-oxo-2-(mercaptomethyl)-3-(3,4-methylenedioxy phenyl) propyl]-(S)-phenylalanine, N-(RS)-[1-oxo-2-(mercaptomethyl)-3-(3,4-methylenedioxy phenyl) propyl]-(S)-tyrosine, N-(S)-[1-oxo-2-(mercaptomethyl)-3-(3,4-methylenedioxy phenyl) propyl]-(S)-serine N-(S)-[1-oxo-2-(mercaptomethyl)-3-(3,4-methylenedioxy phenyl) propyl]-(S)-methionine, N-(S)-[1-oxo-2-(mercaptomethyl)-3-(3,4-methylenedioxy phenyl) propyl]-(RS)-methionine sulfoxide, N-(S)-[1-oxo-2-(mercaptomethyl)-3-(3,4-methylenedioxy phenyl) propyl]-(RS)-3-(3,4-methylenedioxy phenyl)-alanine, N-(RS)-[1-oxo-2-(mercaptomethyl)-3-(3,4-methylenedioxy phenyl) propyl]-glycine, N-(RS)-[1-oxo-2-(mercaptomethyl)-3-(3,4-methylenedioxy phenyl) propyl]-(S)-alanine, N-(RS)-[1-oxo-2-(mercaptomethyl)-3-(2,3-methylenedioxy phenyl) propyl]-glycine, N-(RS)-[1-oxo-2-(mercaptomethyl)-3-(4-phenoxy phenyl) propyl]-glycine, N-(RS)-[1-oxo-2-(mercaptomethyl)-3-(4-phenoxy phenyl) propyl]-(S)-alanine, N-(RS)-[1-oxo-2-(mercaptomethyl)-3-(4-phenyl phenyl) propyl]-glycine and its optically pure forms, N-[1-oxo-2-(mercaptomethyl)-3-(4-phenyl phenyl) propyl]-(S)-alaniue and its optically pure forms, N-[1-oxo-2-(mercaptomethyl)-3-(4-phenyl phenyl) propyl]-(S)-leucine, N-(RS)-[1-oxo-2-(mercaptomethyl)-3-(3-fluoro phenyl) propyl]-glycine, N-(RS)-[1-oxo-2-(mercaptomethyl)-3-(3-fluoro phenyl) propyl]-(S)-alanine, N-(RS)-[1-oxo-2-(mercaptomethyl)-3-(3,4-difluoro phenyl) propyl]-glycine, N-(RS)-[1-oxo-2-(mercaptomethyl)-3-(3,4-difluoro phenyl) propyl]-(S)-alanine, N-(RS)-[1-oxo-2-(mercaptomethyl)-3-(3,5-difluoro phenyl) propyl]-glycine and its optically pure forms, N-(RS)-[1-oxo-2-(mercaptomethyl)-3-(3,5-difluoro phenyl) propyl]-(S)-alanine, N-(RS)-[1-oxo-2-(mercaptomethyl)-3-(5'-indanyl) propyl]-glycine, N-(RS)-[1-oxo-2-(mercaptomethyl)-3-(5'-indanyl) propyl)-(S)-alanine, N-(RS)-[1-oxo-2-(mercaptomethyl)-3-(2',3'-dihydro-5'-benzofuranyl) propyl]-glycine, N-(RS)-[1-oxo-2-(mercaptomethyl)-3-(2',3'-dihydro-5'-benzofuranyl) propyl]-(S)-alanine, N-(RS)-[1-oxo-2-(mercaptomethyl)-3-(4-methoxy phenyl) propyl]-glycine, N-(RS)-[1-oxo-2-(mercaptomethyl)-3-(4-methoxy phenyl) propyl]-(S)-alanine, N-(S)-[1-oxo-2-(mercaptomethyl)-3-(4-methoxy phenyl) propyl]-glycine, N-(S)-[1-oxo-2-(mercaptomethyl)-3-(4-methoxy phenyl) propyl]-(S)-alanine, N-(RS)-[1-oxo-2-(mercaptomethyl)-3-(4-ethoxy phenyl) propyl]-glycine, N-(RS)-[1-oxo-2-(mercaptomethyl)-3-(4-ethoxy phenyl) propyl]-(S)-alanine, N-(E)-[1-oxo-2-(mercaptomethyl)-2-ene-3-phenyl propyl]-(S)-alanine, N-(E)-[1-oxo-2-(mercaptomethyl)-2-ene-3-phenyl propyl]-(S)-norvaline, N-(E)-[1-oxo-2-(mercaptomethyl)-2-ene-3-phenyl propyl]-(S)-norleucine, N-(E)-[1-oxo-2-(mercaptomethyl)-2-ene-3-phenyl propyl]-(RS)-3-(3,4-methylenedioxy phenyl)-alanine N-(Z)-[1-oxo-2-(mercaptomethyl)-2-ene-3-(3,4-methylenedioxy phenyl)propyl]-glycine, N-[N-(RS)-(1-carboxy pentyl)-(RS)-3-(3,4-methylenedioxy phenyl)alanyl]-glycine hydrochloride, N-[N-(RS)-(1-carboxy-2-phenyl ethyl)-(S)-phenylalanyl]-glycine hydrochloride, N-[N-(RS)-(1-carboxy-2-phenyl ethyl)-(RS)-3-(3,4-methylenedioxy phenyl) alanyl]-glycine hydrochloride, N-(RS)-[2-(dihydroxyphosphinyl)-methyl-1-oxo-3-(3,4-methylenedioxy phenyl) propyl)-(S)-alanine and its calcium monosalt, N-(RS)-[2-(dihydroxyphosphinyl)-methyl-1-oxo-3-(3,4-methylenedioxy phenyl) propyl]-glycine and its calcium monosalt, N-(RS)-[2-(dihydroxyphosphinyl)-methyl-1-oxo-3-(4,4-phenyl phenyl) propyl]-(S)-alanine and its calcium monosalt, N-(RS)-[2-(dihydroxyphosphinyl)-methyl-1-oxo-3-(4,4-phenyl phenyl) propyl]-glycine and its calcium monosalt, The amino acid derivatives of formula (Ia) or (Ib) in accordance with the invention have one, two or three asymmetric carbon atoms and can thus occur in the form of a racemic mixture or in the form of diastereomers. These compounds can be used in racemic or optically active form. The process for preparing these derivatives, described hereafter, uses the racemic mixture or one of the enantiomers as the starting product. When a racemic product is used to start with, the stereomere obtained can be separated in the product by conventional chromatographic or fractional crystallization processes.

The present invention also relates to the process for preparing compounds of formula (Ia) or (Ib) wherein X particularly designates the mercaptomethyl group.

The process in accordance with the invention is characterized in that it successively consists in:

a) reacting an ester of malonic acid such as ethyl malonate of formula

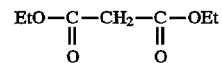

wherein Et designates the ethyl radical with a halogenated compound of formula $R_1$—$CH_2$—Y, $R_1$ having the meaning defined hereinabove, in the presence of an alkaline metal alcoholic solution, in order to form a diester for formula (II)

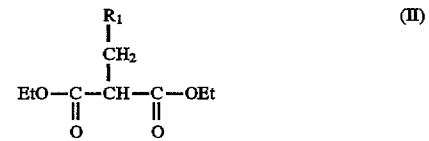

b) monosaponifying the diester of formula (II) to obtain a monoacid of formula (III)

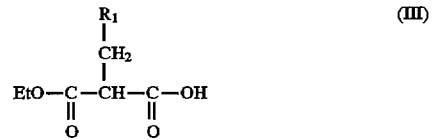

c) preparing, by a Mannich reaction, the acrylic ester of formula (IV), a reaction which consists in treating the monoacid (III) with an organic base such as diethylamine, then with formaldehyde,

d) saponifying the acrylic ester (IV) and following the saponification with a Michaël addition with thioacetic acid $CH_3COSH$ in order to form thioacetyl acid of formula (V)

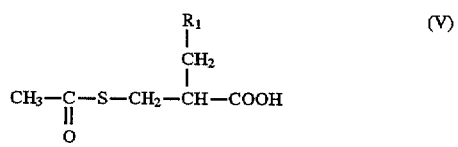

e) possibly splitting thioacetyl acid (V), f) coupling thioacetyl acid of formula (V), in racemic or optically pure form, with the desired aminoester, such as a benzyl aminoester of formula (VI)

wherein $R_2$ and $R_4$ have the meanings defined hereinabove in order to form a compound of formula (VII)

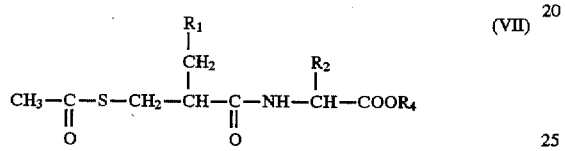

in the presence of a coupling agent such as dicyclohexylcarbodiimide, g) then subjecting compound (VII) to alkaline deprotection in order to form the mixed inhibitors of formula (Ia), Resolution of thioacetyl acid (V) can be carried out by a process such as that described in French patent No. 2.698.463 mentioned hereinabove, according to which the acid is reacted with (+) or (−) ephedrine, depending on the case, the salt of the (+) or (−) enantiomorph obtained is recovered and enantiomorphic acid is released. Resolution of the acid of formula (V) can also be carried out with a chiral amine such as α-methylbenzylamine.

The present invention also relates to the process for preparing compounds of formula (Ib) in which X particularly designates the mercaptomethyl group.

The process in accordance with the invention is characterized in that it successively consists in:

a) carrying out allylic bromination of an ethylenic acid (E) of formula (VIII)

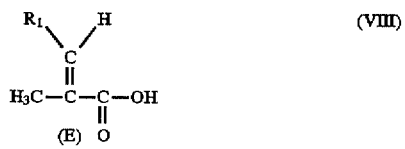

wherein $R_1$ has the meaning defined hereinabove, with a bromination agent such as N-bromo-succinimide, in the presence of a catalytic amount of benzoyl peroxide, in order to form an acid of formula (IX)

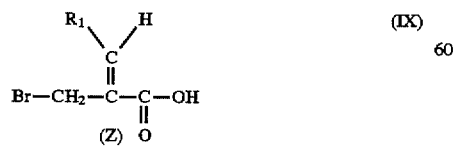

b) substituting the bromine in ethylenic acid of formula (IX) with thioacetic acid in order to form thioacetylated (Z) ethylenic acid of formula (X)

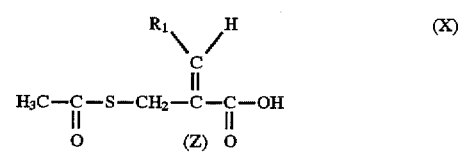

c) isomerizing the acid of formula (X), for example by using an ultraviolet (U.V.) lamp, then separating the isomer mixture (E/Z) obtained with an amine, such as cyclohexylamine, in order to obtain thioacetylated (E) ethylenic acid of formula (XI)

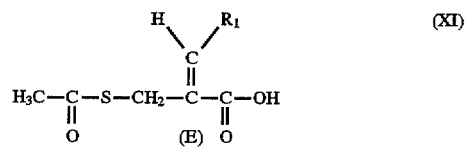

d) coupling thioacetylated (E) ethylenic acid of formula (XI) with the desired aminoester of formula (VI) in the presence of a coupling agent such as dicyclohexylcarbodiimide, in order to obtain the compound of formula (XII)

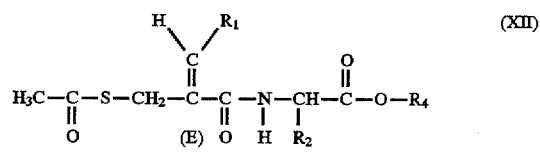

e) then subjecting the compound of formula (XII) to alkaline deprotection in order to form the mixed inhibitors of formula (Ib) (X=mercaptomethyl)

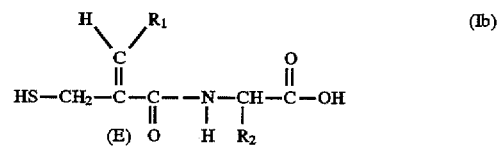

The present invention also relates to the process for preparing compounds of formula (Ia) in which X particularly designates the N-carboxylalkyl group.

The process in accordance with the invention is characterized in that it successively consists in:

a) carrying out diazotization then hydrolysis of an amino acid of formula (XIII)

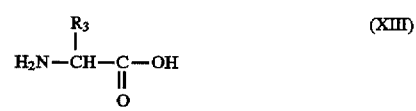

wherein $R_3$ has the meaning defined hereinabove, in order to form a hydroxyacid of formula (XIV)

b) carrying out protection of the hydroxy group of the compound of formula (XIV) with acetyl chloride in order to form the compound of formula (XV)

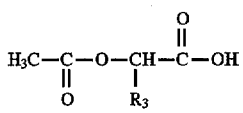
(XV)

c) esterifying the compound of formula (XV), more particularly with tertiary butanol in the presence of phosphorous chloride in order to form the ester of formula (XVI)

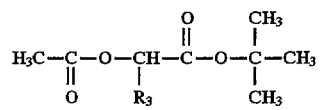
(XVI)

d) releasing the acetyl group of compound (XIV) by alkaline deprotection in order to form the hydroxyester of formula (XVII)

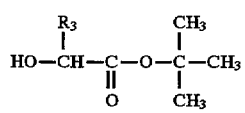
(XVII)

e) activating the alcohol group of the compound of formula (XVII), for example with trifluoromethane sulfonic anhydride, in the presence of pyridine in order to form the compound of formula (XVIII)

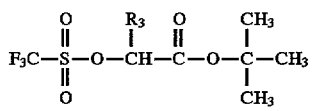
(XVIII)

f) substituting the trifluoromethane sulfonic group of the compound of formula (XVIXI) with an aminoester of formula (XIX)

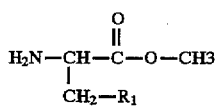
(XIX)

wherein $R_1$ has the meaning defined hereinabove, in the presence of bis-1,8-(dimethylamino)-naphthalene in order to form the compound of formula (XX)

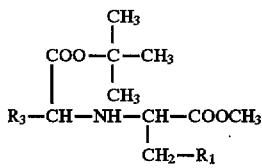
(XX)

g) subjecting the compound of formula (XX) to selective alkaline deprotection in order to form the compound of formula (XXI)

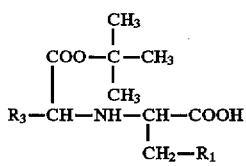
(XXI)

h) coupling the acid of formula (XXI) with the desired aminoester of formula (VI), wherein $R_4$ is a benzyl group, in the presence of a coupling agent such as dicyclohexylcarbodiimide in order to form the compound of formula (XXII)

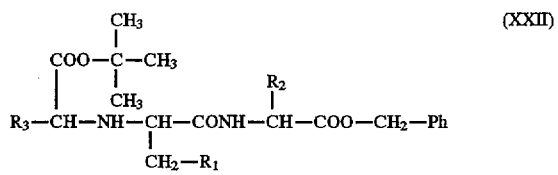
(XXII)

i) hydrogenating the compound of formula (XXII) in the presence of a hydrogenation catalyst, such as Pd/C at a concentration of 10% in ethanol, in order to form the compound of formula (XXIII)

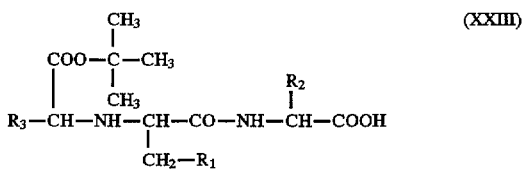
(XXIII)

j) then hydrolyzing the tertiary butyl ester function of the compound of formula (XXIII), for example with a solution of hydrochloric acid in ethyl acetate, in order to form the diacid of formula (Ia) (X=N-carboxy-alkyl)

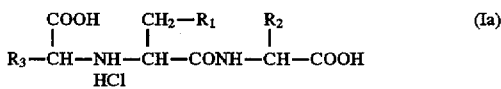
(Ia)

The present invention also relates to the process for preparing compounds of formula (Ia) wherein X particularly designates the phosphonate group.

The process in accordance with the invention is characterized in that it successively consists in:

a) saponifying the acrylic ester of formula (IV),

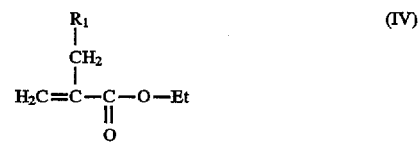
(IV)

wherein $R_1$ has the meaning defined hereinabove and following saponification with the addition of thionyl chloride in order to form acrylic acid chloride of formula (XXIV)

(XXIV)

b) coupling the acid chloride of formula (XXIV) with the desired aminoester of formula (VI), in the presence of triethylamine for example, in order to form the compound of formula (XXV)

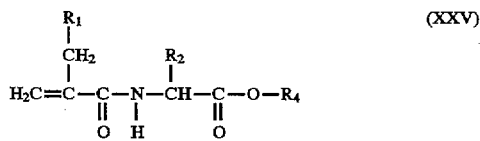
(XXV)

c) carrying out a Michaël addition with a dialkylphosphite, for example with diethylphosphite, in the presence of sodium hydride in order to form the compound of formula (XXVI)

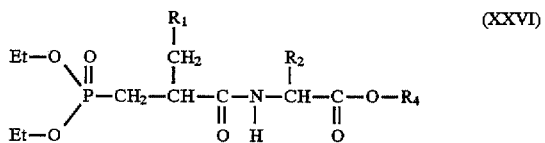

d) then hydrolyzing the protective functions of compound (XXVI) in order to form the inhibitors of formula (Ia)

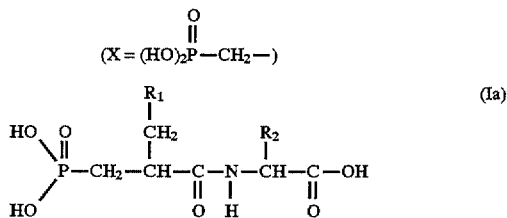

this last step being advantageously carried out with bromotrimethylsilane followed by treatment with a 6N hydrochloric acid aqueous solution.

The compounds in accordance with the invention are characterized in that they have enkephalinase-inhibiting and ACE-inhibiting activities, expressed as 50% inhibiting concentrations ($IC_{50}$), lower than 10 nM, According to another important feature of the invention and which especially applies to compounds of formula (Ia) or (Ib), whose inhibiting concentrations $IC_{50}$ range from 1 to 10 nM, these two concentrations are preferably in a ratio lower than 3–4 for the compound to be equipotent.

Nonetheless, it should be noted that in the case of very active compounds, that is to say those having enkephalinase- and ACE-inhibiting concentrations $IC_{50}$ lower than 1 nM, these compounds no longer have to be equipotent. In this case and at the usual doses, only a fraction of the amino acid derivative is used to inhibit one or the other of the two enzyme activities and there always remains a sufficient amount of free compound to inhibit the other activity.

Thus, the present invention also relates to pharmaceutical compositions which contain compounds of formula (Ia) or (Ib) as the active principle in accordance with the invention.

These pharmaceutical compositions can be administered to humans by oral, parenteral or rectal route.

These pharmaceutical compounds can be in solid or liquid form and presented in pharmaceutical forms commonly used in human medicine, for example simple or coated tablets, capsules, suppositories, preparations for injection.

The pharmaceutical compositions in accordance with the invention are administered in unit doses, preferably ranging from 1 to 200 mg of active principle and at a daily posology ranging from 2 to 400 m of active principle.

Several non limiting examples for implementing the invention are given below to better illustrate the invention.

EXAMPLE 1

Preparation of N-(RS)-[1-oxo-2-(mercaptomethyl)-3-(3,4-methylenedioxy phenyl) propyl]-glycine Step a: Malonic synthesis Preparation of 3-(3,4-methylenedioxy phenyl)-2-ethoxycarbonyl ethyl propanoate 34.9 g (204.69 mmol) of piperonyl chloride and 137.5 g (130.3 ml) (859.4 mmol) of diethyl malonate are placed in a 1-liter three-necked flask equipped with a cooling system, a dropping funnel and a calcium chloride guard. The mixture is stirred and a solution containing 12.2 g (530.4 mmol) of sodium in 312 ml of anhydrous ethanol (1.7M solution) is then added. This mixture is refluxed (oil bath temperature= 80° C.) for 5 hours.

The ethanol is evaporated in a rotary evaporator and the residue is then taken up with water (150 ml) and ethyl ether (100 ml). The ethereal phase is separated and the aqueous phase is extracted a second time with ethyl ether (2 times 100 ml). The combined ethereal phases are washed with water (1 time 100 ml), dried on $MgSO_4$, filtered and concentrated. An oily residue is obtained which is distilled in a vane pump in order to eliminate excess ethyl malonate (60°–70° C. under 0.2 mm Hg). The distillation residue contains diethyl piperonyl malonate (II).

Weight=54.7 g

Yield=91%

$^1$H NMR ($CDCl_3$): 6.9 to 6.55 (m, 3H), 5.95 (s, 2H), 4.1 (q, 4H, J=6.8 Hz), 3.55 (t, 1H, J=6 Hz), 3.1 (d, 2H, J=6 Hz), 1.2 (t, 6H, J=6.8 Hz).

IR: 1710 $cm^{-1}$

Step b: Preparation of 3-(3,4-methylenedioxy phenyl)-2-ethoxy carbonyl-propanoic acid A solution of 54.7 g (186.05 mmol) of the product obtained in the previous step in 24 ml of absolute ethanol is placed in a flask equipped with a dropping funnel and calcium chloride guard. It is cooled down to about 0° C. in an ice bath and a solution of 10.7 (190.69 mmol) of potash in 186 ml of absolute ethanol is added with continuous stirring over a period of 30 minutes. The solution is then stirred between 0° C. and 10° C. for 24 hours.

The solution is evaporated to dryness (rotary evaporator) and the residue is taken up with water (150 ml). It is washed with ethyl ether (3 times 50 ml). The aqueous phase is cooled down and acidified to pH 2 with 3N hydrochloric acid aqueous solution. It is extracted with ethyl ether (4 times 50 ml). The ethereal phases are combined, washed with water (1 time 50 ml), with a saturated NaCl solution (1 time 50 ml), dried on $MgSO_4$, filtered and concentrated. An oil is obtained:

Weight=43.75 g

Yield=87%

$^1$H NMR ($CDCl_3$): 10.1 (s, 1H), 6.9 to 6.3 (m, 3H), 5.85 (s, 2H), 4.1 (q, 2H, J=7.5 Hz), 3.7 (t, 1H, J=7.9 Hz), 3.1 (d, 2H, J=7.9 Hz), 1.15 (t, 3H, J=7.5 Hz),

IR: 1705 $cm^{-1}$

Step c: Preparation of 3-(3,4-methylenedioxy phenyl)-ethyl propenoate 41.71 g (156.8 mmol) of the monoester obtained in the previous step are placed in a flask cooled to 0°–5° C. in an ice bath.

16.25 ml (157 mmol) of diethylamine are added drop by drop at 0°–5° C. with continuous stirring, followed by 15.8 ml (210.8 mmol) of 37% formol in water. The temperature is left to return to room temperature and the solution is stirred for 24 hours.

The reaction mixture is taken up with water (50 ml) then extracted with ether (1 time 200 ml). The organic phase is cooled down in an ice bath and acidified with continuous stirring to pH 2 using a 1N hydrochloric acid aqueous solution. The ethereal phase is then separated, washed with water (2 times 50 ml), washed with a saturated NaCl aqueous solution (1 time 50 ml), dried on $MgSO_4$, filtered and concentrated. An oil is obtained:

Weight=31.6 g

Yield=84%

$^1$H NMR ($CDCl_3$): 6.9 to 6.5 (m, SH), 6.15 (s, 1H), 5.8 (s, 2H), 5.4 (s, 1H), 4.1 (q, 2H, J=6.8 Hz), 3.5 (s, 2H), 1.2 (t, 3H, J=6.8 Hz).

IR: 1700, 1620 $cm^{-1}$

Step d: Preparation of (RS)-2-acetylthiomethyl 3-(3,4-methylene dioxy phenyl) propanoic acid 31.7 g (135 mmol) of the acrylic ester obtained in the previous step in solution in 190 ml of an acetone/water mixture (75/25) are placed in a flask equipped with a dropping funnel. The solution is cooled down to 5° C. in an ice bath and 270 ml (270 mmol) of a 1N NaOH aqueous solution are added over a period of 10 minutes with continuous stirring. The temperature is left to return to room temperature and the solution is stirred for 20 hours.

Acetone is eliminated on a rotary evaporator and the aqueous phase is washed with ethyl ether (3 times 60 ml). The aqueous phase is then cooled down in an ice bath and acidified to pH 2 with a 1N HCl aqueous solution. The acidic aqueous phase is then extracted with ethyl ether (4 times 60 ml). The ethereal phases are combined, washed with water (1 time 60 ml), washed with a saturated NaCl aqueous solution (1 time 60 ml), dried on $MgSO_4$, filtered and concentrated. 2-[(3,4-methylenedioxy phenyl)methyl] propenoic acid is obtained in the form of a solid white mass:

Weight=26.9 g
Yield=96%
MP=121° C.
$^1$H NMR (CDCl$_3$): 9.9 (s, 1H), 6.75 (m, 3H), 6.4 (s, 1H), 5.95 (s, 2H), 5.6 (s, 1H), 3.5 (s, 2H),
IR (Nujol): 1685, 1620 cm$^{-1}$ Preparation of (RS)-2-acetylthiomethyl-3-(3,4-methylenedioxy phenyl) propanoic acid 26.9 g (130.5 mmol) of the acid obtained in the previous step and 15.9 g (209.2 mmol) of thioacetic acid are placed in a flask equipped with a condenser and a calcium chloride guard. The mixture is heated at 70° C. for 24 hours with continuous stirring.

The excess thioacetic acid is evaporated under vacuum (vane pump 1 mm Hg, 60° C.). The pasty yellow residue obtained is taken up three times with 100 ml of ethyl ether. Each time, the ethyl ether is eliminated in a rotary evaporator, then the residue is dried under vacuum. A viscous yellow oil is obtained:

Weight=36.7 g
Yield=100%
$^1$H NMR (CDCl$_3$): 9.9 (s, 1H), 6.85 to 6.5 (m, 3H), 5.85 (s, 2H), 3.25 to 2.6 (m, 5H). 2.3 (s, 3H).
IR: 1700 cm$^{-1}$ Step e: in this step, splitting of the acid obtained in the previous step can be carried out according to Example 2.

Step f: Preparation of N-(RS)-[1-oxo-2-(acetylthiomethyl)-3-(3,4-methylenedioxy phenyl) propyl]-benzyl glycinate 1.37 g (4.85 mmol) of (RS) 2-(acetylthiomethyl)-3-(3,4-methylene dioxy phenyl) propanoic acid in solution in 8 ml of anhydrous THF are placed in a flask equipped with a calcium chloride guard. The flask is cooled down to about 0°–5° C. in an ice bath and are 1.63 g (4.85 mmol) of benzyl glycinate paratoluenesulfonate salt and 0.49 g (4.85 mmol) of triethylamine in 10 ml of chloroform, a solution of 0.74 g (4.85 mmol) of monohydrated hydroxybenzotriazole in 8 ml of THF and a solution of 1.0 g (4.85 mmol) of dicyclohexylcarbodiimide in 7 ml of chloroform successively added with continuous stirring. The mixture is left to return to room temperature then stirred for 6 hours.

The dicyclohexylurea (DCU) precipitate is filtered and evaporated to dryness. The pasty residue is taken up with ethyl acetate (12 ml). DCU which precipitates again is filtered. The organic phase is successively washed with water (1 time 10 ml), with a saturated sodium hydrogenocarbonate aqueous solution (3 times 10 ml), water (1 time 10 ml) and with a saturated NaCl aqueous solution (1 time 10 ml). It is dried on XgSO$_4$, filtered and concentrated.

A solid white residue is obtained which is dissolved in a minimum amount of chloroform. Petroleum ether (25 ml) is added with continuous stirring and left for 15 hours. The solid is filtered, washed with petroleum ether, centrifuged and dried under vacuum.

Weight=1.83 g
Yield=88% (recrystallized in a chloroform/petroleum ether mixture)
MP=74° C.
IR (Nujol): 3310, 1730, 1695, 1640 cm$^{-1}$
$^1$H NMR (CDCl$_3$/TMS): 7.5 to 7.3 (m, 5E), 6.7 (s, 3H), 6.6 (s, broad, 1 H), 5.9 (s, 2H), 5.25 (s, 2H), 4.0 (d, 2H, J=5.3 Hz), 3.2 to 2.4 (m, 5H), 2.3 (s, 3H).
$^{13}$C NMR (CDCl$_3$): 195.4 (s), 172.9 (s), 169.1 (s), 147.3 (s), 145.8 (s), 134.9 (s), 131.9 (e), 128.2 (d), 127.9 (d), 121.6 (d), 108.9 (d), 107.9 (d), 100.5 (t), 66.6 (t), 48.7 (d), 41.0 (t), 37.7 (t), 30.6 (t), 30.2 (g).
Microanalysis: $C_{22}H_{23}O_6NS$
Calc % C=61.54 N=3.26 H=5.36
Found % C=61.45 X=3.36 H=5.41

Step g: Preparation of N-(RS)-[1-oxo-2-(mercaptomethyl)-3-(3,4-methylenedioxy phenyl) propyl]glycine 0.43 g (1.0 mmol) of the compound obtained in the previous step in solution in 3 ml of methanol is placed in a flask. It is purged with argon and the solution is cooled down in an ice bath. 2.1 ml of a 1N soda aqueous solution are added at a temperature of about 5° C. The solution is stirred for 2 hours at 20° C.

The methanol is evaporated under vacuum at a temperature below 35° C. The basic aqueous phase is washed with ether (2 times 10 ml). It is then acidified to pH 1 with a 1N HCl aqueous solution. It is extracted with ether (2 times 10 ml). The extraction phases are washed once with water, dried on MgSO$_4$, filtered and concentrated under vacuum. The residue is dried in a dessicator on phosphorous pentoxide in order to eliminate acetic acid. If necessary, purification by silica chromatography is carried out. N-(RS)-[1-oxo-2-(mercaptomethyl)-3-(3,4-methylenedioxy phenyl) propyl]-glycine is obtained.

Weight=0.29 g
Yield=72% (chromatographied)
MP=94° C. (microscope)
IR (Nujol): 3390, 1740, 1620 cm$^{-1}$
$^1$H NMR (CDCl$_3$/TMS): 10.4 (s, 1H), 6.8 to 6.4 (m, 4H), 5.8 (s, 2H), 3.95 (d, 2H, J=5.3 Hz), 3.1 to 2.2 (m, 5H), 1.6 (t, 1H, J=7.9 Hz)
$^{13}$C NMR (CDCl$_3$): 174.4 (s), 173.1 (s), 147.5 (s), 146.1 (s), 131.9 (s), 121.8 (d), 109.0 (d), 108.2 (d), 100.7 (t), 53.0 (d), 41.2 (t), 37.6 (t), 25.8 (t).
Microanalysis: $C_{13}H_{15}O_5NS$
Calc % C=52.52 N=4.71 H=5.05
Found % C=52.44 N=4.62 H=5.00

EXAMPLE 2

Preparation of (S)-2-(acetylthiomethyl)-3-(3,4-methylenedioxy phenyl) propanoic acid I. Splitting with Methylbenzylamine 32.2 g (114.2 mmol) of racemic 2-(acetylthiomethyl)-3-(3,4-methylenedioxy phenyl) propanoic acid in solution in 200 ml of ethyl ether are placed in a flask. 13.85 5 (114.2 mmol) of (R)-α-methylbenzylamine are added drop by drop with continuous stirring. Precipitation then takes place. The mixture is left for 17 hours.

The salt is filtered, washed with ether (50 ml) and dried under vacuum. The salt of the acid is thus obtained:

Weight=37.45 g
Yield=81%
MP=118° C.
$[\alpha]_D^{25}$=+2.2° (c=1.1 in methanol)
Recrystallization 37.45 g of the previous salt and 100 ml of dichloromethane are placed in a flask equipped with a condenser. The mixture is stirred and heated until the salt is completely dissolved. 100 ml of petroleum ether are then added (40°–60° C.). After the mixture has returned to room temperature, it is left for 24 hours.

The salt is filtered, washed with petroleum ether (50 ml), centrifuged and dried under vacuum:
Weight=18.45 g
Yield=50%
$[\alpha]_D^{25}$=−7.89° (c=1.3 in methanol)
This process is repeated 4 times.

The overall yield of these 5 recrystallizations is 20%. The melting point of the optically pure salt is 192° C.
$[\alpha]_D^{25}$=−23° (c=1.2, MeOH)

Release of the Optically Pure (S) Acid 7.4 g (18.36 mmol) of the optically pure salt are placed in a flask. Water (50 ml), dichloromethane (50 ml) and a 1N HCl aqueous solution are added until a pH value of 2 is obtained. The mixture is stirred until the salt is completely dissolved. The organic phase is separated and the aqueous phase is extracted with dichloromethane (2 times 25 ml). The organic phases are combined, washed with water (2 times 25 ml), dried on $MgSO_4$, filtered and concentrated. An oily residue which crystallizes is obtained:
Weight=4.97 g
Yield=96%
MP=60° C.
$[\alpha]_D^{25}$=−23.0° (c=1.3 in methanol)
$^1$H NMR ($CDCl_3$/TMS): 10.4 (s, 1H), 6.75 (s, 3H), 5.95 (s, 2H), 3.3 to 2.7 (m, 5H), 2.3 (s, 3H), II. Splitting with Ephedrine 35.46 mmoles of racemic acid in solution in 50 ml of ether are placed in a flask. 17.7 mmols of (+) ephedrine in solution in 60 ml of ether are added with continuous stirring. It is left to crystallize at room temperature without stirring. The salt is filtered, washed with ether and dried under vacuum, The salt of the acid is obtained at a yield of 84%
MP=102°–116° C.
$[\alpha]_D^{25}$=+7.7° (c=1.2, MeOH).

Recrystallizations 10 g of the previous salt are placed in a flask. The salt is dissolved in 50 ml of chloroform then 100 ml of ethyl ether are added. It is left for 24 hours.

The salt is filtered, washed with petroleum ether, centrifuged and dried under vacuum.
Weight=7.8 g
Yield=78%
$[\alpha]_D^{25}$=+4.3° (c=1.3, MeOH)
This process is repeated 9 times.
Overall yield of recrystallizations=40%
MP=122° C.
$[\alpha]_D^{25}$=−5.3 (c=1.2, MeOH)

Release of the Optically Pure (S) Acid

Proceed as for splitting with α-methylbenzylamine.
Yield=95%
$[\alpha]_D^{25}$=−25.7° (c=1.8, MeOH)

EXAMPLE 3

Preparation of N-(S)-[1-oxo-2-(acetylthiomethyl)-3-(3,4-methylenedioxy phenyl) propyl]-benzyl glycinate (S)-2-(acetylthiomethyl)-3-(3,4-methylenedioxy phenyl) propanoic acid is coupled with benzyl glycinate following the procedure described in example 1 (step f).

MP=92° C. (Microscope)
Yield=76% (chromatographied)
$[\alpha]_D^{25}$=−15.8° (c=1.2 in methanol)
IR (Nujol): 3280, 1725, 1690, 1640 $cm^{-1}$
$^1$H NMR ($CDCl_3$/TMS): 7.3 (s, 5H), 6.65 (s, 3H), 6.1 (s, broad, 1H), 5.85 (s, 2H), 5.15 (s, 2H), 3.95 (d, 2H, J=5.3 Hz), 3.15 to 2.5 (m, 5H), 2.3 (s, 3H).

The $^{13}$C NMR spectrum is identical to that of the racemic product (example 1).

Microanalysis: $C_{22}H_{23}O_6NS$
Calc % C=61.54 N=3.26 H=5.36
Found % C=61.38 N=3.19 H=5.30

EXAMPLE 4

Preparation of (S) N-(S)-[1-oxo-2-(mercaptomethyl)-3-(3,4-methylenedioxy phenyl) propyl]-glycine The product of example 3 is deprotected according to the method described in example 1 (step g).

Yield=60% (chromatographied)
$[\alpha]_D^{25}$=+54.4° (C=1.0 in methanol)
IR ($CHCl_3$): 1730, 1670 $cm^{-1}$
$^1$H NMR ($CDCl_3$/TMS): 9.6 (s, 1H), 6.8 to 6.45 (m, 4H), 5.95 (s, 2H). 4.05 (d, 2H, J=4 Hz), 3.3 to 2.3 (m, 5H), 1.65 (t, 1H, J=7.3 Hz).

Microanalysis: $C_{13}H15O_5NS$
Calc % C=52.52 N=4.71 H=5.05
Found % C=52.35 N=4.90 H=5.17

EXAMPLE 5

Preparation of N-(RS)-[1-oxo-2-(acetylthiomethyl)-3-(3,4-methylenedioxy phenyl) propyl]-S-benzyl alaninate 2-(acetylthiomethyl)-3-(3,4-methylenedioxy phenyl) propanoic acid in its racemic form (example 1, step d) is coupled with benzyl alaninate of configuration (S) according to the method described in example 1 (step f).

Yield=82% (chromatographied) (50/50 mixture of the two diastereomers)
MP=68° C. (Microscope)
IR (Nujol): 3290, 1730, 1690, 1640 $cm^{-1}$
$^1$H NMR ($CDCl_3$/TMS): 7.25 (s, 5H), 6.6 (s, 3H), 6.4 (m, 1H), 5.8 (s, 2H), 5.1 (s, 2H), 4.6 (quintuplet, 1H, J=7.3 Hz), 3.2 to 2.35 (m, 5H), 2.2 (s, 3H), 1.3 and 1.15 (2 doublets, 3H, J=7.3 Hz).

$^{13}$C NMR ($CDCl_3$): 195.3 (s), 195.0 (s), 171.9 (s),147.1 (s), 145.7 (s), 135.0 (s), 131.9 (s), 131.7 (s), 128.0 (d), 127.6 (d), 121.5 (d) 108.9 (d), 107.7 (d), 100.3 (t), 66.4 (t), 48.8 (d), 48.3 (d), 47.6 (d), 37.7 (t), 31.6 (t), 30.5 (q), 17.8 (q).

Microanalysis: $C_{23}H_{25}O_6NS$
Calc % C=62.30 N=3.16 H=5.64
Found % C=62.21 N=3.11 H=5.55

EXAMPLE 6

Preparation of N-(RS)-[1-oxo-2-(mercaptomethyl)-3-(3,4-methylenedioxy phenyl) propyl]-(S)-alanine Deprotection is carried out according to the operating procedure of example 1 (step g).

Yield=72% (50/50 mixture of the two diastereomers)

M<50° C.

IR (Nujol): 3280, 1725, 1640 cm$^{-1}$ $^1$H NMR (CDCl$_3$/TMS): 8.8 (s, 1H), 6.8 to 6.2 (m, 4H), 5.8 (s, 2H), 4.5 (quintuplet, 1H, J=7 Hz), 3.25 to 2.15 (m, 5H), 1.65 (t, 1H, J=6.5 Hz), 1.4 and 1.25 (2 doublets, 3H, J=7 Hz).

$^{13}$C NMR (CDCl$_3$): 175.6 (s), 173.5 (s), 147.5 (s), 146.0 (s), 132.0 (s), 121.7 (d), 109.0 (d), 108.1 (d), 100.7 (t), 53.4 (d), 2.9 (d), 48.0 (d), 37.9 (t), 37.7 (t), 25.9 (t), 25.7 (t), 18.0 (q), 17.6 (q).

Microanalysis: C$_{14}$H$_{17}$O$_5$NS

Calc % C=54.02 N=4.50 H=5.46

Found % C=53.73 N=4.39 H=5.40

EXAMPLE 7

Preparation of N-(S)-[1-oxo-2-(acetylthiomethyl)-3-(3,4-methylenedioxy phenyl) propyl]-(S)-benzyl alaninate A. Preparation by Coupling Optically Pure (S)-2-(acetylthiomethyl)-3-(3,4-methylenedioxy phenyl) propanoic acid (Example 2)

Yield=77% (chromatographied)

MP=104° C., one diastereomer only (Microscope)

[α]D=−50.6° (c=1.35 in methanol)

IR (Nujol): 3280, 1740, 1695, 1640 cm$^{-1}$ $^1$H NMR (CDCl$_3$/TMS): 7.25 (s, 5H), 6.6 (s, 3H), 6.0 (d, 1H, J=7.5 Hz), 5.85 (s, 2H), 5.0 (s, 2H), 4.5 (quintuplet, 1H, J=7.5 Hz), 3.05 (d, 2H, J=6.1 Hz), 3.0 to 2.4 (m, 3H), 2.25 (s, 3H), 1.3 (d, 3H, J=7.5 Hz).

Microanalysis: C$_{23}$H$_{25}$O$_6$NS

Calc % C=62.30 N=3.16 H=5.64

Found % C=62.20 N=3.20 H=5.30

B. Preparation by Separation of the Diastereomers of Example 5

5.7 g (12.86 mmol) of the compound obtained in example 5 in 20 ml of chloroform are placed in a flask. 80 ml of ethyl ether and 80 ml of petroleum ether are then added to this solution with continuous stirring. The mixture is left for 24 hours.

The solid is filtered, centrifuged and dried under vacuum

Weight=1.7 g

Yield=30%

Product containing 80% of the (S,S) isomer.

The previous process is repeated. 1.7 g (3.83 mmol) of salt (80% rich in the (S,S) diastereoisomer) are dissolved in a minimum amount of chloroform (7 ml). 25 ml of ethyl ether and 25 ml of petroleum ether are then added with continuous stirring. The mixture is left for 24 hours.

The white solid is filtered, centrifuged and dried under vacuum to obtain:

Weight=1.2 g

Recrystallization yield=70%

Product over 95% rich in the (S,S) isomer.

The physical and spectral characteristics are identical to those obtained with the compound of example 7.A.

Overall yield for these two recrystallizations is 21%.

EXAMPLE 8

Preparation of N-(S)-[1-oxo-2-(mercaptomethyl)-3-(3,4-methylenedioxy phenyl) propyl]-(S)-alanine Deprotection is carried out according to the operating procedure of example 1 (step g).

Yield=81%

[α]$_D^{20}$=+12.9° (c=1.35, MeOH)

$^1$H NMR (CDCl$_3$/TMS): 9.05 (s, 1H), 6.8 to 6.6 (m, 3H), 6.45 (d, 1H, J=7 Hz)), 5.85 (s, 2H), 4.55 (quintuplet, 1H, J=7 Hz), 3.1 to 2.25 (m, 3H), 1.5 (t, 1H, J=8.5 Hz)), 1.4 (d, 3H, J=7 Hz)).

Microanalysis: C$_{14}$H$_7$O$_5$NS

Calc % C=54.08 H=5.50 N=4.50

Found % C=53.65 H=5.78 N=4.38

EXAMPLE 9

Preparation of N-(RS)-[1-oxo-2-(acetylthiomethyl)-3-(3,4-methylenedioxy phenyl) propyl]-(S)-2-aminobenzyl butyrate 2-(acetylthiomethyl)-3-(3,4-methylenedioxy phenyl) propanoic acid in its racemic form (example 1, step d) is coupled to 2-aminobenzyl butyrate of configuration (S) according to the operating procedure of example 1 (step f).

Yield=87%

MP=61° C. (Microscope) (50/50 mixture of the diastereomers)

$^1$H NMR (CDCl$_3$/TMS): 7.3 (s, 5H), 6.65 (s, 3H), 6.0 (m, 1H), 5.8 (s, 2H), 5.15 (s, 2H), 4.55 (m, 1H), 3.2–2.4 (m, 5H), 2.3 (s, 3H), 1.65 (m, 2H), 0.8 (t, J=7.5 Hz, ½H), 0.6 (t, J=7.5 Hz, ½H).

$^{13}$C NMR (CDCl$_3$): 195.5, 172.3, 171.6, 147.6, 146.1, 135.3, 132.2, 128.3, 128.0, 121.7, 109.1, 108.1, 100.7, 66.7, 53.1, 52.9, 49.6, 49.35, 37.9, 31.1, 30.9, 30.3, 25.4, 25.2.

IR (Nujol): 3300, 1730, 1690, 1640 cm$^{-1}$

Microanalysis: (C$_{24}$H$_{27}$O$_6$NS)

Calc % C=63.00 H=5.95 N=3.06

Found % C=62.89 H=6.22 N=3.33

EXAMPLE 10

Preparation of N-(RS)-[1-oxo-2-(mercaptomethyl)-3-(3,4-methylenedioxy phenyl) propyl]-(S)-2-aminobutyric acid Deprotection of the compound obtained in example 9 is carried out according to the operating procedure of example 1 (step g).

Yield=69%

MP=118° C. (Microscope) (50/50 mixture of the diastereomers)

$^1$H NMR (CDCl$_3$/TMS): 9.1 (s, 1H), 6.65 (s, 3H), 6.3 (m, 1H), 5.85 (s, 2H), 4.55 (m, 1H), 3.0–2.2 (m, 5H), 1.6 (m, 5H), 0.9 (t, J=7.5 Hz, ½H), 0.7 (t, J=7.5 Hz, ½H).

$^{13}$C NMR (CDCl$_3$): 175.6, 173.5, 147.8, 146.4, 132.3, 121.9, 109.2, 108.4, 100.8, 53.8, 53.2, 37.9, 26.2, 25.8, 25.3, 24.8.

IR (Nujol): 350, 1730, 1630 cm$^{-1}$

Microanalysis: C$_{15}$H$_{19}$O$_5$NS

Calc % C=55.37 H=5.89 N=4.30

Found % C=55.32 H=5.64 N=4.22

EXAMPLE 11

Preparation of N-(RS)-[1-oxo-2-(acetylthiomethyl)-3-(3,4-methylenedioxy phenyl) propyl]-(S)-benzyl norvalinate 2-acetylthiomethyl-3-(3,4-methylenedioxy phenyl) propanoic acid in its racemic form (example 1, step d) is coupled to benzyl norvalinate of configuration (S) according to the operating procedure of example 1 (step f).

Yield=88%

MP=92° C. (Microscope) (50/50 mixture of the diastereomers)

$^1$H NMR (CDCl$_3$/TMS): 7.3 (s, 5H), 6.6 (s, 3H), 6.0 (m, 1H), 5.85 (s, 2H), 5.1 (s, 2H), 4.55 (m, 1H), 3.2–2.3 (m, 5H), 2.1 (s, 3H), 1.6–0.9 (m, 4H), 0. 6 (m, 3H).

$^{13}$C NMR (CDCl$_3$): 195.7, 195.5, 172.3, 171.8, 147.6, 146.1, 135.3, 132.4, 132.1, 128.3, 128.0, 121.8, 109.1, 108, 100.7, 66.7, 51.7, 9.6, 49.2, 37.9, 34.3, 31.1, 30.9, 16.2, 17.8, 13.3.

IR (Nujol): 3300, 1730, 1690, 1635 cm$^{-1}$

Microanalysis: (C$_{25}$H$_{29}$O$_6$NS)

Calc % C=63.68 H=6.20 N=2.97

Found % C=63.47 H=6.13 N=3.19

EXAMPLE 12

Preparation of N-(RS)-[1-oxo-2-(mercaptomethyl)-3-(3,4-methylenedioxy phenyl) propyl]-(S)-norvaline (50/50 mixture of the diastereomers)

Deprotection of the compound of example 11 is carried out according to the operating procedure of example 1 (step Yield=75%

Rf value=0.35 (50/49/1 petroleum ether/ethyl acetate/ acetic acid)

$^1$H NMR (CDCl$_3$/TMS): 9.4 (s, 1H), 6.6 (s, 3H), 6.2 (m, 1H), 5.85 (s, 2H), 4.5 (m, 1H), 3.0–2.3 (m, 5H), 1.9–0.8 (m, 8H).

$^{13}$C NMR (CDCl$_3$): 175.7, 173.5, 147.8, 146.4, 132.3, 121.9, 109.2, 108.4, 100.8, 54.0, 53.5, 51.9, 38.1, 34.0, 33.7, 26.3, 25.8, 18.5, 18.2, 13.4.

IR (Nujol): 3350, 1740, 1630 cm$^{-1}$

Microanalysis: (C$_{16}$H$_{21}$NO$_5$S)

Calc % C=56.62 H=6.23 N=4.13

Found % C=56.41 H=6.08 N=4.25

EXAMPLE 13

Preparation of N-(RS)-[1-oxo-2-(acetylthiomethyl)-3-(3,4-methylenedioxy phenyl) propyl]-(S)-benzyl norleucinate 2-acetylthiomethyl-3-(3,4-methylenedioxy phenyl) propanoic acid in its racemic form (example 1, step d) is coupled to benzyl norleucinate of configuration (S) according to the operating procedure of example 1 (step f).

Yield=85%

MP=104°–126° C. (Microscope) (50/50 mixture of the diastereomers)

$^1$H NMR (CDCl$_3$/TMS): 7.3 (s, 5H), 6.6 (s, 3H), 5.9 (s, 3H), 5.1 (s, 2H), 4.5 (m, 1H), 3.2–2.4 (m, 5H), 2.3 (s, 3H), 1.6 (m, 2H), 1.2 (m, 4H), 0.8 (m, 3H).

$^{13}$C NMR (CDCl$_3$): 195.5, 172.3, 171.8, 147.7, 146.6, 135.3, 132.4, 132.2, 128.3, 128.0, 121.8, 109.1, 108.1, 100.7, 66.7, 51.8, 49.6, 49.4, 37.9, 31.9, 30.9, 30.2, 26.8, 22.1, 13.7.

IR (Nujol): 3300. 1740, 1680, 1640 cm$^{-1}$

Microanalysis: (C$_{26}$H$_{31}$NO$_6$S)

Calc % C=64.81 H=6.43 N=2.88

Found % C=64.50 H=6.53 N=3.06

EXAMPLE 14

Preparation of N-(RS)-[1-oxo-2-(mercaptomethyl (3,4-methylenedioxy phenyl) propyl]-(S)-norleucine Deprotection is carried out according to the operating procedure of example 1 (step g).

Yield=75%

Rf value=0.35 (50/49/1 petroleum ether/ethyl acetate/ acetic acid) (50/50 mixture of the diastereomers)

$^1$H NMR (CDCl$_3$/TMS): 8.2 (s, 1H), 6.6 (s, 3H), 6.4 (m, 1H), 5.8 (s, 2H), 4.5 (m, 1H), 2.9–2.3 (m, 5H), 1.9–0.7 (m, 10H).

$^{13}$C NMR (CDCl$_3$): 175.1. 173.5, 147.8, 146.4, 132.3, 121.8, 109.2, 108.4, 100.8, 53.9, 53.6, 52.1, 37.9, 31.6, 31.3, 27.0, 26.3, 25.9, 22.0, 13.5.

IR (Nujol): 3400, 1700, 1640 cm$^{-1}$

Microanalysis: (C$_{17}$H$_{23}$NO$_5$S)

Calc % C=57.77 H=6,56 N=3.96

Found % C=57.56 H=6.34 N=3.69

EXAMPLE 15

Preparation of N-(RS)-[1-oxo-9-(acetylthiomethyl)-3-(3,4-methylenedioxy phenyl) propyl]-(S)-benzyl leucinate 2-acetylthiomethyl-3-(3,4-methylenedioxy phenyl) propanoic acid in its racemic form (example 1, step d) is coupled to benzyl leucinate of configuration (S) according to the operating procedure of example 1 (step f).

Yield=62%

MP=74° C. (Microscope) (50/50 mixture of the diastereomers)

$^1$H NMR (CDCl$_3$/TMS): 7.3 (s, 5H), 6.6 (s, 3H), 5.9 (m, SH), 5.1 (d, J=3 Hz, 2H), 4.55 (m, 1H), 3.15–2.45 (m, 5H), 2.3 (s, 3H), 1.3 (m, 3H), 0.9 (d, J=5 Hz, 3H), 0.75 (d, J=5 Hz, 3H).

$^{13}$C NMR (CDCl$_3$): 195.6, 195.4, 172.3, 172.1, 147.7, 146.1, 135.4, 132.4, 132.15, 128.4, 128.1, 121.8, 109,2, 108.0, 100.6, 66.7, 50.7, 50.4, 49.6, 49.2, 41.5, 37.8, 31.3, 30.9, 30.2, 24.6, 24.2, 22.4, 21.7, 21.4.

IR (Nujol): 3300, 1730, 1690, 1640 cm$^{-1}$

Microanalysis: (C$_{26}$H$_{31}$NO$_6$S)

Calc % C=64.31 H=6.43 N=2.88

Found % C=64.25 H=6.38 N=2.90

EXAMPLE 16

Preparation of N-(RS)-[1-oxo-2-(mercaptomethyl)-3-(3,4-methylenedioxy phenyl) propyl)-(S)-leucine (50/50 mixture of the diastereomers)

Deprotection is carried out according to the operating procedure of example 1 (step g).

Yield=69%

Rf value=0.7 (ethyl acetate/acetic acid 98/2)

$^1$H NMR (CDCl$_3$/TMS): 10.1 (s, 1H), 6.65 (s, 3H), 6.3 (t,J=7 Hz, 1H), 5.85 (s, 2H), 4.5 (m, 1H), 3.1–2.2 (m, 5H), 1.65 (m, 4H), 0.9 (m, 6H).

$^{13}$C NMR (CDCl$_3$): 176.2, 173.7, 147.8, 146.35, 132.4, 132.15, 121.95, 109.2, 108.2, 100.8, 53.95, 53.35, 50.8, 50.6, 41.2, 40.85, 37.95, 26.4, 25.8, 24.7, 24.45, 22,65, 21.7, 21.4.

IR (Nujol): 3340, 1730, 1630 cm$^{-1}$

Microanalysis: (C$_{17}$H$_{23}$NO$_5$S)

Calc % C=57.77 H=6.56 N=3.96

Found % C=57.48 H=6.43 N=3.62

EXAMPLE 17

Preparation of N-(RS)-[1-oxo-2-(acetylthiomethyl)-3-(3,4-methylenedioxy phenyl) propyl]-(S)-methyl tryptophanate 2-acetylthiomethyl-3-(3,4-methylenedioxy phenyl) propanoic acid in its racemic form (example 1, step d) is coupled to (S) methyl tryptophanate.

Yield=81%

MP=93°–130° C. (Microscope) (50/50 mixture of the diastereomers)

$^1$H NMR (CDCl$_3$/TMS): 8.3 (m, 1H), 7.65–6.85 (M, 4H), 6.6 (m. 3H), 6.0 (t, J=6.7 Hz, 1H), 5.85 (s, 2H), 4.9 (m, 1H). 3.6 (s, 3H), 3.25 (d, J=6.7 Hz, 2H), 3.2–2.3 (m, 5H), 2.25 (s, 3H).

$^{13}$C NMR (CDCl$_3$): 195.6, 172.5, 171.8. 147.55, 146.1, 136.15, 132.4, 132.0, 127.4, 122.9, 172.7, 121.9, 119.4, 118.4, 111.15, 109.3, 109.1, 108.1, 100.7, 52.5, 51.9, 49.35, 49.1, 37.8, 31.0, 30.65, 30.2, 27.5.

IR (Nujol): 3420, 3320, 1730, 1680, 1640 cm$^{-1}$

Microanalysis: C$_{25}$H$_{26}$N$_2$O$_6$S

Calc % C=62.23 H=5.43 N=5.80

Found % C=62.01 H=5.74 N=5.46

EXAMPLE 18

Preparation of N-(RS)-[1-oxo-2-(mercaptomethyl)-3-(3,4-methylenedioxy phenyl) propyl]-(S)-tryptophan Deprotection is carried out according to the operating procedure of example 1 (step g).

Yield=71%

MP=66° C. (Microscope) (50/50 mixture of the diastereomers)

$^1$H NMR (CDCl$_3$, DMSO d$_6$, TMS): 8.6 (s, 1H), 8.85 (s, 1H), 7.6 (m, 1H), 7.4–6.85 (m, 4H), 6.75–6.2 (m, 4N), 5.75 (d, J=6.7 Hz, 2H), 4.35 (m, 1H), 3.1 (m, 2H), 2.9–2.0 (m, 5H), 1.4 (t, J=8 Hz, 1H).

$^{13}$C NMR (CDCl$_3$): 175.1, 173.8, 147.7, 146.1, 136.0, 182.8, 131.8, 127.4, 123.3, 123.0, 122.2, 121.9, 119.6, 118,4, 118.2, 111.2, 109.2, 108.2, 100.7, 53.5, 52.8, 52.6, 37.5, 27.1, 26.8, 26.0, 25.4.

IR (Nujol): 3400, 3350, 1720, 1635 cm$^{-1}$

Microanalysis: (C$_{22}$H$_{22}$N$_2$O$_5$S)

Calc % C=61.96 H=5.20 N=6.57

Found % C=60.59 H=5.46 N=6.82

EXAMPLE 19

Preparation of N-(RS)-[1-oxo-2-(acetylthiomethyl)-3-(3,4-methylenedioxy phenyl) propyl]-(S)-benzyl phenylalaninate 2-acetylthiomethyl-3-(3,4-methylenedioxy phenyl) propanoic acid in its racemic form (example 1, step d) is coupled to (S) benzyl phenylalaninate according to the operating procedure of example 1 (step f).

Yield=73%

MP=99°–105° C. (Microscope) (50/50 mixture of the diastereomers)

$^1$H NMR (CDCl$_3$/TMS): 7.3 (s, 5H), 7.3–6.9 (m, 5H), 6.6 (s, 3H), 5.9 (m, 1H), 5.85 (s, 2H); 5,1 (s, 2H), 4.8 (t, J=7 Hz, 1H), 3.2–2.5 (m, 5H), 2.3 (s, ½H), 2.25 (s, ½H).

$^{13}$C NMR (CDCl$_3$): 195.4, 172.1, 170,8. 147.6, 146.1, 135.3, 134,8, 32.7, 131.9, 129.0, 128.3, 127.0, 121.5, 109.0, 108.0, 100.6, 66.8, 2.5, 49.5, 37.7, 31.15, 30.7, 30.2.

IR (Nujol): 3300, 1925, 1685, 1640 cm$^{-1}$

Microanalysis: C$_{29}$H$_{29}$NO$_6$S

Calc % C=67.03 H=5.63 N=2.69

Found % C=67.02 H=5.51 N=2.90

EXAMPLE 20

Preparation of N-(RS)-[1-oxo-2-(mercaptomethyl)-3-(3,4-methylenedioxy phenyl) propyl]-(S)-phenylalanine (50/50 mixture of the diastereomers)

Deprotection is carried out according to the operating procedure of example 1 (step g).

Yield=79%

Rf value=0.7 (ethyl acetate/acetic acid: 98/2)

$^1$H NMR (CDCl$_3$/TMS): 8.8 (s, 1H), 7.3–6.7 (m, 5H), 6.6 (m, 3H), 6.1 (d, J=7.3 Hz, 1H), 5.85 (m, 2H), 4.85 (m, 1H), 3.3–2.1 (m, 7H), 1.5 (t, J=8.5 Hz, 1H).

$^{13}$C NMR (CDCl$_3$): 174.5, 173.3, 147.7, 146.2, 135.3, 132.1, 129,3, 129.1, 128.5, 127.1, 121.9, 109,2, 108.9, 108.2, 100.8, 53,6, 53.3, 52.9, 52.6, 37.7, 37.2, 26.0, 25.5.

IR (CDCl$_3$): 3420, 1720, 1660 cm$^{-1}$

Microanalysis: (C$_{20}$H$_{21}$NO$_5$S)

Calc % C=62.00 H=5.46 N=3.61

Found % C=61.71 H=5.19 N=3.40

EXAMPLE 21

Preparation of N-(RS)-[1-oxo-2-(acetylthiomethyl)-3-(3,4-methylenedioxy phenyl) propyl]-(S)-benzyl tyrosinate (50/50 mixture of the diastereomers)

2-acetylthiomethyl 3-(3,4-methylenedioxy phenyl) propanoic acid in its racemic form (example 1, step d) is coupled to (S) benzyl tyrosinate according to the operating procedure of example 1 (step f).

Yield=90% (chromatographied)

Rf value=0.7 (50/50 petroleum ether/ethyl acetate)

MP<45° C.

$^1$H NMR (CDCl$_3$/TMS): 7.25 (s, 5H), 7.15–6.3 (m, 8H of which 1H exchangeable by D$_2$O), 6.1 (d, J=8 Hz, 1H), 5.8 (s, 2H), 5.1 (s, 2H), 4.8 (t, J=6.3 Hz, 1H), 3.2–2.4 (m, 7H), 2.23 (s, 1, 5H), 2.19 (s, 1, 5H), $^{13}$C NMR (CDCl$_3$): 196.0. 172.7, 171.0, 155.3, 147.7, 146.2, 134.9, 131.9, 130.3, 128.5, 126.8, 126.6, 121.9, 115.4, 109.1, 108.2, 100.7, 67.0, 53.2, 53.0, 49.7, 49.4, 37.9, 37.0, 31.1, 30.6, 30.3.

IR (Nujol): 3300, 1730, 1690, 1635 cm$^{-1}$

Microanalysis: (C$_{29}$H$_{29}$NO$_7$S)

Calc % C=65.03 H=5.45 N=2.61

Found % C=65.19 H=5.39 N=2.73

EXAMPLE 22

Preparation of N-(RS)-[1-oxo-2-(mercaptomethyl)-3-(3,4-methylenedioxy phenyl) propyl]-(S)-tyrosine (50/50 mixture of the diastereomers)

Deprotection of the compound of example 21 is carried out according to the operating procedure of example 1 (step g).

Yield=85% (chromatographied)

Rf value=0.5 (50/49/1 petroleum ether/ethyl acetate/acetic acid)

MP=62°–65° C. (Microscope)

$^1$H NMR (CDCl$_3$, DMSOd$_6$, TMS): 7.3–6.00 (m, 10H), 5.65 (s, broad, 2H), 4.65 (m, 1H), 3.15–2.00 (m, 7H), 1.65 (t, J=8 Hz, 1H).

IR (Nujol): 3300, 1730, 1640 cm$^{-1}$

Microanalysis: C$_{20}$H$_{21}$NO$_6$S

Calc % C=59.54 H=5.24 N=3.47

Found % C=59.36 H=5.30 N=3.38

EXAMPLE 23

Preparation of N-(S)-[1-oxo-2-(acetylthiomethyl)-3-(3,4-methylenedioxy phenyl) propyl]-(S)-methyl serinate (S)-2-acetylthiomethyl 8-(3,4-methylenedioxy phenyl) propanoic acid (example 2) is coupled to (S) methyl serinate according to the operating procedure of example 1 (step f).

Yield=89% (chromatographied)
MP=120° C.
[α]$_D^{20}$=−15.5° (C=1.1, CHCl$_3$)
IR (Nujol): 3460, 3260, 1725, 1690, 1630 cm$^{-1}$
$^1$H NMR (CDCl$_3$/TMS): 6.85 (m, 3H), 6.4 (d, 1H, J=6.6 Hz), 5.85 (s, 2H), 4,7 to 4,4 (m, 1H), 4.0 to 3.8 (m, 2H), 3.7 (s, 3H), 3.2 to 2.4 (m, 6H), 2.25 (s, 3H).

Microanalysis: C$_{17}$H$_{21}$O$_7$NS
Calc % C=53.26 H=5.48 N=3.65
Found % C=53.46 H=5.59 N=3.85

EXAMPLE 24

Preparation of N](S)-[1-oxo-2-(mercaptomethyl)-3-(3,4-methylenedioxy phenyl) propyl]-(S)-serine Deprotection of the compound of example 23 is carried out according to the operating procedure of example 1 (step g).

Yield=65% (chromatographied)
MP=124° C.
[α]$_D^{20}$=+20.3° (c=1.0, EtOH)
IR (Nujol): 8840, 1750, 1630 cm$^{-1}$
$^1$H NMR (CDCl$_3$/DMSO/TMS): 7.0 (d, 1H, J=7.7 Hz), 6.7 (s, 8H), 5.85 (s, 2H), 5.2 to 4.4 (m, 8H), 8.9 (d, 2H, J=3.5 Hz), 3.0 to 2.4 (m, 5H), 1.6 (t, 1H, J=8.6 Hz).

Microanalysis: C$_{14}$H$_{17}$O$_6$NS
Calc % C=51.37 H=5.19 N=4.28
Found % C=51.08 H=5.24 N=4.26

EXAMPLE 25

Preparation of 1-(S)-[1-oxo-2-(acetylthiomethyl)-3-(3,4-methylenedioxy phenyl) propyl]-(S)-methyl methioninate (S)-2-acetylthiomethyl-3-(3,4-methylenedioxy phenyl) propanoic acid (example 2) is coupled to (S) methyl methioninate according to the operating procedure of example 1 (step f).

Yield=71% (Chromatographied)
MP=85° C.
[α]$_D^{20}$=−33.3° (c=1.3, CHCl$_3$)
IR (Nujol): 3280, 1730, 1690, 1640 cm$^{-1}$
$^1$H NMR (CDCl$_3$/TMS): 6.85 (m, 3H), 6.2 to 5.9 (m, 1H), 5,85 (s, 2H), 4.6 (quintuplet, 1H, J=6.6 Hz), 3.85 (s, 3H), 3.1 (d, 2H, J=6.6 Hz), 3.0 to 2.3 (m, 7H), 2.25 (s, 3H), 2.0 (s, 3H).

Microanalysis: C$_{19}$H$_{25}$O$_6$NS$_2$
Calc % C=53.38 H=5.89 N=3.28
Found % C=53.74 H=5.67 N=3.53

EXAMPLE 26

Preparation of N-(S)-[1-oxo-2-(mercaptomethyl)-3-(3,4-methylenedioxy phenyl) propyl]-(S)-methionine Deprotection of the compound of example 25 is carried out according to the operating procedure of example 1 (step g).

Yield=56% (chromatographied)
[α]$_D^{20}$=+2.2° (c=0.9, EtOH)
IR (Nujol): 3300, 1720, 1640 cm$^{-1}$ $^1$H NMR (CDCl$_3$/TMS): 9,5 (s, 1H), 6.6 (m, 4H), 5.8 (s, 2H), 4.9 to 4.4 (m, 1H),.. 3.0 to 1.3 (m, 1OH), 2.0 (s, 3H).

Microanalysis: C$_{16}$H$_{21}$O$_6$NS$_2$
Calc % C=51.73 H=5.70 N=3.77
Found % C=51.97 H=5.79 N=3.75

EXAMPLE 27

Preparation of N-(S)-[1-oxo-2-(acetylthiomethyl)-3-(3,4-methylenedioxy phenyl) propyl)-(RS)-methylsulfoxide methioninate (S)-2-(acetylthiomethyl)-3-(3,4-methylenedioxy phenyl) propanoic acid (example 2) is coupled to (RS) methyl sulfoxide methioninate according to the operating procedure of example 1 (step f).

Yield=27%
$^1$H NMR (CDCl$_3$/TMS): 6.8 to 6.5 (m, 3H), 6,2 (d, 2H, J=8 Hz), 5.85 (s, 2h), 4.7 to 4.4 (m, 1H), 3.65 and 3.6 (s, 3H), 3.05 (d, 2H, J=6.7 Hz), 3.0 to 1.5 (m, 7H), 2.25 (s, 3H), 2.05 and 1.95 (s, 3H).

IR (Nujol): 3300, 1740, 1690, 1650 cm$^{-1}$
Microanalysis: C$_{19}$H$_{25}$O$_7$NS$_2$
Calc % C=51.45 H=5.68 N=3.16
Found % C=51.39 H=5.52 N=3.23

EXAMPLE 28

Preparation of N-(S)-[1-oxo-2-(mercaptomethyl)-3-(3,4-methylenedioxy phenyl) propyl]-(RS)-methionine sulfoxide Deprotection of the compound of example 27 is carried out according to the operating procedure of example 1 (step g).

Yield=71%
$^1$H NMR (CDCl$_3$/TMS): 8.2 (s, 1H), 6.8 to 6.2 (m, 4H), 5.9 and 5.85 (s, 2H), 4.8 to 4.5 (m, 1H), 3.2 to 1.3 (m, 9H), 2.05 and 1.95 (s, 3H), 1.55 (t, 1H, J=8 Hz).

IR (Nujol): 1725, 1630 cm$^{-1}$
Microanalysis: C$_{16}$H$_{21}$O$_6$NS$_2$
Calc % C=49.60 H=5.46 N=3.61
Found % C=50.00 H=5.39 N=3.72

EXAMPLE 29

Preparation of N-(S)-[1-oxo-2-(acetylthiomethyl)-3-(3,4-methylenedioxy phenyl) propyl]-(RS)-3-(3,4-methylenedioxy phenyl methyl alaninate (S)-2-(acetylthiomethyl)-3-(3,4-methylenedioxy phenyl) propanoic acid (example 2) is coupled to (RS) 3-(3,4-methylenedioxy phenyl) methyl alaninate according to the operating procedure of example 1 (step f).

Yield=58%
MP=98° C.
$^1$H NMR (CDCl$_3$/TMS): 6.8 to 6.0 (m, 6H), 5.85 (s, 4H), 5.8 to 5.6 (m, 1H), 4.95 to 4.55 (m, 1H), 3.65 and 3.6 (s, 3H), 3.15 to 2.4 (m, 7H), 2.3 and 2.25 (s, 3H).

IR (Nujol): 3300, 1730, 1700 to 1680, 1650, 1645 cm$^{-1}$
Microanalysis: C$_{24}$H$_{25}$O$_8$NS
Calc % C=59.13 H=5.17 N=2.87
Found % C=59.50 H=5.23 N=2.90

EXAMPLE 30

Preparation of N-(S)-[1-oxo-2-(mercaptomethyl)-3-(3,4-methylenedioxy phenyl) propyl)-(RS)-3-(3,4-methylenedioxy phenyl)-alanine Deprotection of the compound of example 29 is carried out according to the operating procedure of example 1 (step g).

Yield=74%

MP=121° C.

$^1$H NMR (CDCl$_3$/TMS): 9.4 (s, 1H), 7.0 to 6.0 (m, 6H), 5.8 (s, 4H), 5.0 to 4.6 (m, 1H), 3.9 to 3.6 (m, 1H), 3.25 to 2.2 (m, 7H), 1.5 and 1.4 (t, 1H, J=8 Hz).

IR (Nujol): 1705, 1640 cm$^{-1}$

Microanalysis: C$_{21}$H$_{21}$O$_7$NS

Calc % C=58.46 H=4.91 N=3.25

Found % C=58.76 H=4.97 N=3.39

EXAMPLE 31

Preparation of N-(RS)-[1-oxo-2-(acetylthiomethyl)-3-(3,4-ethylenedioxy phenyl) propyl]-benzyl glycinate A. Preparation of (RS)-2-acetylthiomethyl-3-(3,4-ethylenedioxy phenyl) propanoic acid It is obtained in the same way as in example 1 (step d) by addition of thioacetic acid to 2-[(3,4-ethylenedioxy phenyl) methyl] propenoic acid.

Yield=98%

IR (Nujol): 1720, 1690 cm$^{-1}$ $^1$H) NMR (CDCl$_3$/TMS): 8.5 (s, 1H), 6.8 to 6.5 (m, 3H), 4.2 3.15 to 2.7 (m, 5H), 2.3 (s, 3H).

B. Preparation of N-(RS)-[1-oxo-2-(acetylthiomethyl)-3-(3,4-ethylenedioxy phenyl) propyl]-benzyl glycinate The acid obtained in step A is coupled to benzyl glycinate in the presence or HOBT and DCC, according to the operating procedure described in example 1.

Yield=92% (chromatographied)

MP=62°C. (microscope)

IR (Nujol): 3290, 1745, 1670, 1640 cm$^{-1}$ $^1$H NMR (CDCl$_3$/TMS): 7.4 (s, 5H), 7.0 to 6.55 (m, 3H), 5.9 (s, 1H), 5.2 (s, 2H), 4.2 (s, 4H), 4.0 (dd, 1H, J=5.3 Hz), 3.95 (dd, 1H, J=5.3 Hz), 3.2 to 2.4 (m, 5H), 2,3 (s, 3H).

$^{13}$C NMR (CDCl$_2$): 196.4 (s), 173.1 (s), 169.3 (s), 143.2 (s), 142.1 (s), 135.3 (s), 131.5 (s), 128.4 (d), 128.0 (d), 121.6 (d), 117.3 (d), 116.9 (d), 66.7 (t), 63.9 (t), 48.6 (d), 41.1 (t), 37.2 (t), 30.7 (t), 30.2 (q).

Microanalysis: C$_{23}$H$_{25}$O$_6$NS

Calc % C=62.30 H=5.64 N=3.16

Found % C=62.15 H=5.60 N=3.02

EXAMPLE 32

Preparation of N-(RS)-[1-oxo-2-(mercaptomethyl)-3-(3,4-ethylenedioxy phenyl) propyl)]-glycine Deprotection of the compound of example 31 is carried out according to the operating procedure of example 1 (step g).

Yield=66%

MP=138° C. (Microscope)

IR (Nujol): 3480, 1745, 1630 cm$^{-1}$ $^1$H NMR (CDCl$_3$-DMSO d$_6$/TMS): 7.6 (s, 1H), 6.75 (s, 3H), 5.8 (m, 1H), 4.2 (s, 4H), 3.9 (d, 2H, J=5.3 Hz), 3.15 to 2.1 (m, 5H), 1.7 (t, 1H, J=6.6 Hz).

Microanalysis: C$_{14}$H$_{17}$O$_6$NS

Calc % C=54.02 H=5.47 N=4.50

Found % C=53.76 H=5.38 N=4.26

EXAMPLE 33

Preparation of N-(RS)-[1-oxo-2-(acetylthiomethyl)-3-(3,4-ethylenedioxy phenyl) propyl]-(S)-benzyl alaninate (50/50 mixture of the diastereomers)

2-acetylthiomethyl-3-(3,4-ethylenedioxy phenyl) propanoic acid in its racemic form (example 1, step d) is coupled to (S) benzyl alaninate according to the operating procedure of example 1 (step f).

Yield=78%

Rf value=0.2 (50/50 in ether/petroleum ether) $^1$H NMR (CDCl$_3$/TMS): 7.3 (s, 5H), 6.8–6.5 (m, 3H), 6.0 (m, 1H), 5.1 (s, 2H), 4.5 (m, 1H), 4.2 (s, 4H), 3.2–2.4 (m, 5H), 2.3 (s, 3H), 1.35 (d, J=7Hz, 1.5H), 1.15 (d, J=7 Hz, 1.5H).

$^{13}$C NMR (CDCl$_3$): 195.9, 172.3, 143.2, 142.2 135.3, 131.8, 131.5, 128.5, 128.3, 128.0, 121.7, 117.5, 117.1, 66.8, 64.2, 49.4, 49.0, 48.0, 47.8, 37.7, 37.5, 30.9, 30.7, 30.3, 18.3, 18.0.

IR (CCl$_4$): 3400, 1735, 1675 cm$^{-1}$

Microanalysis: C$_{24}$H$_{27}$O$_6$NS

Calc % C=63.00 H=5.95 N=3.06

Found % C=62.73 H=5.93 N=3.29

EXAMPLE 34

Preparation of N-(RS)-[1-oxo-2-(mercaptomethyl)-3-(3,4-ethylenedioxy phenyl) propyl]-(S)-alanine (50/50 mixture of the diastereomers)

Deprotection of the compound of example 33 is carried out according to the operating procedure of example 1 (step g).

Yield=86%

Rf value=0.3 (50/49/1 petroleum ether/ethyl acetate/ acetic acid) $^1$H NMR (CDCl$_3$/TMS): 9.05 (s, 1H), 6.9–6.4 (m, 3H), 6.25 (m, 1H), 4.55 (m, 1H), 4.2 (s, 4H), 3.05–2.3 (m, 5H), 1.6 (t, J=8.3 Hz, 1H), 1.4 (d, J=6.7 Hz, 1.5H), 1.25 (d, J=6.7 Hz, 1.5 Hz), $^{13}$C NMR (CDCl$_3$): 175.9, 173.7, 143.4, 142.3, 131.8, 131.5 (C$_5$), 121.8, 117.6, 117.3, 64.3, 53.6, 53.1, 48.0, 37.6, 37.3, 26.0, 25.8, 18.0, 17.7, IR (CDCl$_3$): 3400, 1720, 1650 cm$^{-1}$ Microanalysis: C$_{15}$H$_{19}$NO$_5$S Calc % C=55.37 H=5.88 N=4.30

Found % C=55.26 H=5.65 N=4.19

EXAMPLE 35

Preparation of N-(RS)-[1-oxo-2-(acetylthiomethyl)-3-(2,3-methylenedioxy phenyl) propyl]benzyl-glycinate A. Preparation of (RS)-2-acetylthiomethyl-3-(2,3-methylenedioxy phenyl) propanoic acid It is obtained in the same way as in example 1 (step d) by addition of thioacetic acid to 2-[(3,4-methylenedioxy phenyl) methyl] propenoic acid.

Yield=85%

IR (cm$^{-1}$): 1710, 1690

$^1$H NMR (CDCl$_3$/TMS): 9 (s, 1H), 6.6 (s, 3H), 5.8 (s, 2H), 3.2 to 2.4 (m, 5H), 2.2 (s, 3H).

B. Preparation of N-(RS)-[1-oxo-2-(acetylthiomethyl)-3-(2, 3-methylenedioxy phenyl) propyl]-benzyl glycinate The compound obtained in step A is coupled to benzyl glycinate according to the operating procedure of example 1 (step f).

Yield=68%

MP=60° C.

IR (Nujol): 3320, 1740, 1690, 1650 cm$^{-1}$ $^1$H NMR (CDCl$_3$/TMS): 7.2 (s, 5H), 6.8 (s, 3H), 6.3–6.0 (m, 1H), 5.8 (s, 2H), 5.1 (s, 2H), 3.95 (d, 2H, J=5 Hz), 3.2–2.4 (m, 5H), 2.2 (s, 3H).

$^{13}$C NMR (CDCl$_3$): 195.5, 172.9, 169.3, 146.9, 145.4, 134.9, 128.4, 122.9, 121.3, 120, 107, 100.3, 66.8, 46.3, 41.1, 32.1, 30.5, 30.2.

Microanalysis: C$_{22}$H$_{23}$NO$_6$S
Calc % C=61.52 H=5.39 N=3.26
Found % C=61.47 H=5.36 N=3.34

EXAMPLE 36

Preparation of N-(RS)-[1-oxo-2-(mercaptomethyl)-3-(2,3-methylenedioxy phenyl) propyl]-glycine Deprotection of the compound of example 35 is carried out according to the operating procedure of example 1 (step g).

Yield=71%
IR (CDCl$_3$): 3390, 1740, 1640 cm$^{-1}$
$^1$H NMR (CDCl$_3$/TMS): 9.4 (s, 1H), 6.8–6.4 (m, 4H), 5.8 (s, 2H), 4.0–3.8 (m, 2H), 3.1–2.3 (m, 5H), 1.65 (t, 1H, J=7.9 Hz).
$^{13}$C NMR (CDCl$_3$): 173.2, 171.85, 147, 145.5, 122.9, 121.45, 120, 107, 100.4. 50.3, 41.1, 32, 25.9.

Microanalysis: C$_{13}$H$_{15}$NO$_6$S
Calc % C=52.51 H=5.08 N=4.71
Found % C=52.38 H=4.87 N=4.51

EXAMPLE 37

Preparation of N-(RS)-[1-oxo-2-(acetylthiomethyl)-3-(4-phenoxy phenyl) propyl]-benzyl glycinate A. Preparation of (RS)-2-acetylthiomethyl-3-(4-phenoxy phenyl) propanoic acid It is obtained in the same way as in example 1 (step d) by addition of thioacetic acid to 2-[(4-phenoxy phenyl) methyl] propenoic acid.

Yield=98%
IR (film): 1700 cm$^{-1}$
$^1$H NMR (CDCl$_3$/TMS): 9.5–9.1 (m, 1H), 7.5–6.8 (m, 9H), 3.2–2.8 (m, 5H), 2.2 (s, 3H).

B. Preparation of N-(RS)-[1-oxo-2-(acetylthiomethyl)-3-(4-phenoxy phenyl) propyl]-benzyl glycinate The compound obtained in step A is coupled to benzyl glycinate according to the operating procedure of example 1 (step f).

Yield=52%
MP=66° C. (Microscope)
$^1$H NMR (CDCl$_3$/TMS): 7.2 (s, 5H), 7.2–6.7 (m, 9H), 5.8 (t, J=6.7 Hz, 1H), 5.0 (s, 2H), 4–3.8 (m, 2H), 3.1–2.4 (m, 5H), 2.2 (s, 3H).
IR (Nujol): 3300, 1730, 1680, 1640 cm$^{-1}$
Microanalysis: (C$_{27}$H$_{27}$NO$_5$S)
Calc % C=67.90 H
5.69 N=2.93
Found % C=67.59 H=5.55 N=3.03

EXAMPLE 38

Preparation of N-(RS)-[1-oxo-2-(mercaptomethyl)-3-(4-phenoxy phenyl) propyl]-glycine Deprotection of the compound obtained in step B of example 37 is carried out according to the operating procedure of example 1 (step g).

Yield=60%
MP=94° C. (Microscope)
$^1$H NMR (CDCl$_3$/TMS): 7.6–6.2 (m, 11H), 4.2–3.8 (m, 2H), 3.1–2.2 (m, 5H), 1.8–1.4 (m, 1H).
IR (Nujol): 3300, 1740, 1630 cm$^{-1}$
Microanalysis: (C$_{18}$H$_{19}$NO$_4$S)
Calc % C=62.58 H=5.54 N=4.05
Found 7, C=62.80 H=5.67 N=4.12

EXAMPLE 39

Preparation of N-(RS)-[1-oxo-2-(acetylthiomethyl)-3-(4-phenoxy phenyl) propyl)-(S)-benzyl alaninate The compound obtained in step A is coupled to (S) benzyl alaninate according to the operating procedure of example 1 (step f).

Yield=73% (50/50 mixture of the diastereomers)
IR (CDCl:$_3$): 3300, 1740, 1690, 1650 cm$^{-1}$
$^1$H NMR (CDCl$_3$/TMS): 7.2 (s, 5H), 7.2–6.7 (m, 9H), 6 (t, J=6.6 Hz, 1H), 5.1 (s, broad, 2H), 4.7–4.4 (m, 1H), 3.2–2.8 (m, 4H), 2.8–2.4 (m, 1H), 2.25 (s, 8H), 1.3 and 1.15 (2d, 3H, J=6.6 Hz).
$^{13}$C NMR (CDCl$_3$): 195.9, 195.6, 172.2, 157.4, 155.7, 135.2, 133.5, 130.2, 129.6, 128.5, 128, 122.9, 118.9, 118.5, 66.9, 49.5, 49.1, 47.7, 37.4, 30.9, 30.3, 18.3, 18.

Microanalysis: C$_{28}$H$_{29}$NO$_5$S
Calc % C=68.4 H=5.94 N=2.85
Found % C=68.15 H=6.06 N=3.15

EXAMPLE 40

Preparation of N-(RS)-[1-oxo-2-(mercaptomethyl)-3-(4-phenoxy phenyl) propyl]-(S)-alanine Deprotection of the compound of example 39 is carried out according to the operating procedure of example 1 (step g).

Yield=63% (50/50 mixture of the diastereomers)
IR (CDCl$_3$): 8420, 1720, 1650 cm$^{-1}$
$^1$H NMR (CDCl$_3$/TMS): 9.3 (s, 1H), 7.4–6.7 (m, 9H), 6.3 (t, J=8 Hz, 1H), 4.8–4.4 (m, 1H), 3.1–2.2 (m, 5H), 1.45 and 1.25 (2d, 3H, J=7.1 Hz).
$^{13}$C NMR (CDCl$_3$): 174.9, 173.1, 157.3, 155.7, 133.25, 130.1, 129.6, 123, 118.9, 118.5, 53.2, 52.75, 48.15, 47.9, 37.45, 37.1, 26, 25.8, 18.1, 17.8.

Microanalysis: C$_{19}$H$_{21}$NO$_4$S
Calc % C=63.48 H=5.88 N=3.89
Found % C=63.25 H=6.1 N=3.72

EXAMPLE 41

Preparation of N-(RS)-[1-oxo-2-(acetylthiomethyl)-3-(4-phenyl phenyl) propyl]-benzyl glycinate A. Preparation of (RS)-2-(acetylthiomethyl)-3-(4-phenyl phenylpropanoic acid It is obtained in the same way as in example 1 (step d) by addition of thioacetic acid to 2-[(4-phenyl phenyl) methyl] propenoic acid.

Yield=97%
IR (cm$^{-1}$): 1740, 1690
$^1$H NMR (CDCl$_3$/TMS): 9.6 (s, 1H), 7.7 to 7.1 (m, 9H), 3.2 to 2.8 (m, 5H), 2.25 (s, 3H).

B. Preparation of N-(RS)-[1-oxo-2-(acetylthiomethyl)-3-(4-phenyl phenyl) propyl)-benzyl glycinate The compound obtained in step A is coupled to benzyl glycinate according to the operating procedure of example 1 (step f).

Yield=64% (chromatographied)
MP=99–103° C. (Microscope)
IR (Nujol)=3290, 1745, 1690, 1650 cm$^{-1}$
$^1$H NMR (CDCl$_3$/TMS): 7.7 to 7.1 (m, 14H), 5.9 (m, 1H), 5.1 (s, 2H), 3.95 (m, 2H), 3.2 to 2.8 (m, 5H), 2.3 (s, 3H).
$^{13}$C NMR (CDCl$_3$): 196.1 (s), 173.3 (s), 169.6 (s), 140.9 (s), 139.6 (s), 137.8 (s), 135.2 (s), 129.4 (d), 128.7 (d), 128.3 (d), 127.3 (d), 127.0 (d), 66.9 (t), 48.9 (d), 41.1 (t), 37.7 (t), 30.9 (t), 30.3 (q).
Microanalysis: C$_{27}$H$_{27}$O$_4$NS
Calc % C=70.28 H=5.85 N=3.03
Found % C=70.10 H=6.01 N=3.03

EXAMPLE 42

Preparation of N-(RS)-[1-oxo-2-(mercaptomethyl)-3-(4-phenyl phenyl) propyl]-glycine Deprotection of the compound of example 41 is carried out according to the operating procedure of example 1 (step g).

Yield=78% (chromatographied)
MP=70°–73° C. (Microscope)
IR (Nujol)=1735, 1670 cm$^{-1}$
$^1$H NMR (CDCl$_3$-DMSO d$_6$/TMS): 7.9 to 7.2 (m, 9H), 6.0 (s, broad, 2H), 4.0 (d, 2H, J=6.8 Hz), 3.4 to 2.4 (m, 5H), 1.95 (s, broad, 1H).
$^{13}$C NMR (CDCl$_3$-DMSO d$_6$): 173.6 (s), 170.5 (s), 139.7 (s), 138.0 (s), 137.4 (s), 128.6 (d), 127.9 (d), 126.0 (d), 125.9 (d), 51.0 (d), 40.2 (t), 36.7 (t), 25.3 (t).
Microanalysis: C$_{18}$H$_{19}$O$_3$NS
Calc % C=65.65 N=4.25 H=5.77
Found % C=65.63 N=4.13 H=5.93

Splitting of 2-acetylthiomethyl-3-(4-phenyl phenyl) propanoic acid
A solution of 0.79 g (4.78 mmol) of (+) ephedrine in 25 ml of ether is added to a solution of 3 g (9.55 mmol) of 2-acetylthiomethyl-3-(4-phenyl phenyl) propanoic acid. The mixture is left for 41 hours, filtered, the crystals washed with ether and centrifuged.
Weight=2.15 g
MP=132°–142° C.
[α]$_D^{25}$=+14.5° (c=1.3, MeOH)

Recrystallizations
2.10 g of the (+) salt are placed in a flask and 17 ml of chloroform plus 28 ml of petroleum ether are added. After 22 hours, filtration is carried out, the salt is washed with ether and centrifuged.
Weight=1.38 g
Yield=66%
MP=138°–142° C. [α]$_D^{25}$=+11.6° (c=1.4, MeOH)
This process is repeated 4 times.
Overall yield of 5 recrystallizations=16%
MP=148° C.
[α]$_D^{25}$=+5.9° (c=1.1, MeOH)

Release of the optically pure (s) acid
0.33 g of optically pure (+) salt is dissolved in chloroform, water is added and the mixture acidified to pH=1 with a 3 N HCl aqueous solution. The organic phase is separated and extracted again with CHCl$_3$. The organic phases are combined, washed with water, dried on MgSO$_4$, filtered and concentrated.
Weight=0.22 g
Yield=100%
MP=121° C. [α]$_D^{25}$=–10.1° (c=1.3 in methanol)
IR (Nujol): 1710, 1690 cm$^{-1}$
$^1$H NMR (CDCl$_3$/TMS): 10.95 (s, 1H), 7.7 to 6.95 (m, 9H), 3.3 to 2.6 (m, 5H), 2.2 (s, 3H).
$^{13}$C NMR (CDCl$_3$): 195.1 (s), 179.5 (s), 140.5 (s), 139.4 (s), 136.4 (s), 129.2 (d), 128.5 (d), 127.0 (d), 126.8 (d), 47.7 (d), 36.9 (t), 30.3 (t), 29.5 (q).

EXAMPLE 43

Preparation of N-(S)-[1-oxo2-(acetylthiomethyl)-3-(4-phenyl phenyl) propyl)]-benzyl glycinate 2-acetylthiomethyl-3-(4-phenyl phenyl) propanoic acid in its (S) form is coupled to benzyl glycinate according to the operating procedure of example 1 (step f).

Yield=62% (recrystallized in ether)
MP=108°–109° C. (Microscope)
[α]$_D^{25}$=–6.7° (c=1.1 in CHCl$_3$)
IR (Nujol): 3300, 1730, 1680, 1645 cm$^{-1}$
$^1$H NMR (CDCl$_3$/TMS): 7.7, to 7.1 (m, 14H), 5.9 (t, 1H, J=4 Hz), 5.05 (s, 2H), 3.95 (dd, 1H, J=4 Hz), 3.9 (dd, 1H, J=4 Hz), 3.2 to 2.4 (m, 5H), 2.25 (s, 3H).
The $^{13}$C NMR spectrum is identical to that of the racemic product.
Microanalysis: C$_{27}$H$_{27}$O$_4$NS
Calc % C=70.28 N=3.03 H=5.85
Found % C=69.96 N=3.24 H=5.93

EXAMPLE 44

Preparation of N-(S)-[1-oxo-2-(acetylthiomethyl-3-(4-phenyl phenyl) propyl]-(S)-benzyl alaninate 2-acetylthiomethyl-3-(4-phenyl phenyl) propanoic acid in its (S) form is coupled to (S) benzyl alaninate according to the operating procedure of example 1 (step f).

Yield=67% (recrystallized in a CHCl$_3$/petroleum ether mixture)
MP=110° C., one diastereomer only (Microscope)
[α]$_D^{25}$=–11.7° (c=1.1 in CHCl$_3$)
IR (Nujol): 3320, 1725, 1680, 1640 cm$^{-1}$
$^1$H NMR (CDCl$_3$/TMS): 7.7 to 7.0 (m, 14H), 5.95 (d, 1H, J=6.8 Hz), 6.0 (s, 2H), 4.5 (quintuplet, 1H, J=6.8 Hz), 3.2 to 2.4 (m, 5H), 2.25 (s, 3H), 1.3 (d, 3H, J=6.8 Hz).
$^{13}$C NMR (CDCl$_3$): 195.7 (s), 172.3 (s), 171.9 (s), 140.5 (s), 139.2 (s), 137.5 (s), 135.0 (s), 129.2 (d), 128.5 (d), 128.3 (d), 128.2 (d), 127.7 (d), 126.9 (d), 126.7 (d), 66.8 (t), 49.2 (t), 47.7 (d), 38.0 (t), 31.1 (t), 30.3 (q), 17.9 (q).
Microanalysis: C$_{23}$H$_{29}$O$_4$NS
Calc % C=70.73 N=2.94 H=6.10
Found % C=70.33 N=2.97 H=6.10

EXAMPLE 45

Preparation of N-(S)-[1-oxo-2-(mercaptomethyl)-3-(4-phenyl phenyl) propyl]-(S)-alanine Deprotection of the compound of example 44 is carried out according to the operating procedure of example 1 (step g).

Yield=62% (chromatographied)
MP=131° C., one diastereomer only (Microscope)
[α]$_D^{25}$=+36.4° (c=1.0 in CHCl$_3$)IR(CHCl$_3$): 1720, 1675 cm$^{-1}$
$^1$H NMR (CDCl$_3$/TMS): 8.8 (s, 1H), 7.7 to 7.0 (m, 9H), 6.15 (d, 1H, J=8Hz), 4.5 (quintuplet, 1H, J=8 Hz), 3.2 to 2.3 (m, 5H), 1.5 (t, 1H, J=7.2 Hz), 1.35 (d, 3H, J=8 Hz).

$^{13}$C NMR (CDCl$_3$): 176.0 (s), 173.1 (s), 140.5 (s), 139.3 (s), 137.2 (s), 129.2 (d), 128.6 (d), 127.1 (d), 126.8 (d), 52.8 (d), 48.2 (d), 37.6 (t), 25.9 (t), 18.0 (q).

Microanalysis: C$_{19}$H$_{21}$O$_3$NS

Calc % C=66.47 N=4.08 H=6.12

Found % C=66.54 1 N=3.98 H=6.20

EXAMPLE 46

Preparation of N-(S)-[1-oxo-2-(acetylthiomethyl)-3-(4-phenyl phenyl) propyl]-(S)-benzyl]leucinate 2-acetylthiomethyl-3-(4-phenyl phenyl) propanoic acid in its (S) form is coupled to (S) benzyl leucinate according to the operating procedure of example 1 (step f).

Yield=42% (chromatographied)

MP=100° C., one diastereomer only (Microscope)

$[\alpha]_D^{25}$=−20.7° (c=1.1 in CHCl$_3$)

IR (Nujol): 3320, 1720, 1700, 1640 cm$^{-1}$ $^1$H NMR (CDCl$_3$/TMS): 7.8 to 7.0 (m, 14H), 5.9 (d, 1H, J=8 Hz), 4.95 (s, 2H), 4.75 to 4.35 (m, 1H), 3.2 to 2.4 (m, 5H), 2.2 (s, 3H), 1.75 to 1.3 (m, 3H), 0.8 (d, 6H, J=4 Hz).

$^{13}$C NMR (CDCl$_3$): 195.6 (s), 172.3 (s), 172.0 (s), 140.6 (s), 139.2 (s), 137.3 (s), 135.1 (s), 129.1 (d), 128.5 (d), 128.1 (d), 127.8 (d), 127.0 (d), 126.8 (d), 66.6 (t), 50.6 (d), 49.0 (d), 41.4 (t), 37.8 (t), 31.0 (t), 30.3 (q), 24.5 (d), 22.6 (q), 21.7 (q),

Microanalysis: C$_{31}$H$_{35}$O$_4$NS

Calc % C=71.95 N=2.70 H=6.76

Found % C=72.07 N=2.70 H=6.80

EXAMPLE 47

Preparation of N-[1-oxo-2-(mercaptomethyl)-3-(4-phenyl phenyl) propyl]-(S)-leucine Deprotection of the compound of example 46 is carried out according to the operating procedure of example 1 (step g).

Yield=71%

MP<50° C., one diastereomer only $[\alpha]_D^{25}$=+33.5° (c=1.1 in CHCl$_3$)

IR (Nujol): 3290, 1720, 1630 cm$^{-1}$ $^1$H NMR (CDCl$_3$/TMS): 10.2 (s, 1H), 7.7 to 7.0 (m, 9H), 6.0 (d, 1H, J=8.8 Hz), 4.75 to 4.35 (m, 1H), 3.2 to 2.3 (m, 5H), 1.9 to 1.3 (m, 3H), 1.55 (t, 1H, J=7.9 Hz), 0.8 (d, 6H, J=4 Hz).

$^{13}$C NMR (CDCl$_3$): 176.8 (s), 173.4 (s). 140.7 (s), 139.3 (s), 137.8 (s), 129.2 (d), 128.6 (d), 127.3 (d), 127.1 (d), 126.9 (d), 53.0 (d), 50.6 (d), 40.9 (t), 37.6 (t), 26.0 (t), 24.6 (d), 22.7 (q), 21.5 (q).

Microanalysis: C$_{22}$H$_{26}$O$_3$NS

Calc % C=68.75 N=3.64 H=6.77

Found % C=67.9 N=3.46 H=7.22

EXAMPLE 48

Preparation of N-(RS)-[1-oxo-2-(acetylthiomethyl)-3-(3-fluoro phenyl) propyl]-benzyl glycinate A. Preparation of (RS)-2-acetythiomethyl-3-(3-fluoro phenyl) propanoic acid It is obtained in the same way as in example 1 (step d) by the addition of thioacetic acid to 2-[(3-fluoro phenyl) methyl] propenoic acid.

Yield=98%

IR (film): 1700, 1610, 1590 cm$^{-1}$ $^1$H NMR (CDCl$_3$TMS): 11.25 (s, 1H), 7.45–6.75 (m, 4H), 3.3–2.6 (m, 5H), 2.3 (s, 3H).

B. Preparation of N-(RS)-[1-oxo-2-(acetylthiomethyl)-3-(3-fluoro phenyl) propyl]-benzyl glycinate The compound obtained in step A is coupled to benzyl glycinate according to the operating procedure of example 1 (step f).

Yield=83%

MP=60° C. (Microscope)

$^1$H NMR (CDCl$_3$/TMS): 7.35 (s, 5H), 7.3–6.7 (m, 4H), 6.05 (m, 1H), 5.10 (s, 2H), 3.95 (m, 2H), 3.25–2.55 (m, 5H), 2.3 (s, 3H).

$^{13}$C NMR (CDCl$_3$): 195.8, 172.8, 169.3, 162.8 (d, J=246.6 Hz), 141.1 (d, J=7.3 Hz), 135.1, 129.8 (d, J=7.3 Hz), 128.5, 124.5, 115.0 (d, J=46.5 Hz), 114.0 (d, J=46.5 Hz), 66.9, 48.7, 41.2, 37.7, 31.0, 30.3.

IR (Nujol): 3300, 1730, 1680, 1640 cm$^{-1}$

Microanalysis: (C$_{21}$H$_{22}$FNO$_4$S)

Calc % C=62.51 H=5.49 N=3.47

Found % C=62.70 H=5.35 N=3.64

EXAMPLE 49

Preparation of N-(RS)-[1-oxo-2-(mercaptomethyl)-3-(3-fluoro phenyl) propyl]-glycine Deprotection of the compound obtained in step B of example 48 is carried out according to the operating procedure of example 1 (step g).

Yield=79%

MP=125° C. (Microscope)

$^1$H NMR (CDCl$_3$-DMSOd$_6$/TMS): 7.65 (m, 1H), 7.45–6.65 (m, 4H), 6.3 (m, 1H), 3.90 (m, 2H), 3.2–2.3 (m, 5H), 1.75 (t, J=8.5 Hz, 1H).

$^{13}$C NMR (CDCl$_3$-DMSOd$_6$, 400 MHz): 172.9, 171.1, 162.5 (d, J$^1$=244 Hz), 141.2 (d, J$^3$=7.3 Hz), 129.5 (d, J$^3$=7.3 Hz), 124.4, 115.5 (d, J$^2$=22 Hz), 113.0 (d, J$^2$=22 Hz), 51.8, 40.9, 37.3, 25.8

IR (Nujol): 3380, 1745, 1620 cm$^{-1}$

Microanalysis: (C$_{12}$H$_{14}$O$_3$NFS)

Calc % C=53.13 H=5.20 N=5.16

Found % C=53.26 H=5.11 N=5.01

EXAMPLE 50

Preparation of N-(RS)-[1-oxo-2-(acetylthiomethyl)-3-(3-fluoro phenyl) propyl]-(S)-benzyl alaninate 2-acetylthiomethyl-3-(3-fluoro phenyl) propanoic acid in its racemic form is coupled to (S) benzyl alaninate according to the operating procedure of example 1 (step f).

Yield 90%

MP=52°–55° C. (Microscope) (50/50 mixture of the diastereomers)

$^1$H NMR (CDCl$_3$/TMS): 7.3 (s, 5H), 7.3–6.65 (m, 4H), 6.0 (m, 1H), 5.1 (s, 2H), 4.5 (quintuplet, J=7 Hz, 1H), 3.2–2.4 (m, 5H), 2.3 (s, 3H), 1.35 (t, J=7 Hz, 1, 5H), 1.15 (t, J=7 Hz, 1, 5H).

$^{13}$C NMR (CDCl$_3$): 195.5, 172.3, 171.8, 162.6 (d, J=244 Hz), 141.0, 135.0, 129.7 (d, J=9.7 Hz), 128.4, 128.1, 127.9, 124.5, 115.6 (d, J=21 Hz), 113.2 (d, J=21 Hz), 66.8, 50.5, 48.5, 47.9, 47.6, 37.8, 30.8, 30.2, 18.0, 17.8.

IR (Nujol): 3290, 1740, 1720, 1680, 1645 cm$^{-1}$

Microanalysis: ($C_{22}H_{24}FNO_4S$)
Calc % C=63.29 H=5.79 N=3.35
Found % C=63.52 H=5.90 N=3.40

EXAMPLE 51

Preparation of N-(RS)-[1-oxo-2-(mercaptomethyl)-3-(3-fluoro phenyl) propyl]-(S)-alanine Deprotection of the compound of example 50 is carried out according to the operating procedure of example 1 (step g).

Yield=71%

MP=120°–122° C. (Microscope) (50/50 mixture of the diastereomers)

$^1$H NMR (CDCl$_3$, DMSOd6/TMS): 7.55–6.4 (m, 6H), 4.4 (m, 1H), 3.15–2.3 (m, 5H), 1.65 (m, 1H), 1.4 (d, J=8 Hz, 1.5 H), 1.2 (d, J=8 Hz, 1.5H).

IR (Nujol): 3300, 2580, 1715, 1640 cm$^{-1}$

Microanalysis: ($C_{13}H_{16}FNO_3S$)
Calc % C=54.72 H=5.65 N=4.91
Found % C=54.57 H=5.44 N=4.82

EXAMPLE 52

Preparation of N-(RS)-[1-oxo-2-(acetylthiomethyl)-3-(3,4-difluoro phenyl) propyl]-benzyl glycinate A. Preparation of (RS)-2-acetythiomethyl-3-(3,4-difluoro phenyl) propanoic acid It is obtained in the same way as in example 1 (step d) by the addition of thioacetic acid to 2-[(3,4-difluoro phenyl) methyl] propenoic acid Yield=98%

IR (film): 1.700, 1610 cm$^{-1}$ $^1$H NMR (CDCl$_3$/TMS): 10.6 (s, 1H), 7.35–6.7 (m, 3H), 3.3–2.6 (m, 5H), 2.3 (s, 3H).

B. Preparation of N-(RS)-[1-oxo-2-(acetylthiomethyl) -3(3,4-difluoro phenyl) propyl]-benzyl glycinate The compound obtained in step A is coupled to benzyl glycinate according to the operating procedure of example 1 (step f).

Yield=87%

MP=78° C. (Microscope)

$^1$M NMR (CDCl$_3$/TMS): 7.3 (s, 5H), 7.25–6.75 (m, 3H) 6.0 (m, 1H), 5.15 (s, 2H), 4.0 (m, 2H), 3.2–2.55 (m, 5H), 2.3 (s, 3H).

$^{13}$C NMR (CDCl$_3$): 195.6, 172.6, 169.2, 149.6 (dd, J$^1$=247 HZ, J$^2$=12 Hz), 148.5 (dd, J$^1$=247 Hz, J$^2$=12 Hz), 135.4, 134.9, 128.4, 124.7, 11.7.5 (d, J$^2$=17 Hz), 116.9 (d, J$^2$=17 Hz), 66.8, 48.5, 40.9, 36.8, 30.9, 30.2.

IR (Nujol): 3300, 1740, 1680 cm$^{-1}$

Microanalysis; ($C_{21}H_{21}F_2NO_4S$)
Calc % C=59.85 H=5.02 N=3.32
Found % C=59.53 H=5.17 N=3.50

EXAMPLE 53

Preparation of N-(RS)-[1-oxo-2-(acetylthiomethyl)-3-(3,4-difluoro phenyl) propyl]glycine Deprotection of the compound obtained in step B of example 52 is carried out according to the operating procedure of example 1 (step g).

Yield=82%

MP=139° C. (Microscope)

$^1$H NMR (CDCl$_3$-DMSOd$_6$/TMS): 9.0 (s, 1H), 7.2–6.6 (m, 3H), 3.9 (d, J=6 Hz, 2H), 3.1–2.2 (m, 5H), 1.75 (t, J=8.5 Hz, 1H).

$^{13}$C NMR (CDCl$_3$/DMSOd$_6$, 400 HZ): 172.6, 171.0, 149.6 (dd, J$^1$=247 Hz, J$^2$=12 Hz), 148.5 (dd, J$^1$=247 Hz, J$^2$=12 Hz), 135.5, 124.6, 117.3 (d, J$^2$=16 Hz), 116.6 (d, J$^2$=16 Hz), 51.7, 40.7, 36.6, 25.8.

IR (Nujol): 3300, 1720, 1640 cm$^{-1}$

Microanalysis: ($C_{12}H_{13}F_2NO_3S$)
Calc % C=49.82 H=4.53 N=4.84
Found % C=49.70 H=4.34 N=4.63

EXAMPLE 54

Preparation of N-(RS)-[1-oxo-2-(acetylthiomethyl)-3-(3,4-difluoro phenyl) propyl]-(S)-benzyl alaninate 2-acetylthiomethyl-3-(3,4-difluoro phenyl) propanoic acid in its racemic form is coupled to (S) benzyl alaninate according to the operating procedure of example 1 (step f).

Yield=93%

MP=76°–79° C. (Microscope) (50/50 mixture of the diastereomers)

$^1$H NMR (CDCl$_3$/TMS): 7.3 (s, 5H), 7.2–6.7 (m, 3H), 6.1 (d, J=7 Hz, 1H), 5.1 (s, 2H), 4.5 (quintuplet, J=7 Hz, 1H), 3.1–2.4 (m, 5H), 2.3 (s, 3H), 1.3 (d, J=7 Hz, 1, 5H), 1.15 (d, J=7 Hz, 1, 5H).

$^{13}$C NMR (CDCl$_3$): 195.8, 172.3, 171.8, 149.8 (dd, J$^1$=247 Hz, J$^2$=17 Hz), 148.6 (dd, J$^1$=247 Hz, J$^2$=17 Hz), 135.6, 135.2, 128.5, 128.0, 124.9, 117.5 (d, J$^2$=17 Hz), 116.9 (d, J$^2$=17 Hz), 66.9, 49.1, 48.7, 47.9, 37.1, 31.0, 30.3, 18.1.

IR (Nujol): 3295, 1740, 1680, 1640 cm$^{-1}$

Microanalysis: ($C_{22}H_{23}F_2NO_4S$)
Calc % C=60.68 H=5.32 N=3.22
Found % C=61.02 H=5.23 N=3.27

EXAMPLE 55

Preparation of N-(RS)-[1-oxo-2-(mercaptomethyl)-3-(3,4-difluoro phenyl) propyl]-(S)-alanine Deprotection of the compound of example 54 is carried out according to the operating procedure of example 1 (step g).

Yield=72%

MP=103°–107° C. (Microscope) (50/50 mixture of the diastereomers)

$^1$H NMR (CDCl$_3$, DMSOd$_6$/TMS): 7.8 (s, 1H), 7.5–6.65 (m, 3H), 4.45 (quintuplet, J=8 Hz, 1H), 3.1–2.2 (m, 5H), 1.65 (m, 1H), 1.35 (d, J=8 Hz, 1, 5H), 1.2 (d, J=8 Hz, 1, 5H).

IR (Nujol): 3300, 2560, 1720, 1645 cm$^{-1}$

Microanalysis: ($C_{13}H_{15}F_2NO_3S$)
Calc % C=51.47 H=4.98 N=4.62
Found % C=51.33 H=4.87 N=4.46

EXAMPLE 56

Preparation of N-(RS)-[1-oxo-2-(acetylthiomethyl)-3-(3,5-difluoro phenyl) propyl]-benzyl glycinate A. Preparation of (RS)-2-acetythiomethyl-3-(3,5-difluoro phenyl) propanoic acid It is obtained in the same way as in example 1 (step d) by the addition of thioacetic acid to 2-[(3,5-difluoro phenyl) methyl]propenoic acid.

Yield=98%

IR (film): 1700, 1620, 1590 cm$^{-1}$ $^1$H NMR (CCl$_4$): 11.1 (s, 1H), 6.9–6.35 (m, 3H), 3.2–2.7 (m, 5H), 2.3 (s, 3H).

B. Preparation of N-(RS)-[1-oxo-2-(acetylthiomethyl)-3-(3,5-difluoro phenyl) propyl]-benzyl glycinate The compound obtained in step A is coupled to benzyl glycinate according to the operating procedure of example 1 (step f).

Yield=89%

MP=67° C. (Microscope)

$^1$H NMR (CCl$_4$): 7.25 (s, 5H), 6.85–6.40 (m, 3H), 6.2 (m, 1H), 5.05 (s, 2H), 3.85 (m, 2H), 3.2–2.4 (m, 5H), 2.15 (s, 3H).

$^{13}$C NMR (CDCl$_3$): 195.7, 172.4, 169.3, 162.6 (dd, J$^1$=249 Hz, J$^3$=12 Hz), 142.5, 135.1, 128.5, 128.3, 111.1 (d, J$^2$=24 Hz), 102.0 (t, J$^2$=24 Hz), 67.1, 48.5, 41.1, 37.5, 31.1, 30.3.

IR (Nujol): 3300, 1750, 1690, 1650, 1620, 1595 cm$^{-1}$

Microanalysis: (C$_{21}$H$_{21}$F$_2$NO$_4$S)

Calc % C=59.85 H=5.02 N=3.32

Found % C=60.0 H=5.14 N=3.33

EXAMPLE 57

Preparation of N-(RS)-[1-oxo-2-(mercaptomethyl)-3-(3,5-difluoro phenyl) propyl]-glycine Deprotection of the compound obtained in step B of example 56 is carried out according to the operating procedure of example 1 (step g).

Yield=69%

MP=85° C. (Microscope)

$^1$H NMR (CDCl$_3$, DMSOd$_6$/TMS): 7.3 (s, 1H), 6.9–6.35 (m, 3H), 3.9 (d, J=5 Hz, 2H), 3.15–2.2 (m, 5H), 1.75 (t, J=8.5 Hz, 1H).

$^{13}$C NMR (CDCl$_3$, DMSOd$_6$, 400 Hz): 172.5, 171.0, 162.4 (dd, J$^1$=248.3 Hz, J$^3$=12.5 Hz), 142.6, 111.4 (d, J$^2$=24 Hz), 101.4 (t, J$^2$=24 Hz), 51.4, 40.7, 37.2, 26.0.

IR (Nujol): 3290, 1720, 1640, 1620, 1595 cm$^{-1}$

Microanalysis: (C$_{12}$H$_{13}$F$_2$NO$_3$S)

Calc % C=49.82 H=4.53 N=4.84

Found % C=50.00 H=4.54 N=4.71

EXAMPLE 58

Preparation of N-(RS)-[1-oxo-2-(acetylthiomethyl)-3-(3,5-difluoro phenyl) propyl]-(S)-benzyl alaninate 2-acetylthiomethyl-3-(3,5-difluoro phenyl) propanoic acid in its racemic form is coupled to (S) benzyl alaninate according to the operating procedure of example 1 (step f).

Yield=96%

MP=64°–73° C. (Microscope) (50/50 mixture of the diastereomers)

$^1$H NMR (CDCl$_3$/TMS): 7.25 (s, 5H), 6.95–6.30 (m, 4H), 5.1 (S, 2H), 4.45 (quintuplet, J=7 Hz, 1H), 3.2–2.4 (m, 5H), 2.3 (s, 3H), 1.3 (d, J=7 Hz, 1.5H), 1.1 (d, J=7 Hz, 1.5H).

$^{13}$C NMR (CDCl$_3$): 195.8, 172.3, 171.5, 162.7 (dd, J$^1$=247 Hz, J$^3$=12 Hz), 142.8, 135, 128.4, 127.9, 111.6 (d, J$^2$=24 Hz), 101.8 (t, J$^2$=24 Hz), 66.8, 48.6, 47.7, 37.5, 31.0, 30.3, 18.

IR (Nujol): 3300, 1740, 1670, 1640, 1620, 1590 cm$^{-1}$

Microanalysis: (C$_{22}$H$_{23}$F$_2$NO$_4$S)

Calc % C=60.68 H=5.32 N=3.22

Found % C=60.93 H=5.26 N=3.29

EXAMPLE 59

Preparation of N-(RS)-[1-oxo-2-(mercaptomethyl)-3-(3,5-difluoro phenyl) propyl]-(S)-alanine Deprotection of the compound of example 58 is carried out according to the operating procedure of example 1 (step g).

Yield=62%

MP=115°–118° C. (Microscope) (50/50 mixture of the diastereomers)

$^1$H NMR (CDCl$_3$, DMSOd$_6$/TMS): 8.15 (s, 1H), 7.15–6.4 (m, 3H), 4.45 (quintuplet, J=7 Hz, 1H), 3.1–2.25 (m, 5H), 1.65 (m, 1H), 1.4 (d, J=7 Hz, 1.5H), 1.25 (d, J=7 Hz, 1.5H).

$^{13}$C NMR (CDCl$_3$/DMSOd$_6$): 174.5, 171.9, 163.2 (dd, J$^1$=249 Hz, J$^3$=12 Hz), 142.6, 111.6 (d, J$^2$=24.4 Hz, 101.9 (t, J$^2$=24.4 Hz), 52.6, 52.1, 47.8, 37.4, 26.3, 26.1, 18.15, 17.8.

IR (Nujol): 3300, 1715, 1640, 1620, 1595 cm$^{-1}$

Microanalysis: (C$_{13}$H$_{15}$F$_2$NO$_3$S)

Calc % C=51.47 H=4.98 N=4.62

Found % C=50.98 H=4.87 N=4.43

EXAMPLE 60

Preparation of N-(S)-[1-oxo-2-(acetylthiomethyl)-3-(3,5-difluoro phenyl) propyl]-(S)-benzyl alaninate ((−) isomer)

It is obtained by fractional recrystallization of the diastereomer mixture of example 58 in an ether/petroleum ether mixture.

[α]$_D^{25}$=−58.3° (c=1.2, MeOH)

MP=113° C. (Microscope)

$^1$H NMR (CDCl$_3$/TMS): 7.25 (s, 5H), 6.95–6.4 (m, 3H), 6.2 (m, 1H), 5.1 (s, 2H), 4.45 (quintuplet, J=7 Hz, 1H), 3.2–2.4 (m, 5H), 2.3 (s, 3H), 1.35 (d, J=7 Hz, 3H).

IR (Nujol): 3300, 1735, 1670, 1640, 1590 cm$^{-1}$

EXAMPLE 61

Preparation of N-(RS)-[1-oxo-2-(acetylthiomethyl)-3-(5'-indanyl) propyl]-benzyl glycinate A. Preparation of (RS)-2-acetylthiomethyl-3-(5'-indanyl) propenoic acid It is obtained in the same way as in example 1 (step d) by the addition of thioacetic acid to 2-[(5'-indanyl) methyl] propenoic acid.

Yield=96%

IR (cm$^{-1}$): 1700

$^1$H NMR (CCl$_4$/TMS): 11.2 (s, 1H), 7.2–6.8 (m, 3H), 3.2–2.4 (m, 9H), 2.2 (s, 3H), 2.2–1.8 (m, 2H).

B. Preparation of N-(RS)-[1-oxo-2-(acetylthiomethyl)-3-(5'-indanyl) propyl]-benzyl glycinate The compound obtained in step A is coupled to benzyl glycinate according to the operating procedure of example 1 (step f).

Yield=67%

MP=71°–72° C.

IR (Nujol): 3300, 1740, 1690, 1650 cm$^{-1}$ $^1$H NMR (CCl$_4$/TMS): 7.2 (s, 5H), 7.1–6.8 (m, 4H), 5 (s, 2H), 3.9–3.7 (m, 2H), 3.1–2.5 (m, 9H), 2.1 (s, 3H), 2.1–1.8 (m, 2H).

Microanalysis: ($C_{24}H_{27}NO_4S$)
Calc % C=67.73 H=6.39 N=3.79
Found % C=68.02 H=6.44 N=3.50

EXAMPLE 62

Preparation of N-(RS)-[1-oxo-2-(mercaptomethyl)-3-(5'-indanyl) propyl]-glycine

Deprotection of the compound obtained in step B of example 61 is carried out according to the operating procedure of example 1 (step g).
Yield=68%
MP : 90° C.
IR (Nujol): 3380, 1740, 1620 $cm^{-1}$
$^1H$ NMR ($CDCl_3$/TMS): 8 (s, 1H), 7.2–6.8 (m, 3H), 6.4–6.2 (m, 1H), 4.1–3.8 (m, 2H), 3.0–2.4 (m, 9H), 2.25–1.8 (m, 1H), 1.6 (t, 1H, J=7.8 Hz).
$^{13}C$ NMR ($CDCl_3$): 174.6, 172.6, 144.6, 142.5, 135.9, 126.5, 124.7, 124.2, 53.1, 41.2, 37.8, 32.6, 32.2, 25.8, 25.2.
Microanalysis: ($C_{15}H_{19}NO_3S$)
Calc % C=61.4 H=6.52 N=4.77
Found % C=61.35 H=6.50 N=4.82

EXAMPLE 63

Preparation of N-(RS)-[1-oxo-2-(acetylthiomethyl)-3-(5'-indanyl) propyl]-(S)-benzyl alaninate The compound obtained in step A of example 61 is coupled to (S) benzyl alaninate according to the operating procedure of example 1 (step f).
Yield=67%
IR: 3300, 1740, 1680, 1650 $cm^{-1}$
$^1H$ NMR ($CDCl_3$/TMS): 7.2 (s, 5H), 7.1–6.8 (m, 3H), 6.5 and 6.2 (2d, 1H, J=6.6 Hz), 5 (s, 2H), 4.7–4.3 (m, 1H), 3.2–2.5 (m, 9H), 2.2 (s, 3H), 2.1–1.8 (m, 2H), 1.3 and 1.1 (2d, 3H, J=6.7 Hz).
$^{13}C$ NMR ($CDCl_3$): 195.8, 172.2, 144.3, 142.2, 136.1, 135.2, 128.4, 128.1, 127.8, 126.4, 124.7, 124, 66.7, 49.3, 48.7, 47.9, 47.5, 38.2, 37.8, 32.3, 32.1, 30.9, 30.6, 30.2, 25.2, 18, 17.8.
Microanalysis: $C_{25}H_{29}NO_4S$
Calc % C=68.3 H=6.65 N=3.18
Found % C=68.1 H=6.60 N=3.05

EXAMPLE 64

Preparation of N-(RS)-[1-oxo-2-(mercaptomethyl)-3-(5°-indanyl) propyl]-(S)-alanine Deprotection of the compound of example 63 is carried out according to the operating procedure of example 1 (step g).
Yield=86%
MP=40°–45° C.
IR (Nujol): 3440, 1720, 1660 $cm^{-1}$
$^1H$ NMR ($CDCl_3$/TMS): 8.4 (s, 1H), 7.2–6.8 (m, 3H), 6.3–5.8 (m, 1H), 4.6–4.4 (m, 1H), 3.0–2.3 (m, 9H), 2.2–1.8 (m, 2H), 1.6 (t, 1H, J=9 Hz), 1.45 and 1.2 (2d, 3H, J=7.3 Hz).
$^{13}C$ NMR ($CDCl_3$): 175.6, 173.8, 144.5, 142.5, 135.9, 126.55, 124.9, 124.25, 53.5, 52.9, 48.1, 47.9, 38.1, 37.9, 32.5, 32.2, 25.9, 25.3, 17.9, 17.55.
Microanalysis: ($C_{16}H_{21}NO_3S$)

Calc % C=62.51 H=6.88 N=4.55
Found % C=62.30 H=6.81 N=4.38

EXAMPLE 65

Preparation of N-(RS)-[1-oxo-2-(acetylthiomethyl)-3-(2',3'-5-benzofuranyl) propyl]-benzyl glycinate A. Preparation of (RS)-2-(acetylthiomethyl)-3-(2',3'-dihydro-5'-benzofuranyl) propanoic acid It is obtained in the same way as in example 1 (step d) by the addition of thioacetic acid to 2-[(2',3'-dihydro-5'-benzofuranyl) methyl] propenoic acid.
Yield=98%
IR ($cm^{-1}$): 1700
$^1H$ NMR ($CDCl_3$/TMS): 10.2 (s, 1H), 7.1–6.8 (m, 2H), 6.65 (d, 1H, J=8.1 Hz), 4.5 (t, 2H, J=8 Hz), 3.3–2.4 (m, 7H), 2.2 (s, 3H).

B. Preparation of N-(RS)-[1-oxo-2-(acetylthiomethyl)-3-(2',3'-dihydro-5'benzofuranyl) propyl]-benzyl glycinate The compound obtained in step A is coupled to benzyl glycinate according to the operating procedure of example 1 (step f).
Yield=85%
MP=85° C.
IR (Nujol): 3800, 1720, 1680, 1635 $cm^{-1}$
$^1H$ NMR ($CDCl_3$/TMS): 7.2 (s, 5H), 7–6.75 (m, 2H), 6.65 (d, 1H, J=8 Hz), 6–5.8 (m, 1H), 5.1 (s, 2H), 4.5 (t, 2H, J=8.8 Hz), 3.9 (t, 2H, J=5 Hz), 3.3–2.4 (m, 7H), 2.2 (s, 3H).
Microanalysis: ($C_{23}H_{25}NO_6S$)
Calc % C=64.61 H=5.89 N=3.27
Found % C=64.60 H=5.87 N=3.36

EXAMPLE 66

Preparation of N-(RS)-[1-oxo-2-(mercaptomethyl)-3-(2',3'-dihydro-5'-benzofuranyl) propyl)]-glycine Deprotection of the compound obtained in step B of example 65 is carried out according to the operating procedure of example (step g).
Yield=70%
MP=121° C.
IR (Nujol): 3380, 1740, 1610 $cm^{-1}$
$^1H$ NMR ($CDCl_3$/TMS): 9.4 (s, 1H), 7.05–6.8 (m, 2H), 6.65 (d, 1H, J=8 Hz), 6.65–6.4 (m, 1H), 4.5 (t, 2H, J=8 Hz), 3.9 (t, 2H, J=5 Hz), 3.3–2.4 (m, 7H), 1.6 (t, 1H, J=8 Hz).
Microanalysis: ($CH_{14}H_{17}NO_4S$)
Calc % C=56.92 H=5.80 N=4.74
Found % C=56.84 H=5.70 N=4.51

EXAMPLE 67

Preparation of N-(RS)-[1-oxo-2-(acetylthiomethyl)-3-(2',3'-dihydro-5'-benzofuranyl) propyl)-(S)-benzyl alaninate The compound obtained in step A of example 65 is coupled to (S) benzyl alaninate according to the operating procedure of example 1 (step f).
Yield=66%
MP=63°–67° C.
IR (Nujol): 3280, 1720, 1680, 1640 $cm^{-1}$
$^1H$ NMR ($CDCl_3$/TMS): 7.2 (s, 5H), 7 to 6.7 (m, 2H), 6.6 (d, 1H, J=8 Hz), 6.2–5.7 (m, 1H), 5 (s, 2H), 4.6–4.3 (m, 3H), 3.3–2.4 (m, 7H), 2.2 (s, 3H), 1.3 and 1.1 (2d, 3H, J=8 Hz).

Microanalysis: $C_{24}H_{27}NO_5S$
Calc % C 65.28 H=6.16 N=3.17
Found % C=64.97 H=6.27 N=3.19

EXAMPLE 68

Preparation of N-(RS)-[1-oxo-2-(mercaptomethyl)-3-(2',3'-dihydro-5'-benzofuranyl) propyl]-(S)-alanine Deprotection of the compound of example 67 is carried out according to the operating procedure of example 1 (step g).

Yield=81%
MP=40°–45° C.
IR ($CDCl_3$): 3420, 1720, 1640 cm$^{-1}$
$^1$H NMR ($CDCl_3$/TMS): 8.8 (s, 1H), 7–6.75 (m, 1H), 6.65 (d, 1H, J=8 Hz), 6.3 (t, 1H, J=8 Hz), 4.7–4.3 (m, 1H), 4.5 (t, 2H, J=8 Hz), 3.3–2.4 (m, 7H), 1.6 (t, 1H, J=9 Hz), 1.4 and 1.2 (2d, 3H, J=6.7 Hz).
$^{13}$C NMR ($CDCl_3$): 175.6, 173.65, 158.9, 130.3, 128.3, 127.2, 125.35, 109.1, 70.95, 53.7, 53.2, 47.9, 37.6, 37.3, 29.4, 25,9, 25.7, 17.9, 17.5.

Microanalysis: ($C_{15}H_{19}NO_4S$)
Calc % C=58.23 H=6.19 N=4.52
Found % C=58.08 H=6.10 N=4.44

EXAMPLE 69

Preparation of N-(RS)-[1-oxo-2-(acetylthiomethyl)-3-(4-methoxy phenyl) propyl]-benzyl glycinate A. Preparation of N-(RS)-2-acetylthiomethyl-3-(4-methoxy phenyl) propanoic acid It is obtained in the same way as in example 1 (step d) by the addition of thioacetic acid to 2-[(4-methoxy phenyl) methyl] propenoic acid.

Yield=84%
IR: 1740–1685 cm$^{-1}$
$^1$H NMR ($CDCl_3$/TMS): 11.0 (s, 1H), 7.2 and 6.9 (AB, 4H, J=8 Hz), 3.8 (s, 3H), 3.3 to 2.8 (m, 5H), 2.3S (s, 3H).

B. Preparation of N-(RS)-[1-oxo-2-(acetylthiomethyl)-3-(4-methoxy phenyl) propyl]-benzyl glycinate The compound obtained in step A is coupled to benzyl glycinate according to the operating procedure of example 1 (step f).

Yield=68% (chromatographied)
MP=62°–64° C.
IR (Nujol)=3300, 1735, 1690, 1650 cm$^{-1}$
$^1$H NMR ($CDCl_3$/TMS): 7.4 (s, 5H), 7.15 and 6.8 (AB, 4H, J=9.3), 6.3 (t, broad, 1H), 5.15 (s, 2H), 4.1 to 3.85 (m, 2H)3.7 (s, 3H), 3.2 to 2.45 (m, 5H), 2.25 (s, 3H).
$^{13}$C NMR ($CDCl_3$): 195.4 (s), 173.0 (s), 169.0 (s), 157.9 (s), 134.7 (s), 130.1 (s), 129.5 (d), 128.1 (d), 113.5 (d), 66.6 (t), 54.7 (q), 48.6 (d), 40.9 (t), 37.0 (t), 30.6 (t), 30.2 (q).

Microanalysis: ($C_{22}H_{25}HO_5NS$)
Calc % C: 63.61 N: 3.37 H: 6.02
Found % C: 63.80 N: 3.53 H: 6.12

EXAMPLE 70

Preparation of N-(RS)-[1-oxo-2-(mercaptomethyl)-3-(4-methoxy phenyl) propyl]-glycine Deprotection of the compound obtained in step B of example 69 is carried out according to the operating procedure of example 1 (step g).

Yield=85%
MP=122°–123° C.
IR (Nujol): 3390, 1750, 1620 cm$^{-1}$
$^1$H NMR (DMSO $D_6$): 8.0 (m, 1H), 6.8 and 6.6 (AB, 4H, J=9.3), 3.4 (m, 5H), 2.6 to 1.8 (m, 6H).
$^{13}$C NMR (DMSO $D_6$): 174.3 (s), 172.4 (s), 158.8 (s), 132.1 (s), 131.0 (d), 114.8 (d), 56.1 (q), 52.0 (d), 41.7 (t), 37.5 (t), 26.6 (t).

Microanalysis: $C_{13}H_{17}O_4NS$)
Calc % C: 55.12 N: 4.94 H: 6.00
Found % C: 54.78 N 4.85 H: 5.95

EXAMPLE 71

Preparation of N-(RS)-[1-oxo-2-(acetylthiomethyl)-3-(4-methoxy phenyl) propyl]-(S)-benzyl alaninate (RS)-2-(acetythiomethyl)-S-(4-methoxy phenyl) propanoic acid is coupled to (S) benzyl alaninate according to the operating procedure of example 1 (step f).

Yield=50% (chromatographied)
MP=50°–51° C.
IR (Nujol): 3320, 1740, 1690 to 1645 cm$^{-1}$
$^1$H NMR ($CDCl_3$/TMS): 7.25 (s, 5H), 7.1 to 6.75 (AB, 4H, J=8 Hz), 6.3 and 6.15 (2 doublets, J=7.2 Hz), 5.05 (s, 2H), 4.5 (quintuplet, 1H, J=7.2 Hz), 3.6 (s, 3H), 3.15 to 2.4 (m, 5H), 2.2 (s, 3H), 1.3 and 1.1 (2 doublets, 3H, J=7.2 Hz).
$^{13}$C NMR ($CDCl_3$): 195.2 (s), 17.0 (s), 157.8 (s), 135.0 (s), 130.2 (s), 129.5 (d), 128.1 (d), 127.9 (d), 127.6 (d), 113.4 (d), 66.5 (t), 54.7 (q), 48.9 (d), 48.4 (d), 47.7 (d), 47.4 (d), 37.3 (t), 30.6 (t), 30.1 (q), 17.8 (q).

Microanalysis: ($C_{23}H_{27}O_5NS$) $C_{23}H_{27}O_5NS$
Calc % C: 64.33 N: 3.26 H: 6.29
Found % C: 63.98 N: 3.30 H: 6.26

EXAMPLE 72

Preparation of N-(RS)-[1-oxo-2-(mercaptomethyl)-3-(4-methoxy phenyl) propyl]-(S)-alanine Deprotection of the compound of example 71 is carried out according to the operating procedure of example 1 (step g).

Yield=83% (chromatographied)
IR:3320, 1730, 1630 cm$^{-1}$
$^1$H NMR ($CDCl_3$/TMS): 9.7 (s, 1H), 7.05 and 6.75 (AB, 4H, J=8 Hz), 6.55 and 6.4 (2 doublets, 1H, J=7.6 Hz), 4.5 (2 quintuplets, 1H, J=7.6 Hz), 3.7 (s, 3H), 3.1 to 2.2 (m, 5H), 1.6 (t, 1H, J=8 Hz), 1.4 and 1.2 (2 doublets, 3H, J=7.6 Hz).
$^{13}$C NMR ($CDCl_3$): 173.6 (s), 158.1 (s), 155.5 (s), 130.3 (s), 129.7 (d), 113.8 (d), 55.1 (q), 53.5 (d), 53.0 (d), 48.1 (d), 37.3 (t), 37.0 (t), 26.0 (t), 25.7 (t), 17.9 (q), 17.6 (q).

Microanalysis: ($C_{14}H_{19}O_4NS$)
Calc % C: 56.56 N: 4.71 H: 6.39
Found % C: 56.21 N: 4.57 H: 6.22

Splitting of 2-acetylthiomethyl-3-(4-methoxy phenyl) propanoic acid 3.05 5 of (−) ephedrine in solution in 25 ml of ether are added to 10 g of 2-acetylthiomethyl 3-(4-methoxy phenyl) propanoic acid in solution in 60 ml of ether. The mixture is left for seven days then filtered.

Weight obtained=6.1 g
MP=126° C.
$[\alpha]_D^{25}$=23.3°

Recrystallizations 6 g of the (−) salt are placed in a flask and 25 ml of chloroform plus 35 ml of ether are added. The mixture is left for 15 hours then filtered. This process is repeated three times.

Weight obtained=4.35 g
Overall yield of the four recrystallizations=73%
MP=122° C.
$[\alpha]_D^{25}$=−40.7 (C=1.2, MeOH)
Release of the optically pure (S) acid
An experimental process similar to that described in example 2 (II) is employed.
Yield=98% $[\alpha]^{25}$=−14.7° (C=1.3, MeOH)

EXAMPLE 73

Preparation of N-(S)-[1-oxo-2-(acetylthiomethyl)-3-(4-methoxy phenyl) propyl]-benzyl glycinate 2-acetylthiomethyl-3-(4-methoxy phenyl) propanoic acid in its (S) form is coupled to benzyl glycinate according to the operating procedure of example 1 (step f).

Yield=90% (chromatographied)
MP=84° C.
$[\alpha]_D^{25}$=−14.7° (c=1.3 in methanol)
Microanalysis: ($C_{22}H_{25}O_5NS$)
Calc % C: 63.61 N: 3.37 H: 6.02
Found % C: 63.43 N: 3.50 H: 6.05

EXAMPLE 74

Preparation of N-(S)-[1-oxo-2-(mercaptomethyl)-3-(4-methoxy phenyl) propyl]-glycine Deprotection of the compound obtained in example 73 is carried out according to the operating procedure of example 1 (step g).

Yield=84% (chromatographied)
$[\alpha]_D^{25}$=+50.5° (c=1.05 in methanol)
Microanalysis: ($C_{13}H_{17}O_4NS$)
Calc % C: 55.12 N: 4.94 H: 6.00
Found % C: 55.04 N: 4.76 H: 6.13

EXAMPLE 75

Preparation of N-(S)-[1-oxo-2-(acetylthiomethyl)-3-(4-methoxy phenyl) propyl]-(S)-benzyl alaninate 2-acetylthiomethyl-3-(4-methoxy phenyl) propanoic acid in its (S) form is coupled "to (S) benzyl alaninate according to the operating procedure of example 1 (step f).

Yield=56% (recrystallized in a chloroform/petroleum ether mixture)
MP=74° C.
$[\alpha]_D^{25}$=−47.1° (c=1.2 in methanol)
IR (Nujol): 3310, 1730, 1680, 1640 cm$^{-1}$
$^1$H NMR (CDCl$_3$/TMS): 7.3 (s, 5H), 7.05 and 6.75 (AB, 4H, J=8 Hz), 6.1 (d, 1H, J=7.2 Hz), 5.05 (s, 2H), 4.5 (quintuplet, 1H, J=7.2 Hz), 3.7 (s, 3H), 3.2 to 2.4 (m, 5H), 2.2 (s, 3H), 1.3 (d, 3H, J=7.2 Hz).
$^{13}$C NMR (CDCl$_3$): 195.5 (s), 172.1, (s), 157.9 (s), 135.0 (s), 130.3 (s), 129.6 (d), 128.1 (d), 127.7 (d), 113.5 (d), 66.6 (t), 54.8 (q), 49.1 (d), 47.5 (d), 37.4 (t), 30.8 (t), 30.2 (g), 17.8 (g)
Microanalysis: ($C_{23}H_{27}O_5NS$)

Calc % C: 64.33 N: 3.26 H: 6.29
Found % C: 64.03 N: 3.18 H: 6.50

EXAMPLE 76

Preparation of N-(S)-[1-oxo-2-(mercaptomethyl)-3-(4-methoxy phenyl) propyl]-(S)-alanine Deprotection of the compound obtained in example 75 is carried out according to the operating procedure of example 1 (step g).

Yield=83% (chromatographied)
$[\alpha]_D^{25}$=−5.8° (c=1.2 in methanol)
IR: 3290 to 3390, 1730, 1645 cm$^{-1}$
$^1$H NMR (CDCl$_3$/TMS): 9.85 (s, 1H), 7.05 and 6.8 (AB, 4H, J=8 Hz), 6.3 (d, 1H, J=7.3 Hz), 4.5 (quintuplet, 1H, J=7.3 Hz), 3.7 (s, 3H), 3.15 to 2.25 (m, 5H), 1.7 to 1.15 (m, 1H), 1.4 (d, 3H, J=7.3 Hz).
$^{13}$C NMR (CDCl$_3$): 176.1 (s), 173.6 (s), 158. 2 (s), 130.2 (s), 129.7 (d), 113.9 (d), 55.1 (q), 53.0 (d), 48.2 (d), 37.1 (t), 25.7 (t), 18.0 (q).
Microanalysis: $C_{14}H_{19}O_4NS$
Calc % C: 56,56 N: 4.71 H: 6.39
Found % C: 56.45 N: 4.70 H: 6.28

EXAMPLE 77

Preparation of N-(RS)-[1-oxo-2-(acetylthiomethyl)-3-(4-ethoxy phenyl) propyl]-benzyl glycinate A. Preparation of (RS)-2-acetylthiomethyl-3-(4-ethoxy phenyl propanoic acid It is obtained in the same way as in example 1 (step d) by the addition of thioacetic acid to 2-[(4-ethoxy phenyl)-methyl]propenoic acid.

Yield=95%
$^1$H NMR (CDCl$_3$/TKS): 9.6 (s, 1H), 7.15 and 6.8 (AB, 4H, J=9.3 Hz), 4.0 (9, 2H, J=6.6 Hz), 3.25 to 2.7 (m, 5H), 2.3 (s, 3H), 1.4 (t, 3H, J=6.6 Hz).

B. Preparation of N-(RS)-[1-oxo-2-(acetylthiomethyl)-3-(4-ethoxy phenyl) propyl]-benzyl glycinate The compound obtained in step A is coupled to benzyl glycinate according to the operating procedure of example 1 (step f).

Yield=82% (chromatographied)
MP=78° C.
IR: 3800, 1730, 1690, 1640 cm$^{-1}$
$^1$H NMR (CDCl$_3$/TMS): 7.3 (s, 5H), 7.05 and 6.75 (AB, 4H, J=7.5 Hz), 5.85 (m, 1H), 5.1 (s, 2H), 4.3 to 3.6 (m, 4H), 3.2 to 2.8 (m, 5H), 2.25 (s, 3H), 1.3 (t, 3H, J=6.5 Hz).

EXAMPLE 78

Preparation of N-(RS)-[1-oxo-2-(mercaptomethyl)-3-(4-ethoxy phenyl) propyl]-glycine Deprotection of the compound obtained in example 77 is carried out according to the operating procedure of example 1 (step g).

Yield=82%
MP=124° C.
IR: 3380, 2560, 1745, 1620 cm$^{-1}$
$^1$H NMR (DMSO/TMS): 7.8 (d, 1H, J=4.7 Hz), 7.1 and 6.75 (AB, 4H, J=7.5 Hz), 4.2 to 3.5 (m, 4H), 3.1 to 2.2 (m, 5H), 1.8 (t, 1H, J=6.7 Hz), 1.3 (t, 3H, J=6.7 Hz).

EXAMPLE 79

Preparation of N-(RS)-[1-oxo-2-(acetylthiomethyl)-3-(4-ethoxy phenyl) propyl]-(S)-benzyl alaninate 2-acetylthiomethyl-3-(4-ethoxy phenyl) propanoic acid is coupled to (S) benzyl alaninate according to the operating procedure of example 1 (step f).

Yield=75% (chromatographied)

MP=52° C.

IR: 3280, 1725, 1675, 1640 cm$^{-1}$ $^1$H NMR (CDCl$_3$/TMS): 7.15 (s, 5H), 7.05 and 6.75 (AB, 4H, J=7.5 Hz), 6.2 to 5.8 (m, 1H), 5.1 (s, 2H), 4.5 (quintuplet, 1H, J=7 Hz), 3.95 (q, 2H, J=6 Hz), 3.2 to 2.3 (m, 5H), 2.25 (s, 3H), 1.3 (t, 3H, J=6 Hz), 1.3 and 1.1 (d, 3H, J=7 Hz).

EXAMPLE 80

Preparation of N-(RS)-[1'-oxo-2-(mercaptomethyl)-3-(4-ethoxy phenyl) propyl]-(S)-alanine Deprotection of the compound obtained in example 79 is carried out according to the operating procedure of example 1 (step g).

Yield=52%

IR: 3300, 1720, 1635 cm$^{-1}$ $^1$H NMR (CDCl$_3$/TMS): 10.4 (s, 1H), 7.05 and 6.75 (AB, 4H, J=8 Hz), 6.6 to 6.15 (m, 1H), 4.55 (quintuplet, 1H, J=6 Hz), 3.9 (q, 2H, J=6.7 Hz), 3.1 to 2.2 (m, 5H), 1.6 (t, 1H, J=7.5 Hz), 1.6 to 1.0 (m, 6H).

EXAMPLE 81

Preparation of N-(E)-[1-oxo-2-(acetylthiomethyl)-2-ene-3-phenyl propyl]-(S)-benzyl alaninate A. Preparation of (Z)-2-bromomethyl cinnamic acid A mixture of 2 g (12.34 mmol) of (E) 2-methyl cinnamic acid, 2.19 g (12.34 mmol) of N-bromosuccinimide (NBS) and a catalytic amount of benzoyl peroxide in 6 ml of CCl$_4$ are heated under reflux for hours. The residue is filtered and washed with ether. The organic phase is successively washed with a 1N HCl aqueous solution then with water. It is dried on MgSO$_4$, filtered and evaporated to dryness.

Yield=57% (recrystallized in ether)

MP=168° C.

IR (Nujol): 1665 cm$^{-1}$ $^1$H NMR (CDCl$_3$/TMS): 10.0 (s, 1H), 7.9 (s, 1H), 7.8 to 7.2 (m, 5H), 4.0 (s, 2H).

B. Preparation of (Z) 2-acetylthiomethyl cinnamic acid 2.1 g of the acid obtained previously (8.70 mmol), 0.73 g (8.70 mmol) of NaNCO$_3$ and 3 ml of water are mixed together. A solution of 0.67 g (8.8 mmol) of thioacetic acid and 1.44 g (10.43 mmol) of K$_2$CO$_3$ in 21 ml of water are then added at 0° C. The mixture is stirred for 15 hours at 20° C. It is then acidified with a 6N HCl aqueous solution. It is extracted twice with ether. The combined ethereal phases are washed with water, dried on MgSO$_4$, filtered and concentrated.

Yield=67% (recrystallized in ether)

MP=114° C.

IR (Nujol): 1670 cm$^{-1}$ $^1$H NMR (CDCl$_3$/TMS): 9.55 (s, 1H), 8.0 (s, 1H), 7.5 (s, 5H), 4.1 (s, 2H), 2.3 (s, 3H).

C. Preparation of (E) 2-acetylthiomethyl cinnamic acid 2 g of the previous (Z) acid in solution in 30 ml of ethanol are irradiated for 16 hours with a Hanovia TQ 150 lamp. After evaporation, a Z/E 60/40 mixture of the acid is obtained. This mixture is taken up with 25 ml of ether and a solution of 0.39 g of cyclohexylamine (0.4 eq.) in 5 ml of ether are added to it. After 30 minutes of continuous stirring, the solution is filtered. The salt is recovered and treated with a 3N HCl aqueous solution. It is extracted with ether. The organic phase is washed with a saturated NaCl aqueous solution, dried on MgSO$_4$, filtered and concentrated.

Yield=32%

MP=57° C.

$^1$H NMR (CDCl$_3$/TMS): 9.6 (s, 1H), 7.3 (s, 5H), 7.2 (s, 1H), 3.85 (s, 2H), 2.25 (s, 3H).

D. Preparation of N-(E)-[1-oxo-2-(acetylthiomethyl)-2-ene-3-phenyl propyl]-(S)-benzyl alaninate (E) 2-acetylthiomethyl cinnamic acid obtained in step C is coupled to (S) benzyl alaninate according to the operating procedure of example 1 (step f).

Yield=83% (chromatographied)

MP=103° C. [α]$_D^{20}$=–25.2° (c=1.8, CHCl$_3$)

IR (Nujol): 3280, 1730, 1690, 1630 cm$^{-1}$ $^1$H NMR (CDCl$_3$/TMS); 7.3, (s, 5H), 7.25 (s, 5H), 6.9 (s, 1H), 6.05 (d, 1H, J=6.6 Hz), 4.6 (m, 1H), 3.85 (s, 2H), 2.3 (s, 2H), 1.2 (d, 3H, J=6.6 Hz).

Microanalysis: (C$_{22}$H$_{23}$O$_4$NS)

Calc % C=66.36 H=5.83 N=3.52

Found % C=66.36 H=5.68 1N=3.53

EXAMPLE 82

Preparation of N-(E)-[1-oxo-2-(mercaptomethyl)-2-ene-3-phenyl propyl]-(S)-alanine 3.4 mmol of LiOH (4 sq.) are added, at 0° C. and under an argon atmosphere, to a solution of 0.85 mmol of the diester obtained in step D of example 81 in solution in a THF-H$_2$O mixture (75–25) and the mixture is stirred for 2 hours. The THF is evaporated, the aqueous phase is washed with ether and acidified with a 3N HCl aqueous solution. It is extracted with ether, washed with a saturated NaCl aqueous solution, dried on MgSO$_4$, filtered and evaporated.

Yield=60% (chromatographied)

MP=78° C.

IR (Nujol): 3300, 1720, 1650, 1610 cm$^{-1}$ $^1$H NMR (CDCl$_3$/TMS): 9.15 (s, 1H), 7.25 (s, 5H), 6.70 (s, 1H), 6.25 (d, 1H, J=6.6 Hz), 4.55 (m, 1H), 3.5 (d, 2H, J=8 Hz), 1.8 (t, 1H, J=8 Hz), 1.25 (d, 3H, J=6.6 Hz).

Microanalysis: (C$_{13}$H$_{15}$O$_3$NS)

Calc % C=58.84 H=5.69 N=5.28

Found % C=58.86 H=5.83 N=5.14

EXAMPLE 83

Preparation of N-(E)-[1-oxo-2-(acetylthiomethyl)-2-ene-3-phenyl propyl]-(S)-benzyl norvalinate (E) 2-acetylthiomethyl cinnamic acid obtained in step C of example 81 is coupled to (S) benzyl norvalinate according to the operating procedure of example 1 (step f).

Yield=83% (chromatographied)

MP=80° C.

[α]$_D^{20}$=–26.4° (c=1.53, CHCl$_3$)

IR (Nujol): 3300, 1720, 1680, 1640, 1620 cm$^{-1}$ $^1$H NMR (CDCl$_3$/TMS): 7.3 (s, 5H), 7.25 (s, 5H), 6.85 (s, 1H), 6 (d, 1H, J=7.6 Hz), 5.1 (s, 2H), 4.8 to 4.4 (m, 1H), 3.85 (s, 2H), 2.3 (s, 3H), 1.85 to 0.6 (m, 7H).

Microanalysis: C$_{24}$H$_{27}$O$_4$NS

Calc % C=67.73 H=6.39 N=3.29

Found % C=67.71 H=6.35 N=3.38

EXAMPLE 84

Preparation of N-(E)-[1-oxo-2-(acetylthiomethyl)-2-ene-3-phenyl propyl]-(S)-benzyl norleucinate (E) 2-acetylthiomethyl cinnamic acid (example 81 C) is coupled to (S) benzyl norleucinate according to the operating procedure of example 1 (step f).

Yield=79%
MP=79° C.
[α]$_D^{20}$=22.1° (c=1.5, CHCl$_3$)
IR (Nujol): 3280, 1720, 1670, 1640, 1620 cm$^{-1}$
$^1$H NMR (CDCl$_3$/TMS): 7.3 (s, 5H), 7.25 (s, 5H), 6.85 (s, 1H), 6.0 (d, 1H, J=7.4 Hz), 5.1 (s, 2H), 4.8 to 4.45 (m, 1H), 3.85 (s, 2H), 2.3 (s, 3H), 1.8 to 0.6 (m, 9H).
Microanalysis: C$_{25}$H$_{29}$O$_4$NS
Calc % C=68.30 H=6.65 N=3.18
Found % C=67.67 H=6.47 N=3.43

EXAMPLE 85

Preparation of N-(E)-[1-oxo-2-(acetylthiomethyl)-2-ene-3-phenyl propyl]-(RS)-3-(3,4-methylenedioxy phenyl)-methyl alaninate (E) 2-acetylthiomethyl cinnamic acid (example 81C) is coupled to (RS)-3-(3,4-methylenedioxy phenyl) methyl alaninate according to the operating procedure of example 1 (step f).
Yield=48%
MP=75° C.
IR (Nujol): 3250, 1740, 1690, 1640 cm$^{-1}$
Microanalysis: C$_{23}$H$_{25}$O$_4$NS
Calc % C=62.57 H=5.25 N=3.17
Found % C=62.28 H=5.07 N=3.44
$^1$H NMR (CDCl$_3$/TMS): 7.25, (s, 5H), 6.8 (s, 1H), 6.75 to 6.15 (m, 3H), 6.15 to 5.8 (m, 1H), 5.85 (s, 2H), 5.0 to 4.6 (m, 1H), 3.85 (s, 2H), 3.6 (s, 3H), 2.9 (d, 2H, J=7.6 Hz), 2.3 (s, 3H).

EXAMPLE 86

Preparation of N-(E)-[1-oxo-2-(mercaptomethyl)-2-ene-3-phenyl propyl]-(R,S)-3-(3,4-methylenedioxy phenyl)-alanine It is obtained by deprotection of the compound of example 85 according to the operating procedure of example 82.
Yield=75%
MP=50° C.
IR (Nujol): 3400, 1720, 1620 to 1600 cm$^{-1}$
$^1$H NMR (CDCl$_3$/TMS): 8.3 (m, 1H), 7.25 (s, 5H), 6.7 (s, 1H), 6.55 to 6.0 (m, 4H), 5.85 (s, 2H), 5.0 to 4.65 (m, 1H), 3.45 (d, 2H, J=8.2 Hz), 2.9 (d, 2H, J=5.1 Hz), 1.75 (t, 1H, J=8.2 Hz).
Microanalysis: C$_{20}$H$_{19}$O$_6$NS
Calc % C=62.32 H=4.96 N=3.63
Found % C=62.18 H=5.06 N=3.39

EXAMPLE 87

Preparation of N-(Z)-[1-oxo-2-(acetylthiomethyl)-2-ene-3-(3,4-methylenedioxy phenyl) propyl]-benzyl glycinate A. Preparation of (Z) 2-bromomethyl-3-(3,4-methylenedioxy phenyl) propenoic acid
(E) 2-methyl-3-(3,4-methylenedioxy phenyl) propenoic acid (prepared by a PERKIN reaction using piperonal) is substituted with N-bromosuccinimide in chloroform according to the operating procedure described in example 81 A.
Yield=75%
MP=158° C.
$^1$H NMR (CDCl$_3$/TMS): 8.6 (s, 1H), 7.7 (s, 1H), 7.3 to 6.7 (m, 3H), 6.0 (s, 2H), 4.35 (s, 2H).

B. Preparation of (Z) 2-acetylthiomethyl-3-(3,4-methylenedioxy phenyl) propenoic acid A solution of 1.26 g of thioacetic acid (1.05 eq.) and 2.12 g of diisopropylethylamine (1.05 eq.) in 80 ml of THF are added at 0° C. to a solution of 4.47 g of the acid prepared in step A in solution in 80 ml of THF. The mixture is stirred at 0° C. for 30 minutes. The THF is evaporated and the residue taken up with 100 ml of ether. It is washed with a 1N HCl aqueous solution. The organic phase is dried on MgSO$_4$, filtered and concentrated.
Weight obtained=4 g
Yield=86%
MP=142° C.
$^1$H NMR (CDCl$_3$/TMS): 8.6 (s, 1H) 7.8 (s, 1H), 7.1 to 6.7 (m, 3H), 6.0 (s, 2H), 4.05 (s, 2H), 2.3 (s, 3H).

C. Preparation of N-(Z)-[1-oxo-2-(acetylthiomethyl)-2-ene-3-(3,4-methylenedioxy phenyl) propyl]-benzyl glycinate (Z) 2-acetylthiomethyl-3-(3,4-methylenedioxy phenyl) propenoic acid obtained in step B is coupled to benzyl glycinate according to the operating procedure described in example 1 (step f).
Yield=55%
MP=102° C.
$^1$H NMR (CDCl$_3$/TMS): 7.5 (s, 1H), 7.3 (s, 5H), 7.0 to 6.7 (m, 3H), 5.95 (s, 2H), 5.15 (s, 2H), 4.15 (d, 2H, J=5.2 Hz), 4.0 (s, 2H), 2.3 (s, 3H).

EXAMPLE 88

Preparation of N-(Z)-[1-oxo-2-(mercaptomethyl)-2-ene3-(3,4-methylenedioxy phenyl) propyl]-glycine Deprotection of the compound obtained in example 87 is carried out according to the operating procedure described in example 82.
Yield=75%
MP=91° C.
$^1$H NMR (DMSO/TMS): 7.20 (s, 1H), 7.0 to 6.7 (m, 3H), 6.0 (s, 2H), 4.10 (d, 2H, J=4.5 Hz), 3.65 (d, 2H, J=7 Hz), 2.0 (t, 1H, J=7 Hz).

EXAMPLE 89

Preparation of N-(E)-[1-oxo-2-(acetylthiomethyl)-2-ene-3-(3,4-methylenedioxy phenyl) propyl]-benzyl glycinate A. Preparation of (E) 2-acetylthiomethyl-3-(3,4-methylenedioxy phenyl) propenoic acid (Z) 2-acetylthiomethyl-3-(3,4-methylenedioxy phenyl) propenoic acid prepared in example 87 (step B) is irradiated according to the operating procedure described in example 81 (step C).
Yield=25%
$^1$H NMR (CDCl$_3$/TMS): 10.6 (s, 1H), 7.2 to 6.6 (m, 4H), 5.9 (s, 2H), 3.8 (s, 2H), 2.3 (s, 3H).

B. Preparation of N-(E)-[1-oxo-2-(acetylthiomethyl)-2,ene-3-(3,4-methylenedioxy phenyl) propyl]-benzyl glycinate
(E) 2-acetylthiomethyl-3-(3,4-methylenedioxy phenyl) propenoic acid obtained in step A is coupled to benzyl glycinate according to the operating procedure described in example 1 (step f).
Yield=58%
MP=113° C.
$^1$H NMR (CDCl$_3$/TMS): 7.3 (s, 5H), 7.0 to 6.65 (m, 4H), 6.15 (m, 1H), 5.9 (s, 2H), 5.15 (s, 2H), 4.05 (d, 2H, J=5 Hz), 3.8 (s, 2H), 2.3 (s, 3H).

EXAMPLE 90

Preparation of N-[N-(RS)-[1-tert-butoxycarbonyl-2-phenyl ethyl]-(S)-phenylalanyl]-benzyl glycinate A. Preparation of (RS)-2-hydroxy-3-phenyl propanoic acid A solution of 22.55 g (326.80 mmol) of sodium nitrite in solution in 90 ml of water is added, over a period of one hour at −5° C., to a solution of 15 g (90.80 mmol) of (S) phenylalanine in 230 ml of a 10% sulfuric acid aqueous solution. The solution is left to return to room temperature then the reaction medium is heated at 50° C. for 3 hours.

After returning to room temperature, the solution is extracted by 3 times 100 ml of ethyl acetate. The combined organic phases are washed with 50 ml of water and with 50 ml of a saturated sodium chloride aqueous solution. After drying on magnesium sulfate, filtration and evaporation, 9.25 g of a solid yellow residue are obtained. This solid is recrystallized in an ether/petroleum ether solvent system. 6.44 g of a white solid are obtained.

Yield=43%

Rf value: 0.55 (eluent: 70/30 benzene/acetic acid)

$^1$H NMR (acetone $D_6$/TMS): 7.2 (s, 5H), 7.2 to 5.4 (m, 1H), 4.55 to 4.3 (m, 1H), 3.35 to 2.7 (m, 3H).

B. Preparation of (RS)-2-acetyloxy3-phenyl propanoic acid 4.83 g (61.53 mmol) of acetyl chloride are added to 8.88 g (53.49 mmol) of (RS)-2-hydroxy-3-phenyl propanoic acid. The mixture is refluxed for 30 minutes. The excess acetyl chloride is evaporated. 11.18 g of (RS)-2-acetyloxy-3-phenyl propanoic acid are obtained.

Yield=98%

$^1$H NMR (CDCl$_3$/TMS): 11.0 (s, 1H), 7.2 (s, 5H), 5.25 (m, 1H), 3.4 to 2.8 (m, 2H), 2.0 (s, 3H).

C. Preparation of (RS)-2-acetyloxy-3-phenyl-tert.-butyl propanoate

A solution of 8.4 g (54.80 mmol) of phosphorous oxychloride in 12 ml of dichloromethane is added, at a temperature lower than 40° C., to a solution of 11.4 g (54.80 mmol) of the acid obtained in step B and 4.06 g (54.80 mmol) of tertiary butanol in solution in 27 ml of pyridine.

The mixture is cooled down to a temperature of 5° C., filtered and the precipitate washed with dichloromethane. The filtrate is successively washed with water, 2 times with a saturated NaHCO$_3$ aqueous solution, 2 times with a 1N HCl aqueous solution and 1 time with water. The organic phase is dried on MgSO$_4$, filtered and concentrated. 10.5 g of (RS)-2-acetyloxy-3-phenyl-tert.-butyl propanoate are obtained.

Yield=73%

$^1$H NMR (CDCl$_3$/TMS): 7.2 (s, 5H), 5.1 (t, 1H, J=5.3 Hz), 3.05 (d, 2H, J=5.3 Hz), 2.0 (s, 3H), 1.3 (s, 9H).

D. Preparation of (RS)-2-hydroxy-3-phenyl-tert.-butyl propanoate 9.25 g (35.03 mmol) of the product obtained in step C in solution in 60 ml of a methanol/H$_2$O mixture (70/30) are placed in a flask. The mixture is cooled down to 0° C. and 17.5 ml of a 1N NaOH aqueous solution are added. The solution is stirred for 1 hour.

The methanol is evaporated under vacuum and the aqueous phase is extracted 2 times with ether. The organic phases are combined, washed once with water, dried on MgSO$_4$, filtered and concentrated. 6.52 g of an oil are obtained, which is then chromatographied on silica (eluent: 10/90 ether/petroleum ether).

Weight obtained=5.98 g

Yield=77%

Rf value: 0.36 (25/75 ether/petroleum ether)

$^1$H NMR (CDCl$_3$/TMS): 7.2 (s, 5H), 4.3 (m, 1H), 3.1 to 2.75 (m, 3H), 1.35 (s, 9H).

E. Preparation of (RS)-2-hydroxy-3-phenyl-tert.-butyl propionate triflate 0.5 g (2.25 mmol) of (RS)-2-hydroxy-3-phenyl-tert.-butyl propanoate and 0.18 g (2.25 mmol) of pyridine in solution in 1 ml of CH$_2$Cl$_2$ are added, at a temperature of −20° C., to a solution of 0.73 g (2.61 mmol) of trifluoromethane sulfonyl anhydride in 3 ml of CH$_2$Cl$_2$. The solution is stirred for 30 minutes.

The reaction medium is taken up with water and CH$_2$Cl$_2$, the organic phase is washed with a 0.1N HCl aqueous solution then with a saturated NaHCO$_3$ aqueous solution and, finally, with water. The organic phase is dried on MgSO$_4$, filtered and concentrated. 0.7 g of (RS)-2-hydroxy-3-phenyl-tert.-butyl propionate filtrate are obtained.

Yield=89%

$^1$H NMR (CDCl$_3$/TMS): 7.25 (s, 5H), 5.1 (m, 1H), 3.2 (m, 2H), 1.4 (s, 9H).

F. Preparation of N-(RS)-(1-tert.-butoxycarbonyl-2-phenyl ethyl)-(S)-methyl phenylalaninate A solution of 0.4 g (1.86 mmol) of (S)-methyl phenylalaninate in 6.5 ml of CH$_2$Cl$_2$ is added, at 0° C. over a period of 5 minutes, to a solution of 0.66 g (1.86 mmol) of (RS)-2-hydroxy-3-phenyl-tert.-butyl propionate filtrate and of 1.86 mmol of bis-1,8-(dimethylamino)-naphthalene in 6.5 ml of CH$_2$Cl$_2$. The solution is stirred at room temperature for 24 hours. It is filtered, the filtrate is washed with water and dried on MgSO$_4$. Filtration and concentration are then carried out. 1 g of the product is obtained, which is then chromatographied on silica.

Yield=82%

Weight=0.58 g

IR: 3320, 1735 cm$^{-1}$ $^1$H NMR (CDCl$_3$/TMS): 7.1 (m, 10 H), 3.55 and 3.5 (s, 3H), 3.5 to 3.15 (m, 2H), 3.0 to 2.7 (m, 4H), 2.05 (m, 1H), 1.25 and 1.2 (s, 9H).

G. Preparation of N-(RS)-[1-tert.-butoxycarbonyl-2-phenyl ethyl]-(S)-phenylalanine One equivalent of 1N NaOH is added at 0° C. to a solution of 1.5 mmol of the compound obtained in step F in solution in 5 ml of methanol. The solution is stirred for 24 hours at room temperature. The MeOH is evaporated and the aqueous phase is washed with ether. It is acidified with a 1N HCl solution and extracted with CHCl$_3$. The combined organic phases are dried on MgSO$_4$, filtered and concentrated.

Yield=87%

$^1$H NMR (CDCl$_3$/TMS): 7.3 to 6.7 (m, 10H), 6.3 (m, 2H), 3.5 to 3.2 (m, 2H), 3.15 to 2.6 (m, 4H), 1.35 and 1.3 (s, 9H).

H. Preparation of N-[N-(RS)-[1-tert.-butoxycarbonyl-2-phenyl ethyl]-(S)-phenylalanyl]-benzyl glycinate The compound obtained in step G is coupled to benzyl glycinate according to the operating procedure of example 1 (step f).

Yield=74% (chromatographied)

IR: 3300, 1730, 1670 cm$^{-1}$ $^1$H NMR (CDCl$_3$/TMS): 7.5 to 6.8 (m, 16H), 5.1 (s, 2H), 4.1 to 3.9 (m, 2H), 3.7 to 2.4 (m, 6H), 1.8 (m, 1H), 1.25 and 1.2 (s, 9H).

Microanalysis: C$_{31}$H$_{36}$O$_5$N$_2$

Calc % C=72.07 H=7.02 N=5.42

Found % C=71.85 H=6.91 N=5.38

EXAMPLE 91

Preparation of N-[N-(RS)-[1-carboxy-2-phenyl ethyl)-(S)-phenylalanyl]-glycine hydrochloride A solution of 0.9 mmol of the compound of example 90 H in 7 ml of ethanol is hydrogenated for 15 hours at room temperature in the presence of 50 mg of 10% palladium carbon. It is filtered, evaporated to dryness and the residue is taken up with 5 ml of a solution of 4N HCl in ethyl acetate. After 15 hours of continuous stirring, the solution is evaporated to dryness, the solid obtained is triturated in ether and dried on $P_2O_6$ in a dessicator.

Yield=90%
MP=80° C.
$^1$H NMR (CDCl$_3$/TMS): 9.0 to 7.8 (m, 4H), 7.1 (s, 11H), 4.6 to 2.8 (m, 8H).

Microanalysis: $C_{20}H_{23}O_5N_2Cl$
Calc % C=59.14 H=5.70 N=6.89
Found % C=59.40 H=6.10 N=6.50

EXAMPLE 92

Preparation of N-[N-(RS)-[1-tert.-butoxycarbonyl-2-phenyl ethyl]-(RS)-3-(3,4-methylenedioxy phenyl)-alanyl]-benzyl glycinate A. Preparation of N-(RS)-[1-tert.-butoxycarbonyl-2-phenyl ethyl]-(RS)-3-(3,4-methylenedioxy phenyl)-methyl alaninate (RS)-2-hydroxy-3-phenyl-tert.-butyl propionate triflate prepared in example 90E is substituted by (RS)-3-(3,4-methylenedioxy phenyl)-methyl alaninate according to the operating procedure of example 90 F.

Yield=53% (chromatographied)
$^1$H NMR (CDCl$_3$/TMS): 7.15 (s, 1H), 6.7 to 6.4 (m, 3H), 5.8 (s, 2H), 3.6 and 3.55 (s, 1H), 3.6 to 3.2 (m, 2H), 2.9 to 2.6 (m, 4H), 2.1 (m, 1H), 1.3 and 1.25 (s, 9H).

B. Preparation of N-(RS)-[1-tert.-butoxycarbonyl-2-phenyl ethyl]-(RS)-3-(3,4-methylenedioxy phenyl)-alanine The compound obtained in step A is deprotected according to the operating procedure of example 90 G.

Yield=87%
MP=128° C.
$^1$H NMR (CDCl$_3$/TMS): 7.2 (s, 5H), 6.7 (m, 3H), 5.9 (s, 2H), 5.8 to 5.0 (m, 2H), 3.7 to 2.4 (m, 6H), 1.35 and 1.3 (s, 9H).

C. Preparation of N-[N-(RS)-[1-tert.-butoxycarbonyl-2-phenyl ethyl]-(RS)-3-(3,4-methylenedioxy phenyl)-alanyl]-benzyl glycinate The product obtained in step B is coupled to benzyl glycinate according to the operating procedure of example 1 (step f).

Yield=73%
IR: 3340, 1740 to 1710, 1660 cm$^{-1}$
$^1$H NMR (CDCl$_3$/TMS): 7.3 (s, 5H), 7.1 (s, 5H), 6.8 to 6.3 (m, 4H), 5.8 (s, 2H), 5.1 (s, 2H), 4.1 to 3.9 (m, 2H), 3.7 to 2.3 (m, 6H), 1.8 (m, 1H), 1.25 (s, 9H).

Microanalysis: $C_{32}H_{36}O_7N_2$
Calc % C=68.56 H=6.47 N=5.00
Found % C=68.90 H=6.62 N=5.09

EXAMPLE 93

Preparation of N-[N-(RS)-[1-carboxy-2-phenyl ethyl]-(RS)-3-(3,4-methylenedioxy phenyl)-alanyl]-glycine hydrochloride The compound of example 92 C is deprotected according to the operating procedure of example 91.

Yield=93%
MP=127° C.
$^1$H NMR (CDCl$_3$/TMS): 9.2 to 7.7 (m, 4H), 7.2 (s, 5H), 7.1 to 6.4 (m, 4H), 5.8 (s, 2H), 4.6 to 2.8 (m, 8H).

Microanalysis: $C_{21}H_{23}O_7N_2Cl$
Calc % C=55.94 H=5.14 N=6.21
Found % C=56.30 H=5.29 N=6.15

EXAMPLE 94

Preparation of N-[N-(RS)-[1-tert.-butoxycarbonyl pentyl[-(RS)-3-(3,4-methylenedioxy phenyl)-alanyl]-benzyl glycinate A. Preparation of (RS)-2-hydroxy-hexanoic acid It is prepared using (RS) norleucine, according to the operating procedure of example 90 A.

Yield=53%
Rf value=0.48 (eluent: 70/30 benzene/acetic acid)
$^1$H NMR (CDCl$_3$/TMS): 7.3 (s, 5H), 4.3 (m, 3H), 2.2 to 0.65 (m, 9H), B. Preparation of (RS)-2-acetyloxy-hexanoic acid The compound obtained in step A is treated with acetyl chloride according to the process described in example 90 B.

Yield=98%
$^1$H NMR (CDCl$_3$/TMS): 11.8 (s, 1H), 4.9 (t, 1H, J=6.4 Hz), 2.0 (s, 3H), 2.0 to 0.6 (m, 9H).

C. Preparation of (RS)-2-acetyloxy-tert.-butyl hexanoate

The compound obtained in step B is esterified in the same way as in example 90 C.

Yield=82%
$^1$NMR (CDCl$_3$/TMS): 4.8 (t, 1H, J=6.4 Hz), 2.1 (s, 3H), 2.0 to 1.6 (m, 2H), 1.4 (s, 9H), 1.6 to 0.6 (7H).

D. Preparation of (RS)-2-hydroxy-tert.-butyl hexanoate

The compound obtained in step C is treated with 1N NaOH in the same way as in example 90 D.

Yield=67%
$^1$H NMR (CDCl$_3$/TMS): 4.0 (m, 1H), 2.8 (d, 1H, J=5.4 Hz), 1.9 to 0.6 (m, 18H).

E. (RS)-2-hydroxy-tert.-butyl hexanoate triflate

The compound obtained in step D is treated with trifluoromethane sulfonyl anhydride in the same way as in example 90 E.

Yield=46%
$^1$H NMR (CDCl$_3$/TMS): 5.1 (m, 1H), 1.9 to 0.7 (m, 18H).

F. Preparation of N-(RS)-(1-tert.-butoxycarbonyl pentyl)-(RS)-3-(3,4-methylenedioxy phenyl)-methyl alaninate (RS)-2-hydroxy-tert.-butyl hexanoate triflate is substituted by 3-(3,4-methylenedioxy phenyl)-methyl alaninate according to the operating procedure of example 90 F.

Yield=59% (chromatographied)
IR: 3340, 1735 cm$^{-1}$
$^1$H NMR (CDCl$_3$/TMS): 6.6 (m, 3H), 5.9 (s, 2H), 3.6 (s, 3H), 3.6 to 3.2 (m, 2H), 3.2 to 2.7 (m, 4H), 1.9 (m, 1H), 1.3 (s, 9H), 1.7 to 0.6 (m, 7H).

G. Preparation of N-(RS)-[1-tert.-butoxycarbonyl pentyl]-(RS)-3-(3,4-methylenedioxy phenyl)-alanine The compound obtained in step F is saponified according to the operating procedure of example 90 G.

Yield=82%
$^1$H NMR (CDCl$_3$/TMS): 6.7 (m, 3H), 5.9 (s, 2H), 5.8 to 5.3 (m, 2H), 3.6 to 2.8 (m, 6H), 1.4 (s, 9H), 2.1 to 0.5 (m, 7H).

H. Preparation of N-[N-(RS)-[1-tert.-butoxycarbonyl pentyl]-(RS)-3-(3,4-methylenedioxy phenyl)-alanyl-benzyl glycinate The compound obtained in step G is coupled to benzyl glycinate according to the operating procedure of example 1 (step f).

Yield=80%
IR: 3360, 1720, 1660 cm$^{-1}$

¹H NMR (CDCl₃/TMS): 7.3 (s, 5H), 6.7 (m, 4H), 5.85 (s, 2H), 5.2 (s, 2H), 4.1 to 3.9 (m, 2H), 3.6 to 2.4 (m, 6H), 1.4 (s, 9H), 2.0 to 0.6 (m, 8H),

Microanalysis: ($C_{29}H_{39}O_7N_2$)
Calc % C=66.14 H=7.27 N=5.32
Found % C=65.88 H=7.03 N=5.44

EXAMPLE 95

Preparation of N-[N-(RS)-[1-carboxy pentyl]-(RS)-3-(3,4-methylenedioxy phenyl)-alanyl]-glycine, hydrochloride The compound of example 94 H is deprotected according to the operating procedure of example 91.

Yield=94%
MP=85° C.

¹H NMR (CDCl₃/TMS): 9.2 to 7.8 (m, 4H), 7.2 to 6.4 (m, 4H), 5.8 (s, 2H), 4.8 to 3 (m, 8H), 2.3 to 0.6 (m, 7H).

Microanalysis: $C_{18}H_{25}O_7N_2Cl$
Calc % C=51.86 H=6.04 N=6.72
Found % C=51.68 H=6.21 1 N=6.53

EXAMPLE 96

Preparation of N-(R,S)-[2-(diethoxyphosphinyl) methyl-1-oxo-3-(3,4-methylenedioxy phenyl) propyl]-(S)-benzyl alaninate A. Preparation of 2-((3,4-methylenedioxy phenyl) methyl) propenoic acid chloride 1.3 ml of thionyl chloride (17.7 mmol, 1.5 eq.) are added, at 0° C. and with continuous stirring, to 2.43 g (11.8 mmol) of the product obtained in example 1 (step d). The temperature is left to return to 20° C. and, after 14 hours, the residual thionyl chloride is evaporated. 2.65 g of a yellow oil are obtained.

Yield=100%

¹H NMR: 3.50 (s, 2H), 5.60 (broad s, 1H), 5.95 (s, 2H), 6.45 (broad s, 1H), 6.75 (m, 3H).

B. Preparation of N-[1-oxo-2-((3,4-methylenedioxy phenyl) methyl) propenyl]-(S)-benzyl alaninate 1 g of triethylamine (10 mmol, 2 et.) in solution in 20 ml of tetrahydrofuran are added, at 0° C. and with continuous stirring, to 1.12 g of the product obtained in step A (5 mmol, 1 eq.) in solution in 50 ml of a 50/50 mixture of chloroform and tetrahydrofuran. 1.8 g of benzyl alaninate paratoluene sulfonate (5 mmol, 1 eg.) in solution in 50 ml of a 50/50 mixture of chloroform and tetrahydrofuran. The temperature is left to return to 20° C. and, after 14 hours, the solvents are evaporated. After taking up the residue with 50 ml of ethyl acetate and 50 ml of water, two washings are carried out with 100 ml of a 1N hydrochloric acid solution and 100 ml of a saturated sodium hydrogen carbonate aqueous solution. The organic phase is recovered, dried on magnesium sulfate, filtered and concentrated. Purification by chromatography (eluent: chloroform 97.5/methanol 2.5)

Yield=90%

1.50 g of a beige solid are obtained.
MP<50° C.

¹H NMR: 1.10 (d, 8H, J=6 Hz), 3.60 (s, 2H), 4.60 to 4.65 (m, 1H), 5.05 (s, 2H), 5.10 (broad s, 1H), 5.65 (broad s, 1H), 6.00 (s, 2H), 6.20 to 6.40 (broad s, 1H), 6.70 to 6.80 (m, 8H), 7.25 (broad s, 5H).

C. Preparation of N-(R,S)-[2-(diethoxyphosphinyl) methyl-1-oxo-3-(3,4-methylenedioxy phenyl) propyl]-(S)-benzyl alaninate 680 mg of diethylphosphite (4.6 mmol, 1 et.) in solution in 50 ml of tetrahydrofuran are added, under an inert atmosphere and at 0° C., to 220 mg of sodium hydride (5.5 mmol, 1.2 eq.) (at a concentration of 60% in mineral oil, previously washed with 1.2×10 ml of petroleum ether). After hydrogen emission has ceased, 1.50 g of the product obtained in step B (1 eq.) in solution in 25 ml of tetrahydrofuran are added. The temperature is left to return to 20° C. and, aster 14 hours, 2 ml of ethanol are added. The solvents are evaporated. Aster taking up the residue with 50 ml of ethyl acetate and 50 ml of water, two washings are carried out with 50 ml of a 1N hydrochloric acid solution and 50 ml of a saturated sodium hydrogen carbonate aqueous solution. The organic phase is recovered, dried on magnesium sulfate, filtered and concentrated. 1.50 g of an oil are recovered by chromatography (eluent: chloroform 96/methanol 4).

Yield=72%

¹H NMR: 1.10 to 1.40 (m, 9H), 1.70 to 2.65 (m, 2H), 2.70 to 3.25 (m, 3H), 3.40 to 4.20 (m, 4H), 4.55 to 4.65 (m, 1H), 5.10 (broad s, 2H), 6.00 (s, 2H), 6.20 to 6.80 (m, 4H), 7.20 (broad s, 5H).

IR: 3280, 1740, 1675, 1550, 1255, 1065, 1030 cm⁻¹
Microanalysis: $C_{25}H_{32}NO_8P$)
Calc % C=59.41 N=2.92 H=6.31
Found % C=59.58 N=2.79 H=6.25
MS: 505; 496, 468, 420, 401,380, 353, 311, 273, 234.

EXAMPLE 97

Preparation of N-(RS)-[2-(dihydroxyphosphinyl) methyl-1-oxo-3-(3,4-methylenedioxy phenyl) propyl]-(S)-alanine 3.33 ml of bromotrimethylsilane (24 mmol, 5.5 eq.) are added at room temperature, under an argon atmosphere and with continuous stirring, to a solution of 1.50 g of the product of example 96 C (3.31 mmol, 1 eq. ) in 7 ml of methylene chloride. After 4 hours, the mixture is concentrated. 15 ml of 6N hydrochloric acid are then added. After 14 hours, the water of the aqueous phase and the volatile products are evaporated and 657 mg of a hygroscopic orange solid are recovered.

Yield=99%

¹H NMR: (CD3OD) 1.20 (d, 3H, J=5 Hz), 1.70 to 2.55 (m, 2H), 2.65 to 3.35 (m, 3H), 4.50 to 4.60 (m, 1H), 4.80 (broad s, 4H), 5.00 (s, 2H), 6.20 to 6.80 (m, 3H).

Microanalysis: $C_{14}H_{18}NO_8P\cdot 2H_2O$
Calc % C=42.53 N=3.54 H=5.57
Found % C=43.27 N=3.68 H=5.43
MS: 359, 302, 287, 251, 196.

EXAMPLE 98

Preparation of the calcium monosalt of N-(RS)-[2-(dihydroxyphosphinyl)methyl -1-oxo-3-(3,4-methylenedioxy phenyl) propyl]-(S)-alanine A mixture of 325 mg of the product obtained in example 97 (1.19 mmol), 33.6 mg of calcium monoxide (0.60 mmol) and 5 of water are subjected to ultrasonic waves until the solid is totally dissolved. The water is evaporated and 350 mg of an off-white salt are recovered.

Yield=100%

Microanalysis: $C_{14}H_{17}NO_8P$, $Ca_{1/2}$
Calc % C=44.85 N=3.86 H=4.72
Found % C=44.24 N=3.74 H=4.65

EXAMPLE 99

Preparation of N-(RS)-[2-(diethoxyphosphinyl) methyl-1-oxo-3-(3,4-methylenedioxy phenyl) propyl]-benzyl glycinate A. Preparation of N-(1-oxo-2-(3,4-methylenedioxy phenyl) methyl propenyl)-benzyl glycinate The operating procedure is identical to that described in example 96 B, except that benzylglycinate paratoluene sulfonate is used instead of benzyl alaninate paratoluene sulfonate. Purification by chromatography (eluent: chloroform 97.5/methanol 2.5).

Yield=88%

A beige solid is obtained.

$^1$H NMR: 3.60 (s, 2H), 4.05 (broad s, 2H), 5.05 (s, 2H), 5.10 (s, 1H), 5.65 (broad s, 1H), 6.00 (s, 2H), 6.20 to 6.40 (broad s, 1H), 6.70 to 6.80 (m, 3H), 7.25 (broad s, 5H).

B. Preparation of N-(RS)-[2-(diethoxyphosphinyl) methyl-1-oxo-3-(3,4-methylenedioxy phenyl) propyl]-benzyl glycinate The operating procedure is identical to that described in example 96 C, except that benzyl glycinate is used instead of benzyl alaninate. A beige powder is obtained. Purification by chromatography (eluent: chloroform 96/methanol 4).

Yield=69%
MP<50° C.

$^1$H NMR: 1.10 to 1.35 (t, 6H, J=7 Hz), 1.70 to 2.65 (m, 2H), 2.70 to 3.25 (m, 3H), 3.40 to 4.20 (m, 6H), 5.10 (s, 2H), 6.00 (s, 2H), 6.20 to 6.80 (m, 4H), 7.20 (broad s, 5H).

Microanalysis: $C_{24}H_{30}O_8P$
Calc % C=58.66 N=2.85 H=6.31
Found % C=58.77 N=2.79 H=6.25
MS: 491, 400, 372, 344, 312, 286.

EXAMPLE 100

Preparation of N-(RS)-[2-(dihydroxyphosphinyl) methyl-1-oxo-3-(3,4-methylenedioxy phenyl) propyl]-glycine The operating procedure is identical to that described in example 97, except that the product obtained in example 99 B is used instead of the product obtained in example 96 C. A hygroscopic orange solid is obtained.

Yield=99%

$^1$H NMR: (CD3OD) 1.70 to 2.55 (m, 2H), 2.65 to 3.30 (m, 3H), 4.05 (broad s, 2H), 4.80 (broad s, 4H), 6.00 (s, 2H), 6.20 to 6.80 (m, 4H).

Microanalysis: $C_{13}H_{16}NO_8P \cdot 2H_2O$
Calc % C=40.94 N=3.67 H=5.25
Found % C=41.19 N=3.68 H=5.03
MS=345, 300, 271, 243, 211, 175, 121.

EXAMPLE 101

Preparation of the calcium monosalt of N-(RS)-[2-(dihydroxyphosphinyl) methyl-1-oxo-3-(3,4-methylenedioxy phenyl) propyl]-glycine The operating procedure is identical to that described in example 98, except that the product obtained in example 100 is used instead of the product obtained in example 97. A white powder is obtained.

Yield=100%
Microanalysis: $C_{13}H_{16}NO_8P,Ca_{1/2}$
Calc % C=42.86 N=3.85 H=4.67
Found % C=43.14 N=3.74 H=4.75

EXAMPLE 102

Preparation of N-(RS)-[2-(diethoxyphosphinyl) methyl-1-oxo-3-(4-phenyl phenyl) propyl]-(S)-benzyl alaninate A. Preparation of 2-((4-phenyl phenyl)-methyl) propenoic acid chloride The acid chloride is prepared by reacting (2-(4-phenyl) benzyl) acrylic acid with thionyl chloride according to the operating procedure of example 96 A. A yellow oil is obtained.

Yield=100%

$^1$H NMR: 3.50 (s, 2H), 5.64 (s, 1H), 6.48 (s, 1H), 7.20 to 7.70 (m, 9H).

B. Preparation of N-[2-(4-phenyl phenyl) methyl-1-oxo propenyl]-(S)-benzyl alaninate The product obtained in step A is coupled according to the operating procedure of example 96 B.

Chromatography (eluent: chloroform 97.5/methanol 2.5)
Yield=91% 1.50 g of a beige solid are obtained.
MP<50° C.

$^1$H NMR: 1.10 (d, 3H, J=6 Hz), 3.60 (s, 2H), 4.50 to 4.60 (m, 1H), 5.00 (s, 2H), 5.10 (s, 1H), 5.60 (broad s, 1H), 6.20 to 6.40 (broad s, 1H), 7.20 to 7.70 (m, 14H).

C. Preparation of N-(R,S)-[2-(diethoxyphosphinyl) -methyl-1-oxo-3-(4-phenyl phenyl) propyl]-(S)-benzyl alaninate It is prepared from the compound obtained in step B, according to the operating procedure of example 96 C.

Chromatography (eluent: chloroform 96/methanol 4).
An oil is obtained.
Yield=69%

$^1$H NMR: 1.10 to 1.40 (m, 9H), 1.70 to 2.65 (m, 2H), 2.70 to 3.30 (m, 3H), 3.40 to 3.80 (q, 4H, J=6 Hz), 4.50 to 4.60 (m, 1H), 5.10 (s, 2H), 6.20 to 6.50 (broad s, 1H), 7.20 to 7.80 (m, 14H).

IR: 3280, 1740, 1675, 1550, 1255, 1065, 1030 cm$^{-1}$

Microanalysis: $C_{30}H_{36}NO_6P$
Calc % C=67.03 N=2.61 H=6.75
Found % C=67.58 N=2.74 H=6.75
MS: 537, 446, 418, 390, 341, 318, 285, 247.

EXAMPLE 103

Preparation of N-(RS)-[2-(dihydroxyphosphinyl) methyl-1-oxo-3-(4-phenyl phenyl)]-(S)-alanine The product of example 102 C is deprotected according to the operating procedure of example 97.

An oil is isolated by chromatography (eluent: chloroform/methanol 4).

Yield=73%

$^1$H NMR (CD3OD): 1.25 (d, 3H, J=5 Hz), 1.70 to 2.65 (m, 2H), 2.70 to 3.20 (broad s, 3H), 4.55 to 4.60 (m, 1H), 4.80 (broad s, 4 H), 7.20 to 7.80 (m, 9H).

Microanalysis: $C_{19}H_{22}NO_6P \cdot 2H_2O$
Calc % C=53.40 N=3.28 H=6.13
Found % C=54.27 N=3.39 H=6.02
MS: 391,342, 319, 256, 194, 176.

EXAMPLE 104

Preparation of the calcium monosalt of N-(RS)-[2-(dihydroxyphosphinyl)-methyl-1-oxo-3-(4-phenyl phenyl) propyl]-(S)-alanine The product of example 103 is treated according to the process described in example 98.

A white powder is obtained.
Yield=100%
Microanalysis: $C_{19}H_{21}NO_6P,Ca_{1/2}$
Calc % C=55.61 N=3.41 H=5.16
Found % C=55.49 N=3.54 H=5.26

EXAMPLE 105

Preparation of N-(RS)-[2-(diethoxyphosphinyl) methyl-1-oxo-3-(4-phenyl phenyl) propyl]-benzyl glycinate A. Preparation of N-[2-(4-phenyl phenyl) methyl-1-oxo propenyl]-benzyl glycinate The compound of example 102 A is coupled to benzyl glycinate according to the operating procedure of example 96 B. A white powder is obtained. Purification by chromatography (eluent: chloroform 97.5/methanol 2.5).
Yield=92%
$^1$H NMR: 3.60 (s, 2H), 4.05 (broad s, 2H), 5.05 (s, 2H), 5.10 (s, 1H), 5.60 (broad s, 1H), 6.20 to 6.40 (broad s, 1H), 7.20 to 7.75 (m, 14H).

B. Preparation of N-(RS)-[2-(diethoxyphosphinyl) -methyl-1-oxo-3-(4-phenyl phenyl) propyl]-benzyl glycinate It is prepared in the same way as in example 96 C. A beige powder is obtained which is purified by chromatography (eluent: chloroform 96/methanol 4)
Yield=70%
MP<50° C.
$^1$H NMR: 1.10 to 1.35 (t, 6H, J=7 Hz), 1.70 to 2.65 (m, 2H), 2.70 to 3.25 (m, 3H), 3.40 to 4.20 (m, 6H), 5.10 (broad s, 2H), 6.30 to 6.70 (broad s, 1H), 7.20 to 7.80 (m, 14H).
Microanalysis: $C_{29}H_{34}NO_6P$
Calc % C=66.53 N=2.68 H=6.55
Found % C=66.58 N=2.73 H=6.45
MS: 523, 432, 404, 376, 317, 281.

EXAMPLE 106

Preparation of N-(RS)-[2-(dihydroxyphosphinyl) methyl-1-oxo-3-(4-phenyl phenyl) propyl]-glycine The compound of example 105 B is treated according to the process described in example 97. A hygroscopic orange solid is obtained.
Yield=98%
$^1$H NMR: (CD30D) 1.95 to 2.55 (m, 2H), 2.65 to 3.30 (m, 3H), 4.05 (broad s, 1H), 4.80 (broad s, 4H), 6.20 to 6.50 (broad s, 1H).
Microanalysis: $C_{18}H_{20}NO_6P \cdot 2H_2O$
Calc % C=52.30 N=3.39 H=5.85
Found % C=53.13 N=3.48 H=5.73
MS: 333, 254, 188, 164

EXAMPLE 107

Preparation of the calcium monosalt of N-(RS)-[2-(dihydroxyphosphinyl) methyl-1-oxo-3-(4-phenyl phenyl) propyl]-glycine The product of example 106 is treated according to the process described in example 98. A white powder is obtained.
Yield=100%
Microanalysis: $C_{18}H_{19}NO_6P,Ca_{1/2}$
Calc % C=54.55 N=3.53 H=4.83
Found % C=54.69 N=3.44 H=4.92

BIOLOGICAL STUDY

Quantitative determinations of the enkephalinase (Enkase) and ACE inhibiting activities (Giros et al., J. Pharmac. Exp. Ther., 1987, 248, 666) of the above-mentioned I compounds are carried out.

Table I gives the results obtained from I compounds in racemic form and table II gives the results obtained from a number of I compounds in optically pure form.

TABLE 1

MIXED INHIBITORS

[Structure: HS-CH2-CH(CH2R1)-C(=O)-NH-CH(R2)-C(=O)-OH (RS)(S)]

| COMPOUND | CH$_2$R$_1$ | R$_2$ | IC 50 (nm) EDC | IC 50 (nm) ACE |
|---|---|---|---|---|
| EX 1 | | H | 8 | 8 |
| EX 12 | | nPr | 10 | 6 |
| EX 14 | | nBu | 4 | 10 |
| EX 18 | —CH$_2$-(4-methylenedioxyphenyl) | —CH$_2$-(indol-3-yl) | 4 | 4 |
| EX 20 | | —CH$_2$—Ph | 10 | 8 |

TABLE 1-continued

MIXED INHIBITORS

[Structure: HS-CH2-CH(CH2R1)-C(=O)-NH-CH(R2)-C(=O)-OH (RS)(S)]

| COMPOUND | CH₂R₁ | R₂ | IC 50 (nm) | |
|---|---|---|---|---|
| | | | EDC | ACE |
| EX 22 | | −CH₂−C₆H₄−OH (para) | 6 | 1,5 |
| EX 32 | −CH₂−(3,4-ethylenedioxyphenyl) | H | 5 | 10 |
| EX 49 | −CH₂−(3-fluorophenyl) | H | 3 | 10 |
| EX 57 | −CH₂−(3,5-difluorophenyl) | H | 4 | 8 |
| EX 59 | −CH₂−(3,5-difluorophenyl) | CH₃ | 2,5 | 10 |
| EX 64 | −CH₂−(indanyl) | CH₃ | 8 | 10 |
| EX 68 | −CH₂−(2,3-dihydrobenzofuranyl) | CH₃ | 5 | 9 |

TABLE II

OPTICALLY PURE MIXED INHIBITORS

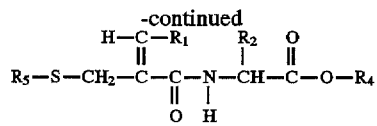

| COMPOUND | CH₂—R₁ | R₂ | IC 50 (nm) EDC | ACE |
|---|---|---|---|---|
| EX 4 | (benzodioxole-CH₂—) | H | 5 | 5 |
| EX 8 | (benzodioxole-CH₂—) | CH₃ | 2 | 10 |
| EX 24 | (benzodioxole-CH₂—) | CH₂—OH | 3 | 11,7 |
| EX 26 | (benzodioxole-CH₂—) | CH₂—CH₂—SCH₃ | 0,75 | 4,8 |
| EX 45 | —CH₂—(biphenyl) | CH₃ | 0,2 | 10 |
| EX 60 | —CH₂—(fluorophenyl) | CH₃ | 1,5 | 9 |

It can be seen that the compounds listed in these tables have IC50 inhibiting concentrations which range from 0.1 to 1 nM and a ratio of inhibiting activities on the two enzymes of less than 3–4. These compounds are excellent mixed inhibitors of enkephalinase and ACE enzymes.

It can also be seen that the use of compounds Ia or Ib in optically pure form further improves their enkephalinase- and ACE-inhibiting properties (see example 4).

In conformity with their in vitro twofold inhibiting activity, it was observed that the compounds listed in tables I and II, or their esterified or thioesterified derivatives, administered by oral route at a dose of 3 mg/kg lead to: a slowing down in the degradation of $^{125}$I ANF in the mouse, an increase in natriuresis and diuresis in the normally or spontaneously hypertensive rat, a significant decrease in average blood pressure.

What is claimed is:

1. Amino acid derivative corresponding to the general formulae

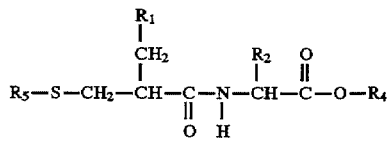

-continued $$R_5-S-CH_2-\underset{\underset{O}{\|}}{\overset{\overset{H-C-R_1}{|}}{C}}-\underset{H}{\overset{R_2}{\underset{|}{C}}}-N-CH-\overset{O}{\overset{\|}{C}}-O-R_4$$

wherein

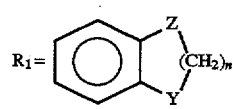

wherein Z and Y are O and n=1 or 2

R₂ represents a hydrogen atom, a lower alkyl group, a lower hydroxyalkylene group, a phenyl group, a lower phenylalkylene group, a lower hydroxyphenylalkylene group, a lower aminoalkylene group, a lower guanidinoalkylene group, a lower mercaptoalkylene group, a lower alkylthio lower alkylene group, a lower imidazolylalkylene group, a lower indolylalkylene group, a lower carbamylalkylene group, a lower carboxylalkylene group or one of the following groups:

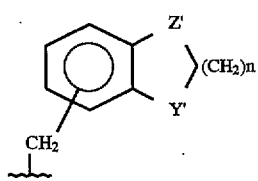

wherein Z', Y' and n have the meanings defined below:

| Z' | Y' | n |
|---|---|---|
| O | O | 1 |
| O | O | 2 |
| O | $CH_2$ | 1 |
| $CH_2$ | $CH_2$ | 1 |
| $CH_2$ | $CH_2$ | 2 | wherein $R_4$ represents a linear or branched alkyl group, a phenyl group or a phenylalkyl group, and wherein $R_5$ represents a linear or branched aliphatic acyl radical, or an aromatic acyl radical.

2. Drug showing enkephalinase-inhibiting and ACE-inhibiting activities containing the compound of claim 1 as the active principle.

3. Drug according to claim 2 wherein said compound is present in the form of unit doses containing 1 to 200 mg of active principle.

4. A method of inhibiting the activity of enkephalinase and ACE enzymes which comprises adding thereto a sufficient amount of the compound of claim 1.

* * * * *